United States Patent
Constantine

(10) Patent No.: US 11,931,334 B2
(45) Date of Patent: *Mar. 19, 2024

(54) METHODS AND COMPOSITIONS FOR TREATING CANNABIS USE DISORDER AND MITIGATING CANNABINOID WITHDRAWAL

(71) Applicant: PleoPharma, Inc., Phoenixville, PA (US)

(72) Inventor: Ginger D. Constantine, Malvern, PA (US)

(73) Assignee: PLEOPHARMA, INC., Phoenixville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/546,874

(22) Filed: Dec. 9, 2021

(65) Prior Publication Data

US 2022/0273612 A1    Sep. 1, 2022

Related U.S. Application Data

(63) Continuation of application No. 17/244,585, filed on Apr. 29, 2021, now Pat. No. 11,197,846, which is a continuation-in-part of application No. PCT/US2021/020921, filed on Mar. 4, 2021.

(60) Provisional application No. 62/985,097, filed on Mar. 4, 2020.

(51) Int. Cl.
  *A61K 31/352*   (2006.01)
  *A61K 31/195*   (2006.01)
  *A61K 31/353*   (2006.01)
  *A61P 25/30*    (2006.01)

(52) U.S. Cl.
  CPC .......... *A61K 31/353* (2013.01); *A61K 31/195* (2013.01); *A61P 25/30* (2018.01)

(58) Field of Classification Search
  CPC ...... A61K 31/352; A61K 31/195; A61P 25/30
  USPC ................................................. 514/454, 561
  See application file for complete search history.

(56) References Cited

U.S. PATENT DOCUMENTS

| | | | |
|---|---|---|---|
| 11,197,846 | B2 | 12/2021 | Constantine |
| 2010/0280118 | A1 | 11/2010 | Mason |
| 2017/0100341 | A1 | 4/2017 | Tygesen et al. |
| 2017/0304327 | A1 | 10/2017 | Thatte et al. |
| 2021/0275492 | A1 | 9/2021 | Constantine |

FOREIGN PATENT DOCUMENTS

| | | |
|---|---|---|
| WO | 2014100231 A1 | 6/2014 |
| WO | 2018102296 A1 | 6/2018 |
| WO | 2021178700 A1 | 9/2021 |

OTHER PUBLICATIONS

Takasaki et al., Gabapentin Antinociception in Mice with Acute Herpetic Pain Induced by Herpes Simplex Virus Infection, JPET, (2001), 296:270-275.
Turcotte et al., Original Research Articles Nabilone as an Adjunctive to Gabapentin for Multiple Sclerosis-Induced Neuropathic Pain: A Randomized Controlled Trial, Pain Medicine, (2015), 16:149-159.
Ware et al., The abuse potential of the synthetic cannabinoid nabilone, Addiction, (2010), 105:494-503.
Ware et al., A prospective observational study of problematic oral cannabinoid use, Psychopharmacology, (2018), 235:409-417.
Budney et al., Marijuana Dependence and its Treatment, Addiction Science & Clinical Practice, (2007), p. 4-16.
Drug Abuse and Drug Abuse Research, Secretary, department of Health and Human Services, (1984), Publication No. (ADM)85-1372, 1-170.
Diagnostic and Statistical manual of mental disorders: DSM-5, American Psychiatric Association, (2013).
D'Souza et al., Rapid Changes in CB1 Receptor Availability in Cannabis Dependent Males after Abstinence from Cannabis, Biol Psychiatry Cogn Neurosci Neuroimaging, (2016), 1:60-67.
Gorelick et al., Diagnostic Criteria for Cannabis Withdrawal Syndrome, Drug Alcohol Depend, (2012), 123(1-3): 141-147.
Heatherton et al., The Fagerstrom Test for Nicotine Dependence: a revision of the Fagerstrom Tolerance Questionnaire, British Journal of Addiction, (1991), 86:1119-1127.
Hesse et al., Time-course of the DSM-5 cannabis withdrawal symptoms in poly-substance abusers, BMC Psychiatry, (2013), 13:258, p. 1-11.
Hirvonen et al., Reversible and regionally selective downregulation of brain cannabinoid CB1 receptors in chronic daily cannabis smokers, Molecular Psychiatry, (2012), 17:642-649.
Fraser et al., Lack of Interference by Nabilone in the EMIT® d.a.u. Cannabinoid Assay, Abbott TDX® Cannabinoid Assay, and a Sensitive TLC Assay for A9-THC-Carboxylin Acid, Journal of Analytical Toxicology, (1989), 13:1.
Inder et al., Measurement of salivary cortisol in 2012—laboratory techniques and clinical indications, Clinical Endocrinology, (2012), 77:645-651.
Keyhani et al. Risks and Benefits of Marijuana Use: A National Survey of U.S. Adults, Ann Intern Med, (2018), 169(5):282-290.
Lee et al., Cannabis Withdrawal in Chronic, Frequent Cannabis Smokers during Sustained Abstinence within a Closed Residential Environment, Am J Addict, (2014), 23(3):234-242.
Bestard et al., An Open-Label Comparison of Nabilone and Gabapentin as Adjuvant Therapy or Monotherapy in the Management of Neuropathic Pain in Patients with Peripheral Neuropathy, Pain Practice, (2011), 11(4):353-368.
Clayton et al., Young Men and Drugs in Manhattan: A Casual Analysis, National Institute on Drug Abuse, (1981), p. 1-211.
Restituto et al., Advantage of salivary cortisol measurements in the diagnosis of glucocorticoid related disorders, Clinical Biochemistry, (2008), 41:688-692.

(Continued)

*Primary Examiner* — Charanjit Aulakh
(74) *Attorney, Agent, or Firm* — Nevrivy Patent Law Group P.L.L.C.

(57) ABSTRACT

The present invention provides methods of treating *cannabis* withdrawal syndrome and other *cannabis* related conditions, including *cannabis* use disorder, in a subject, comprising administering to the subject in need thereof an effective amount of a cannabinoid or an effective amount of a cannabinoid and an effective amount of a second active agent, such as gabapentin or a gabapentin analog.

41 Claims, 27 Drawing Sheets

(56) References Cited

OTHER PUBLICATIONS

Subramaniam et al., The Cardiovascular Effects of Marijuana: Are the Potential Adverse Effects Worth the High?, Missouri Medicine, (2019), 116: 146- 153.
Zehra et al., Cannabis Addiction and the Brain: a Review, Journal of Neuroimmune Pharmacology, (2018), 13:438-452.
Key Substance Use and Mental Health Indicators in the United States: Results from the 2019 National Survey on Drug Use and Health, SAMHSA, p. 1-114.
Allsop et al., The Cannabis Withdrawal Scale development: Patterns and predictors of cannabis withdrawal and distress, Drug and Alcohol Dependence, (2011), 119:123-129.
Leung et al., What is the prevalence and risk of cannabis use disorders among people who use cannabis? a systematic review and meta-analysis, Addictive Behaviors, (2020), 109:106479.
Sullivan et al., Pharmacokinetics of Nabilone, a Psychotropically Active 9=Ketocannabinoid, in the Dog. Utilization of Quantitative Selected Ion Monitoring and Deuterium Labeling, Biomedical Mass Spectrometry, (1978), 5:296-301.
International Search Report from Application No. PCT/US2021/020921, dated May 19, 2021.
Wikipedia, Area under the curve (pharmacokinetics), Oct. 12, 2018, retrieved on Apr. 29, 2021 fom https://en.wikipedia.org/w/index.php?title=Area_under_the_curve_(pharmacokinetics)&oldid=863688840, entire document, espceially pag. 1 para 1.
Highlights of Prescribing Information, Ambien (1992), p. 1-7.
Highlights of Prescribing Information, Neurontin, (1993), p. 1-32.
Haney et al., Effects of Baclofen and Mirtazapine on a Laboratory Model of Marijuana Withdrawal and Relapse, Psychopharmacology (Berl), (2010), 211: 233-244.
Highlights of Prescribing Information, Depakote, (1983), p. 1-54.
Levin et al., Pharmacotherapy for Marijuana Dependence: A Double-blind, Placebo-controlled Pilot Study of Divalproex Sodium, Am J Addict, (2004), 13:21-32.
Weir et al., Journal of neurology, Motor unit potential abnormalities in multiple sclerosis: further evidence for a peripheral nervous system defect, (1980), Journal of Neurology, Neurosurgery, and Psychiatry, 43:999-1004.
Sandercock et al., Sandercock, Gabapentin Extended Release for the Treatment of Painful Diabetic Peripheral Neuropathy, Diabetes Care, (2009), 32:1-2.
Morello et al., Randomized Double-blind Study Comparing the Efficacy of Gabapentin With Amitriptyline on Diabetic Peripheral Neuropathy Pain, Arch Intern Med. (1999), 159:1931-1937.
Rao et al., Efficacy of Gabapentin in the Management of Chemotherapy-induced Peripheral Neuropathy, American Cancer Society, (2007), 2110-2118.
Montoya et al., Cannabis Use Disorders, Springer Nature Switzerland AG, (2019), 1-16.
Shahbazi et al., Cannabinoids and Cannabinoid Receptors: The Story so Far, iScience, (2020), 1-22.
Orange Book: Approved Drug Products with Therapeutic Equivalence Evaluations, Cesamet (Nabilone), (1985), p. 1.
Orange Book: Approved Drug Products with Therapeutic Equivalence Evaluations, Neurontin (Gabapentin), (1993), p. 1-2.
Cottler et al., The DSM-IV field trial for substance use disorders: major results, Drug and Alcohol Dependence, (1995), 38:59-69.
Wiesbeck et al., An evaluation of the history of a marijuana withdrawal syndrome in a large population, Addiction, (1996), 91:1469-1478.
Diagnostic and Statistical Manual of Mental Disorders DSM-5, American Psychiatric Association (2013), p. 509-510.
Diagnostic and Statistical Manual of Mental Disorders DSM-5, American Psychiatric Association (2013), p. 517-518.
Table 5.14A and Table 5.14B, Samhsa, Center for Behavioral Health Statistics and Quality, National Survey on Drug Use and Health, (2018-2019), 200416.
Bonnet et al., Abstinence phenomena of chronic cannabis-addicts prospectively monitored during controlled npatient detoxification: Cannabis withdrawal syndrome and its correlation with delta-9-tetrahydrocannabinol and -metabolites in serum, Drug and Alcohol Dependence, (2014), 143:189-197.
Gabapentin Treatment of Cannabis Dependence, NIH, (2017), ClinicalTrials.gov, NCT00974376.
Office Action from U.S. Appl. No. 17/244,585, dated Jul. 9, 2021.
Alden et al., Differential Effect of Gabapentin on Neuronal and Muscle Calcium Currents, JPET, (2001), 297:727-735.
Allsop et al., Quantifying the Clinical Significance of Cannabis Withdrawal, PLOS ONE, (2012), 7:e44864.
Archer et al., Cannabinoids. 3. Synthetic Approaches to 9-Ketocannabinoids, Total Synthesis of Nabilone, J. Org. Chem., (1977), 42:2277-2284.
Atwal et al., THC and gabapentin interactions in a mouse neuropathic pain model, Neuropharmacology, (2019), 144:115-121.
Bahji et al. Prevalence of Cannabis Withdrawal Symptoms Among People With Regular or Dependent Use of Cannabinoids, JAMA Network Open, (2020), 3:1-17, e202370.
Bedi et al., Subjective, cognitive, and cardiovascular dose-effect profile of nabilone and dronabinol in marijuana smokers, Addict Biol., (2013), 18: 872-881.
Billings et al., The stereoselective enzymic reduction of the synthetic 9-ketocannabinoid, nabilone, in vivo, In isolated liver cells and in liver homogenate, Xenobiotica, (1980), 10:33-36.
Bonnet et al., The cannabis withdrawal syndrome: current insights, Substance Abuse and Rehabilitation, (2017), 8:9-37.
Brezing et al., The Current State of Pharmacological Treatments for Cannabis Use Disorder and Withdrawal, Neuropsychopharmacology Reviews, (2018), 43:173-194.
Cesament—Nabilone Capsule, Bausch Health US LLC, (2020), p. 1-12.
Corsi et al., Association Between Self-reported Prenatal Cannabis Use and Maternal, Perinatal, and Neonatal Outcomes, JAMA, (2019), 322: 145-152.
Darmani, Δ9-Tetrahydrocannabinol and Synthetic Cannabinoids Prevent Emesis Produced by the Cannabinoid CB1 Receptor Antagonist/ Inverse Agonist SR 141716A, Neuropsychopharmacology, (2001), 24:198-203.
Eroglu et al., The Gabapentin Receptor α2δ-1 is the Neuronal Thrombospondin Receptor Responsible for Excitatory CNS Synaptogenesis, Cell, (2009), 139(2):380-392.
Field et al., Evaluation of Gabapentin and S-(+)-3-Isobutylgaba in a Rat Model of Postoperative Pain, JPET, (1997), 282:1242-1246.
Gareau et al., Structure activity relationships of tetrahydrocannabinol analogues on human cannabinoid receptors, Bioorganic & Medicinal Chemistry Letters, (1996), 6:189-194.
Gee et al., The Novel Anticonvulsant Drug, Gabapentin (Neurontin), Binds to the a2d Subunit of a Calcium Channel, The Journal of Biological Chemistry, (1996), 271:5768-5776.
Ghaemi et al., Gabapentin Treatment of Mood Disorders: A Preliminary Study, J Clin Psychiatry, (1998), 59:.426-429.
Highlights of Prescribing Information, Gralise, (2015), p. 1-18.
Hanasono et al., A Species comparison of the Toxicity of Nabilone, a New Synthetic Cannabinoid, Fundamental and Applied Toxicology, (1987), 9:185-197.
Haney, Effects of Smoked Marijuana in Healthy and HIV+ Marijuana Smokers, J Clin Pharmacol, (2002), 42:34S-40S.
Haney, Opioid Antagonism of Cannabinoid Effects: Differences between Marijuana Smokers and Nonmarijuana Smokers, Neuropsychopharmacology, (2007), 32:1391-1403.
Haney et al., Abstinence symptoms following smoked marijuana in humans, Psychopharmacology, (1999), 141:395-404.
Haney et al., Dronabinol and marijuana in HIV+ marijuana smokers: acute effects on caloric intake and mood, Psychopharmacology, (2005), 181:170-178.
Haney et al., Nabilone Decreases Marijuana Withdrawal and a Laboratory Measure of Marijuana Relapse, Neuropsychopharmacology, (2013), 38:1557-1565.
Harden et al., A Beneficial Effect on Mood in Partial Epilepsy Patients Treated with Gabapentin, Epilepsia, (1999), 40: 1129-1134.
Hart et al., Effects of Acute Smoked Marijuana on Complex Cognitive Performance, Neuropsychopharmacology, (2001), 25:757-765.

(56) References Cited

OTHER PUBLICATIONS

Herrmann et al., Effects of zolpidem alone and in combination with nabilone on cannabis withdrawal and a laboratory model of relapse in cannabis users, Psychopharmacology (Berl), (2016), 233: 2469-2478.
Herrmann et al., Varenicline and nabilone in tobacco and cannabis cousers: effects on tobacco abstinence, withdrawal and a laboratory model of cannabis relapse, Addiction Biology, (2018), 24:765-776.
Hill et al., Nabilone Pharmacotherapy for Cannabis Dependence: A Randomized, Controlled Pilot Study, Am J Addict., (2017),26:795-801.
Hwang et al., Effect of Subarachnoid Gabapentin on Tactile-Evoked Allodynia in a Surgically Induced Neuropathic Pain Model in the Rat, Regional Anesthesia, (1997), 22:249-256.
Lemberger et al., Pharmacokinetics, metabolism and drug abuse potential of nabilone, Cancer Treatment Reviews, (1982), 9(Suppl. B):17-23.
Lile et al., Substitution Profile of the Cannabinoid Agonist Nabilone in Human Subjects Discriminating Δ9 Tetrahydrocannabinol, Clinical Neuropharmacology, (2010), 5:235-242.
Lile et al., Separate and combined effects of the cannabinoid agonists nabilone and Δ9-THC in humans discriminating Δ9-THC, Drug Alcohol Depend, (2011), 116(1-3):86-92.
Lo et al., Treatment Effects of Gabapentin for Primary Insomnia, Clinical Neuropharmacology, (2010), 33:84-90.
Lu et al., A double-blind placebo control pilot study on the safety and tolerability of Nabilone in marijuana users, Mental Health and Substance USe, (2013), 6:133-139.
Maldonado et al., Neurochemical Basis of Cannabis Addiction, Neuroscience, (2011), 181:1-17.
Mason et al., Proof-of-Concept Human Laboratory Study for Protracted Abstinence in Alcohol Dependence: Effects of Gabapentin, Addict Biol, (2009), 14:73-83.
Mason et al., A Proof-of-Concept Randomized Controlled Study of Gabapentin: Effects on Cannabis Use, Withdrawal and Executive Function Deficits in Cannabis-Dependent Adults, Neuropsychopharmacology, (2012), 37:1689-1698.
Matsuda et al., Molecular Aspects of Cannabinoid Receptors, Critical ReviewsTM in Neurobiology, (1997), 11:143-166.
Moss et al., Measures of Substance Consumption Among Substance Users, DSM-IV Abusers, and Those With DSM-IV Dependence Disorders in a Nationally Representative Sample, Journal of Studies on Alcohol and Drugs, (2012), p. 820-828.
Patra et al., Effect of the synthetic cannabinoid nabilone on spermatogenesis in mice, Experientia, (1990), 46:852-854.
Perkonigg et al., The natural course of cannabis use, abuse and dependence during the first decades of life, The Authors. Journal compilation, (2008), 103:439-449.
Radulovic et al., Disposition of Gabapentin (Neurontin) in Mice, Rats, Dogs, and Monkeys, Drug Metabolism and disposition, (1995), 23:441-448.
Roberto et al., Cellular and Behavioral Interactions of Gabapentin with Alcohol Dependence, The Journal of Neuroscience, (2008), 28:5762-5771.
Rodriguez et al., Activation of Corticotropin-Releasing Factor in the Limbic System During Cannabinoid Withdrawal, science, (1997), 276:2050-2054.
Rose et al., Gabapentin: pharmacology and its use in pain management, Anaesthesia, (2002), 57:451-462.
Rubin et al., Physiologie disposition of nabilone, a eannabinol derivative, in man, Clinical Pharmacology and Therapeutics, (1977), 22:85-91.
Sullivan et al., Species specificity in the metabolism on nabilone. Relationship between toxicity and metabolic routes, Xenobiotica, (1987), 17:459-468.
Supplemntary European Search Report from Appl. No. EP21765401, dated Dec. 11, 2023.
Kraft et al., Der Einfluss von Cannabis und Cannabinoiden auf Anästhesie und Analgesie in der perioperativen Phase, Schmerz, (2020), 34:314-318.
Haney et al., Nabilone Decreases Marijuana Withdrawal and a Laboratory Measure of Marijuana Relapse, Neuropsychopharmacology, m(2013), 38:1557-1565.
Levesque et al., When and How to Treat Possible Cannabis Use Disorder, Medical Clinics of North America, (2018), 102:667-681.
Chinese Office Action from Appl. No. 202180032529, dated Jan. 6, 2024.
Translation of Chinese Office Action from Appl. No. 202180032529, dated Jan. 6, 2024.
Lam et al., Nabilone therapy for cannabis withdrawal presenting as protracted nausea and vomiting, BMJ Case Rep, (2014), p. 1-3.

FIG. 19

| Treatment Days (inclusive) | Total Nabilone Dose (mg) | Total Gabapentin Dose (mg) | Total Nabilone Dose (mg) | Total Gabapentin Dose (mg) |
|---|---|---|---|---|
| 1-3 | 6 | 300 | 6 | 240 |
| 4-7 | 5 | 600 | 5 | 500 |
| 8-10 | 4 | 900 | 4 | 750 |
| 11-14 | 3 | 900 | 3 | 880 |
| 15-17 | 2 | 900 | 2 | 970 |
| 18-21 | 1 | 900 | 1 | 1090 |
| 22-24 | 0.5 | 1200 | 0.5 | 1170 |
| 25-28 | 0.25 | 1200 | 0.25 | 980 |
| 29-31 | 0 | 900 | 0 | 750 |
| 32-35 | 0 | 900/600 | 0 | 500 |
| 36-38 | 0 | 300 | 0 | 250 |

FIG. 20

| Treatment Days (inclusive) | Total Nabilone Dose (mg) | Total Gabapentin Dose (mg) | Total Nabilone Dose (mg) | Total Gabapentin Dose (mg) |
|---|---|---|---|---|
| 1-3 | 6 | 300 | 6 | 300 |
| 4-7 | 5 | 600 | 5 | 600 |
| 8-10 | 4 | 900 | 4 | 900 |
| 11-14 | 3 | 900 | 3.25 | 900 |
| 15-17 | 2 | 900 | 2.25 | 900 |
| 18-21 | 1 | 900 | 1.25 | 1000 |
| 22-24 | 0.5 | 1200 | 0.75 | 900 |
| 25-28 | 0.25 | 900 | 0.5 | 800 |
| 29-31 | 0 | 900 | 0.25 | 800 |
| 32-38 | 0 | 900, 600 | 0 | 800, 400 |
| 39-41 | 0 | 300 | 0 | 200 |

FIG. 21

Cannabis Withdrawal Scale (CWS)

Instructions: This version of the CWS asks about symptoms experienced over the last 24 hours. On Study Days -1 to 5 (Periods 1 and 2) and Study Day 8 (Periods 1 and 2) the subjects will be asked to fill the CWS out multiple times throughout the day, their responses should reflect how they have felt since the last time the questionnaire was completed. The CWS is to be administered by the reviewer.

|   |   | Not at all |   |   |   |   | Moderately |   |   |   | Extremely |
|---|---|---|---|---|---|---|---|---|---|---|---|
| 1 | The only thing I could think about was smoking cannabis | 0 | 1 | 2 | 3 | 4 | 5 | 6 | 7 | 8 | 9 | 10 |
| 2 | I had a headache | 0 | 1 | 2 | 3 | 4 | 5 | 6 | 7 | 8 | 9 | 10 |
| 3 | I had no appetite | 0 | 1 | 2 | 3 | 4 | 5 | 6 | 7 | 8 | 9 | 10 |
| 4 | I felt nauseous (like vomiting) | 0 | 1 | 2 | 3 | 4 | 5 | 6 | 7 | 8 | 9 | 10 |
| 5 | I felt nervous | 0 | 1 | 2 | 3 | 4 | 5 | 6 | 7 | 8 | 9 | 10 |
| 6 | I had some angry outbursts | 0 | 1 | 2 | 3 | 4 | 5 | 6 | 7 | 8 | 9 | 10 |
| 7 | I had mood swings | 0 | 1 | 2 | 3 | 4 | 5 | 6 | 7 | 8 | 9 | 10 |
| 8 | I felt depressed | 0 | 1 | 2 | 3 | 4 | 5 | 6 | 7 | 8 | 9 | 10 |
| 9 | I was easily irritated | 0 | 1 | 2 | 3 | 4 | 5 | 6 | 7 | 8 | 9 | 10 |
| 10 | I had been imagining being stoned | 0 | 1 | 2 | 3 | 4 | 5 | 6 | 7 | 8 | 9 | 10 |
| 11 | I felt restless | 0 | 1 | 2 | 3 | 4 | 5 | 6 | 7 | 8 | 9 | 10 |
| 12 | I woke up early | 0 | 1 | 2 | 3 | 4 | 5 | 6 | 7 | 8 | 9 | 10 |
| 13 | I had a stomachache | 0 | 1 | 2 | 3 | 4 | 5 | 6 | 7 | 8 | 9 | 10 |
| 14 | I had nightmares and/or strange dreams | 0 | 1 | 2 | 3 | 4 | 5 | 6 | 7 | 8 | 9 | 10 |
| 15 | Life seemed like an uphill struggle | 0 | 1 | 2 | 3 | 4 | 5 | 6 | 7 | 8 | 9 | 10 |
| 16 | I woke up sweating at night | 0 | 1 | 2 | 3 | 4 | 5 | 6 | 7 | 8 | 9 | 10 |
| 17 | I had trouble getting to sleep at night | 0 | 1 | 2 | 3 | 4 | 5 | 6 | 7 | 8 | 9 | 10 |
| 18 | I felt physically tense | 0 | 1 | 2 | 3 | 4 | 5 | 6 | 7 | 8 | 9 | 10 |
| 19 | I had hot flashes | 0 | 1 | 2 | 3 | 4 | 5 | 6 | 7 | 8 | 9 | 10 |

Score by summing each item's value to a maximum withdrawal score of 190.

FIG. 22

Withdrawal Bothersomeness Scale (WBS)
This version of the CWS asks about how bothered a subject is by withdrawal symptoms over the past 24 hours. On Study Days -1 to 5 (Periods 1 and 2) and Study Day 8 (Periods 1 and 2), the subjects will be asked to fill the CWS out multiple times throughout the day. Their responses should reflect how they have felt since the last time the questionnaire was completed.

Please check the response that best described how Bothered you are by each symptom since you last completed this questionnaire.

| | | Not Bothered at All | Mildly Bothered | Moderately Bothered | Severely Bothered | Very Severely Bothered |
|---|---|---|---|---|---|---|
| 1 | The only thing I could think about was smoking cannabis | | | | | |
| 2 | I had a headache | | | | | |
| 3 | I had no appetite | | | | | |
| 4 | I felt nauseous (like vomiting) | | | | | |
| 5 | I felt nervous | | | | | |
| 6 | I had some angry outbursts | | | | | |
| 7 | I had mood swings | | | | | |
| 8 | I felt depressed | | | | | |
| 9 | I was easily irritated | | | | | |
| 10 | I had been imagining being stoned | | | | | |
| 11 | I felt restless | | | | | |
| 12 | I woke up early | | | | | |
| 13 | I had a stomachache | | | | | |
| 14 | I had nightmares and/or strange dreams | | | | | |
| 15 | Life seemed like an uphill struggle | | | | | |
| 16 | I woke up sweating at night | | | | | |
| 17 | I had trouble getting to sleep at night | | | | | |
| 18 | I felt physically tense | | | | | |
| 19 | I had hot flashes | | | | | |

FIG. 23

11-item Cannabis Withdrawal Questionnaire (CWQ)

|   |   | Not at all | | | | | Moderately | | | | | Extremely |
|---|---|---|---|---|---|---|---|---|---|---|---|
| 1 | I am having difficulty concentrating | 0 | 1 | 2 | 3 | 4 | 5 | 6 | 7 | 8 | 9 | 10 |
| 2 | I feel calm | 0 | 1 | 2 | 3 | 4 | 5 | 6 | 7 | 8 | 9 | 10 |
| 3 | I feel awful | 0 | 1 | 2 | 3 | 4 | 5 | 6 | 7 | 8 | 9 | 10 |
| 4 | I am having strange thoughts | 0 | 1 | 2 | 3 | 4 | 5 | 6 | 7 | 8 | 9 | 10 |
| 5 | I have chills | 0 | 1 | 2 | 3 | 4 | 5 | 6 | 7 | 8 | 9 | 10 |
| 6 | I have body aches and pains | 0 | 1 | 2 | 3 | 4 | 5 | 6 | 7 | 8 | 9 | 10 |
| 7 | I am difficulty thinking clearly | 0 | 1 | 2 | 3 | 4 | 5 | 6 | 7 | 8 | 9 | 10 |
| 8 | I feel high | 0 | 1 | 2 | 3 | 4 | 5 | 6 | 7 | 8 | 9 | 10 |
| 9 | I feel confused | 0 | 1 | 2 | 3 | 4 | 5 | 6 | 7 | 8 | 9 | 10 |
| 10 | I feel paranoid | 0 | 1 | 2 | 3 | 4 | 5 | 6 | 7 | 8 | 9 | 10 |
| 11 | I am having trouble remembering things | 0 | 1 | 2 | 3 | 4 | 5 | 6 | 7 | 8 | 9 | 10 |

FIG. 24

Sleep Questionnaire

This questionnaire is to be administered each morning and assesses problems that affected the quality and amount of sleep from the previous night and wakefulness each morning.

This questionnaire refers to your sleep over the past 24 hours. Please try and answer every question.

Name: _____  Today's date: __/__/____

At what time did you:

1. Settle down for the night?           ___ Hrs.  ___ Mins.
2. Fall asleep last night?              ___ Hrs.  ___ Mins.
3. Finally wake this morning?           ___ Hrs.  ___ Mins.
4. Get up (out of bed) this morning?    ___ Hrs.  ___ Mins.
5. Was your sleep: (tick box)
    1. Very light    ☐
    2. Light         ☐
    3. Average       ☐
    4. Deep          ☐
    5. Very deep     ☐

6. How many times did you wake up? (tick box)
    1. Not at all            ☐
    2. Not sure              ☐
    3. Once                  ☐
    4. Twice                 ☐
    5. Three times           ☐
    6. Four times            ☐
    7. More than five times  ☐

7. Approximately how much sleep did you have?
    Last night?                ___ Hrs.  ___ Mins.
    During the day, yesterday? ___ Hrs.  ___ Mins.

FIG. 24 (Continued)

8. How well did you sleep last night? (tick box)
   1. Very badly ☐
   2. Badly ☐
   3. Fairly badly ☐
   4. Fairly well ☐
   5. Well ☐
   6. Very well ☐

| My Sleep last night….. | Strongly Disagree | Disagree | Somewhat | Agree | Strongly Agree |
|---|---|---|---|---|---|
| 1. My sleep was restless | | | | | |
| 2. I was satisfied with my sleep | | | | | |
| 3. My sleep was refreshing | | | | | |
| 4. I had difficulty falling asleep | | | | | |
| 5. I had trouble staying asleep | | | | | |
| 6. I had trouble sleeping | | | | | |
| 7. I got enough sleep | | | | | |
| 8. I felt anxious before going to bed | | | | | |
| 9. I felt clammy/had sweats before | | | | | |
| 10. I did not dream | | | | | |
| 11. I had more vivid dreams | | | | | |
| 12. I had nightmares | | | | | |

FIG. 25

Patient Global Impression of Severity (PGI-S)

Please choose the response below that best describes the severity of your cannabis withdrawal symptoms*:

| None | Mild | Moderate | Severe | Very Severe |
|------|------|----------|--------|-------------|
| ☐ | ☐ | ☐ | ☐ | ☐ |

*Site will have reviewed possible symptoms of withdrawal as part of instructions for responding to questionnaires*

If you checked mild, moderate or severe or very severe, how bothered are you by your symptoms?

| Not at all | Somewhat bothered | Moderately bothered | Very much bothered |
|------------|-------------------|---------------------|--------------------|
| ☐ | ☐ | ☐ | ☐ |

FIG. 26

Clinician Global Impression (CGI)

Considering your total clinical experience with people with withdrawal symptoms, does the subject seem to be exhibiting withdrawal symptoms now?

| Not Assessed | Not At All | Mild Symptoms | Moderately Symptomatic | Severely Symptomatic |
|---|---|---|---|---|
| ☐ | ☐ | ☐ | ☐ | ☐ |

METHODS AND COMPOSITIONS FOR TREATING CANNABIS USE DISORDER AND MITIGATING CANNABINOID WITHDRAWAL

CROSS-REFERENCE TO RELATED APPLICATIONS

This application is a continuation of U.S. Non-provisional application Ser. No. 17/244,585, filed on Apr. 29, 2021, which is a continuation-in-part of International Appl. No.: PCT/US2021/020921, filed on Mar. 4, 2021, which claims the benefit of U.S. Provisional Appl. No. 62/985,097, filed on Mar. 4, 2020, the contents of which are hereby incorporated by reference in their entireties.

FIELD OF THE INVENTION

The field of this invention generally relates to the fields of drug abuse and addiction. In particular, the field of the invention relates to compositions and methods for treating cannabis use disorder and mitigating one or more symptoms of cannabis withdrawal.

BACKGROUND

Cannabis is the most widely used illicit drug in the world and causes multiple health and societal problems. Approximately 48.2 million people in the US used cannabis in 2019 with use increasing over the past several years ("Key Substance Use and Mental Health Indicators in the United States: Results from the 2019 National Survey on Drug Use and Health," SAMHSA, 2019). It has been estimated that 22 to 44% of frequent cannabis users will develop cannabis use disorder (CUD) (Leung et al., *Addict Behav* 109:106479 (2020)) and that in 2019 approximately 4.8 million people were diagnosed with CUD (SAMHSA, 2019).

Cannabis use has been associated with an increased risk of health problems including cognitive issues, psychosis, cardiovascular and pulmonary disorders, and cannabis dependence accounts for approximately 20% of hospitalizations for addiction (NIDA, 2017). Most recently pre-term birth (Corsi et al., *JAMA* 322(2):145-152 (2019)) and infant death have been associated with cannabis use. A recent report stated that the highest use ever reported for cannabis was found from a survey from the University of Michigan among college students age 18 to 22. Accelerating legalization of medical and recreational marijuana leading to increased availability and potency are expected to increase the population of cannabis users who experience withdrawal symptoms. The frequency and potency of cannabis use have increased leading to greater tolerance and dependency and a need for agents to help those individuals who wish to decrease or discontinue cannabis. However, there are currently no approved agents to aid patients with their withdrawal symptoms as they may attempt to discontinue cannabis. Standard treatment of opioid addiction includes mitigating withdrawal symptoms, and recently has included cannabis treatment. Discontinuing cannabis may also lead to withdrawal symptoms for which a treatment should be available.

Cannabis withdrawal syndrome may occur in those with CUD who attempt to discontinue cannabis. Long term and regular use of cannabis has been associated with significant symptoms that include irritability, anger, aggression, anxiety, nervousness, sleep difficulties, decreased appetite, and depressed mood. Additionally, physical symptoms that cause discomfort include abdominal pain, nausea, fever/chills, sweats and headache. Acute symptoms may occur within 24 hours of discontinuation and last up to one month (Bonnet and Preuss, *Subst Abuse Rehabil* 8:9-37 (2017)). Chronic symptoms including cravings and sleep disorders have been reported and may last for approximately 45 days (SAMHSA, 2018). Additionally, although not included in the Diagnostic and Statistical Manual of Mental Disorders (DSM)-5 definition of CWS, cravings for cannabis is an important factor in preventing sustained discontinuation. Chronic cannabis smoking can lead to tolerance and withdrawal symptoms.

Chronic cannabis use has been associated with the down-regulation of brain cannabinoid 1 (CB1) receptors (Brezing and Levin, *Neuropsychopharmacology* 43(1):173-194 (2018)). Downregulation of the CB1 receptor has been demonstrated to be reversible by 4 weeks of abstinence (Hirvonen et al., *Mol Psychiatry* 17(6):642-649 (2012)). Therefore, reducing withdrawal symptoms with the final drug product may aid in decreasing cannabis recidivism by permitting upregulation of CB1 receptors.

Existing studies attempting to mitigate cannabis withdrawal syndrome and CUD have yielded disappointing results. Many studies have failed to distinguish withdrawal symptoms from a decrease in frequency and potency of use and/or abstinence, making assessment of treatment successes and failures quite difficult, leaving patients to fend for themselves or recidivate. Psychosocial approaches such as cognitive behavioral therapy have an 80% failure rate as early as 1 month. Medication trials have shown mixed results for the treatment of withdrawal symptoms. The withdrawal experienced during cannabis discontinuation in patients with CUD may not, in and of itself be life-threatening, however the extent of morbidity, preterm birth, lost workdays, relationship issues, depression, and suicidality in those suffering psychosis have not been well characterized in those suffering withdrawal symptoms. Failure to minimize/discontinue cannabis due to the aversive experience of cannabis withdrawal syndrome prevents patients from achieving abstinence. There is an urgent need for new treatments for cannabis use disorder and mitigating cannabis withdrawal symptoms.

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

In one aspect, the invention provides a method of treating cannabis use disorder in a subject, comprising administering to the subject in need thereof:
  i) an effective amount of a cannabinoid; and
  ii) an effective amount of a second active agent.

In some embodiments, a method of treating cannabis use disorder comprises administering (a) a cannabinoid, such as cannabidiol (CBD), nabilone, or a combination of CBD and nabilone and (b) a second active agent. In some embodiments, a method of treating cannabis use disorder comprises administering (a) a combination of CBD and nabilone and (b) a second active agent selected from gabapentin and pregabalin. In some embodiments, a method of treating cannabis use disorder comprises administering (a) a combination of CBD and nabilone and (b) gabapentin or pregabalin.

In one aspect, the invention provides a method of treating cannabis use disorder in a subject, comprising administering to the subject in need thereof:
  i) an effective amount of a cannabinoid;
  wherein the cannabinoid comprises at least one of a nabilone or a cannabidiol. In some embodiments, the method comprises administering at least one of a nabilone and a cannabidiol. In some embodiments, the method comprises concurrently administering to a subject a first composition comprising nabilone and a second composition comprising CBD. In some embodiments, the me comprises sequentially administering to a subject a first composition comprising nabilone and a second composition comprising CBD.

In one aspect, the invention provides a method of treating cannabis use disorder in a subject, comprising administering to the subject in need thereof:
  i) an effective amount of a cannabinoid; and
  ii) an effective amount of gabapentin or a gabapentin analog.

In some embodiments, a method of treating cannabis use disorder comprises administering (a) a cannabinoid, such as cannabidiol (CBD), nabilone, or a combination of CBD and nabilone and (b) gabapentin or a gabapentin analog. In some embodiments, a method of treating cannabis use disorder comprises administering (a) a combination of CBD and nabilone and (b) gabapentin or a gabapentin analog. In some embodiments, a method of treating cannabis use disorder comprises administering (a) a combination of CBD and nabilone and (b) gabapentin or pregabalin.

In one aspect, the invention provides a method of mitigating one or more symptoms of cannabinoid withdrawal in a subject, comprising administering to the subject in need thereof:
  i) an effective amount of a cannabinoid; and
  ii) an effective amount of a second active agent.

In some embodiments, a method of mitigating one or more symptoms of cannabinoid withdrawal comprises administering (a) a cannabinoid, such as cannabidiol (CBD), nabilone, or a combination of CBD and nabilone and (b) a second active agent. In some embodiments, a method of mitigating one or more symptoms of cannabinoid withdrawal comprises administering (a) a combination of CBD and nabilone and (b) a second active agent selected from gabapentin and a gabapentin analog. In some embodiments, a method of mitigating one or more symptoms of cannabinoid withdrawal comprises administering (a) a combination of CBD and nabilone and (b) gabapentin or pregabalin.

In another aspect, the invention provides a method of mitigating one or more symptoms of cannabinoid withdrawal in a subject, comprising administering to the subject in need thereof i) an effective amount of a cannabinoid; wherein the cannabinoid comprises at least one of a nabilone or a cannabidiol. In some embodiments, the method comprises administering at least one of a nabilone and a cannabidiol. In some embodiments, the method comprises concurrently administering to a subject a first composition comprising nabilone and a second composition comprising CBD. In some embodiments, the method comprises sequentially administering to a subject a first composition comprising nabilone and a second composition comprising CBD. Surprisingly, compositions of the invention can be administered once daily, preferably in the evening, such as administration after dinner or just before bed. Once daily compositions of the invention may be formulated for extended, delayed and/or sustained release.

In another aspect, the invention provides a method of mitigating one or more symptoms of cannabinoid withdrawal in a subject, comprising administering to the subject in need thereof:
  i) an effective amount of a cannabinoid; and
  ii) an effective amount of gabapentin or a gabapentin analog.

In some embodiments a method of mitigating one or more symptoms of cannabinoid withdrawal comprises administering (a) a cannabinoid such as cannabidiol (CBD), nabilone, or a combination of CBD and nabilone and (b) gabapentin or a gabapentin analog. In some embodiments, a method of mitigating one or more symptoms of cannabinoid withdrawal comprises administering (a) a combination of CBD and nabilone and (b) gabapentin or a gabapentin analog.

In some embodiments, a method of mitigating one or more symptoms of cannabinoid withdrawal comprises administering (a) a combination of CBD and nabilone and (b) gabapentin or pregabalin.

In some embodiments, the cannabinoid and/or second active agent is administered in the form of a pharmaceutically acceptable salt. In some embodiments, the cannabinoid is combination of CBD, or a pharmaceutically acceptable salt thereof, and nabilone, or a pharmaceutically acceptable salt thereof. In some embodiments, the second active agent is a pharmaceutically acceptable salt of gabapentin or a gabapentin analog.

In some embodiments, the subject is administered a composition comprising a cannabinoid. In some embodiments composition comprises a cannabinoid such as cannabidiol (CBD), nabilone, or a combination of CBD and nabilone. In some embodiments, the composition comprises a combination of CBD and nabilone. In some embodiments, the subject is administered a first composition comprising CBD and a second composition comprising nabilone. In some embodiments, the subject is administered a first composition comprising CBD as the sole cannabinoid in the composition and a second composition comprising nabilone as the sole cannabinoid in the composition.

In some embodiments, the subject is administered a composition comprising the cannabinoid and gabapentin or gabapentin analog. In some embodiments composition comprises (a) a cannabinoid such as cannabidiol (CBD), nabilone, or a combination of CBD and nabilone and (b) gabapentin or a gabapentin analog. In some embodiments, the composition comprises (a) a combination of CBD and nabilone and (b) gabapentin or a gabapentin analog. In some embodiments, a composition comprises (a) a combination of CBD and nabilone and (b) gabapentin or pregabalin.

In some embodiments, the composition is administered orally.

In some embodiments, the cannabinoid and gabapentin or gabapentin analogs are administered in separate compositions. In some embodiments in which the cannabinoid comprises two or more cannabinoids, such as CBD or nabilone in combination with another cannabinoid or each other, the two or more cannabinoids may be administered in separate compositions.

In some embodiments, the composition comprising gabapentin or gabapentin analog is administered orally.

In some embodiments, the composition comprising the cannabinoid is administered orally. In some embodiments, the orally administered composition comprises CBD, nabilone, or a combination of CBD and nabilone.

In some embodiments, the cannabinoid is selected from the group consisting of Δ9-tetrahydrocannabinol (THC), Δ8-tetrahydrocannabinol, 11-OH-delta-9-THC, (+)-1,1-dimethylheptyl analog of 7-hydroxy-delta-6-tetrahydrocannabinol, dodeca-2E,4E,8Z,10E/Z-tetraenoic-acid-isobutyl-amides, cannabinol (CBN), tocannabicyclol (CBL), cannabidivarin (CBDV), cannabidiolic acid (CBDA), cannabichromevarin (CBCV), cannabigerovarin (CBGV), cannabidiol (CBD), cannabichromene (CBC), tetrahydrocannabivarin (THCV), cannabigerol (CBG), cannabigerol monomethyl ether (CBGM), 3-(5'-cyano-1',1'-dimethylpentyl)-1-(4-N-morpholinobutyryloxy) Δ8-tetrahydrocannabinol hydrochloride], dexanabinol, nabilone (6aR,10aR)-1-hydroxy-6,6-dimethyl-3-(2-methyloctan-2-yl)-7,8,10,10a-tetrahydro-6aH-benzo[c]chromen-9-one), levonantradol, or N-(2-hydroxyethyl)hexadecanoamide and combinations thereof. In some embodiments, the cannabinoid that is used is isolated and purified from *Cannabis sativa* and comprises a mixture of cannabinoids.

In some embodiments, gabapentin or a gabapentin analog is an agent that binds with high affinity to the alpha-2-delta ($\alpha_2\delta$) subunit of voltage-activated calcium channels, especially those agents known to mitigate cravings. In some embodiments, a gabapentin analog may be selected from the group consisting of pregabalin, 3-methyl gabapentin, [(1R,5R,6S)-6-(Aminomethyl)bicyclo[−3.2.0]hept-6-yl]acetic acid, 3-(1-Aminomethyl-cyclohexylmethyl)-4H-[1,2,4]-oxadiazol-5-one, C-[1-(1H-Tetrazol-5-ylmethyl)-cycloheptyl]-methylamine, (3S,4S)-(1-Aminomethyl-3,4-dimethyl-cyclopentyl)-acetic acid, (1α,3α,5α)(3-amino-methyl-bicyclo[3.2.0]hept-3-yl)-acetic acid, (3S,5R)-3-Aminomethyl-5-methyl-octanoic acid, (3S,5R)-3-amino-5-methyl-heptanoic acid, (3S,5R)-3-amino-5-methyl-nonanoic acid and (3S,5R)-3-Amino-5-methyl-octanoic acid, (1-aminomethyl-3-methylcyclohexyl)acetic acid, (1-aminomethyl-3-methylcyclopentyl)acetic acid, (S)-3-(aminomethyl)-5-methylhexanoic acid, 3-aminomethyl-5-methyl-hexanoic acid, and (1-aminomethyl-3,4-dimethylcyclopentyl)acetic acid.

In some embodiments, the subject is administered a dosage of the cannabinoid that is tapered over a period of time.

In some embodiments, the subject is administered a dosage of the second active agent that is titrated with an increasing dose for a period of time.

In some embodiments, the subject is administered a dosage of second active agent that is maintained for a period of time following the titration.

In some embodiments, the subject is administered a dosage of second active agent that is tapered for a period of time following the administration of the dosage that is maintained for a period of time.

In some embodiments, the administration of cannabinoid is discontinued after a period of time.

In some embodiments, the administration of second active agent is discontinued after a period of time.

Other objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 19. Exemplary titration and tapering schedule with a combination of gabapentin and nabilone.

FIG. 20. Exemplary titration and tapering schedule with a combination of gabapentin and nabilone.

FIG. 21. *Cannabis* Withdrawal Scale (CWS).

FIG. 22. Withdrawal Bothersomeness Scale (WBS).

FIG. 23. 11-item *Cannabis* Withdrawal Questionnaire (CWQ).

FIG. 24. Sleep questionnaire.

FIG. 25. Patient Global Impression of Severity scale (PGI-S).

FIG. 26. Clinician global impression scale (CGI).

DETAILED DESCRIPTION OF THE INVENTION

Figure 1:
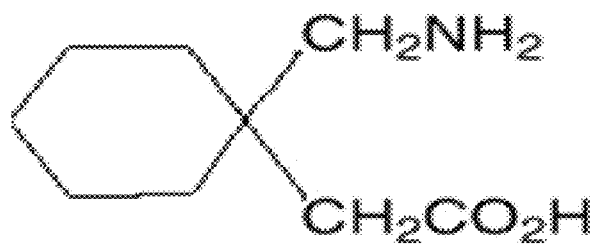
FIG. 1 provides the chemical structure of gabapentin (1-(aminomethyl)cyclohexaneacetic acid).

The present invention is directed to compositions and methods for treating *cannabis* use disorder and mitigating one or more cannabinoid withdrawal symptoms.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

Unless defined otherwise, all technical and scientific terms used herein have the same meaning as commonly understood by those of ordinary skill in the art to which this invention pertains. The following references provide one of skill with a general definition of many of the terms used in this invention: The Diagnostic and Statistical Manual of Mental Disorders (5th ed.; DSM-5; American Psychiatric Association, 2013); Academic Press Dictionary of Science and Technology, Morris (Ed.), Academic Press (1st ed., 1992); Dictionary of Pharmaceutical Medicine, Nahler (Ed.), Springer-Verlag Telos (1994); Dictionary of Organic Chemistry, Kumar and Anandand (Eds.), Anmol Publications Pvt. Ltd. (2002); and A Dictionary of Biology (Oxford Paperback Reference), Martin and Hine (Eds.), Oxford University Press (4th ed., 2000).

As used herein, the term "about" means plus or minus 10% of the numerical value of the number with which it is being used.

In one embodiment, the invention provides a method of treating *cannabis* use disorder in a subject, comprising administering to the subject in need thereof:
  i) an effective amount of a cannabinoid; and
  ii) an effective amount of gabapentin or a gabapentin analog.

In another embodiment, the invention provides a method of mitigating one or more symptoms of cannabinoid withdrawal in a subject, comprising administering to the subject in need thereof:
  i) an effective amount of a cannabinoid; and
  ii) an effective amount of gabapentin or a gabapentin analog.

*Cannabis* use disorder is the continued use of a substance that delivers one or more natural and/or synthetic cannabinoids despite clinically significant distress or impairment. In some embodiments, *cannabis* use disorder can be either mild, moderate, or severe. In accordance with the DSM-V, *cannabis* use disorder can be classified as 1) mild if 2-3 of the criteria below are present; 2) moderate if 4-5 criteria below are present; or 3) severe if 6 or more criteria below are present.

DSM-V Criteria
1. Substance is often taken in larger amounts and/or over a longer period than the patient intended.
2. Persistent attempts or one or more unsuccessful efforts made to cut down or control substance use.
3. A great deal of time is spent in activities necessary to obtain the substance, use the substance, or recover from effects.
4. Craving or strong desire or urge to use the substance.
5. Recurrent substance use resulting in a failure to fulfill major role obligations at work, school, or home.
6. Continued substance use despite having persistent or recurrent social or interpersonal problem caused or exacerbated by the effects of the substance.
7. Important social, occupational or recreational activities given up or reduced because of substance use.
8. Recurrent substance use in situations in which it is physically hazardous.
9. Substance use is continued despite knowledge of having a persistent or recurrent physical or psychological problem that is likely to have been caused or exacerbated by the substance.
10. Tolerance, as defined by either of the following:
    a. Markedly increased amounts of the substance in order to achieve intoxication or desired effect;
    b. Markedly diminished effect with continued use of the same amount;
11. Withdrawal, as manifested by either of the following:
    a. The characteristic withdrawal syndrome for the substance;
    b. The same (or a closely related) substance is taken to relieve or avoid withdrawal symptoms.

In some embodiments, withdrawal symptoms for cannabinoids can include one or more of the following that develop within 1 week after abrupt reduction or the cessation of prolonged *cannabis*/cannabinoid use: (1) irritability, anger, or aggression; (2) nervousness or anxiety; (3) sleep difficulty (e.g., insomnia or vivid dreaming); (4) decreased appetite or weight loss; (5) restlessness; (6) depressed mood; and (7) at least one of the following physical symptoms that causes discomfort: abdominal pain, shakiness/tremors, sweating, fever, chills, or headache; and (8) cravings for the cannabinoid(s) substance. Withdrawal symptoms can also include elevated evening cortisol levels. Withdrawal symptoms can further cause clinically significant distress or impairment in social, occupational, or other important areas of functioning. See DSM V *Cannabis* Withdrawal Syndrome Diagnostic Criteria.

As used herein, the term "second active agent" means a pharmaceutical or biological agent other than nabilone that assists or mediates positive effects in the treatment of one or more symptoms of *cannabis* withdrawal syndrome, including, without limitation, reducing cravings in a subject, including marijuana-related and/or THC-related cravings, improving sleep quality, reducing stress or anxiety, depressed mood or other. Second active agents can include pregabalin, gabapentin, gabapentin analogs, GABA analogs, and GABAergic agents.

As used herein, the term "GABAergic agents" are pharmaceutical or biological agents that have the same or similar pharmacologic activity as gabapentin.

The terms "treatment," "treating" or "mitigating" as used herein refers to partially or completely alleviating, inhibiting, ameliorating and/or relieving *cannabis* use disorder or cannabinoid withdrawal. The improvement may be any observable or measurable improvement. Thus, one of skill in the art realizes that a treatment may improve the patient's condition but may not be a complete cure of the condition or disorder.

In accordance with the invention, a "therapeutically effective amount" or "effective amount" of a cannabinoid and a second active agent such as gabapentin or a gabapentin analog is administered to the subject. As used herein a "therapeutically effective amount" or "effective amount" is an amount sufficient to alleviate, inhibit, ameliorate and/or relieve one or more symptoms or criteria associated with *cannabis* use disorder or cannabinoid withdrawal.

The term "subject" as used herein is not limiting and is used interchangeably with patient. In some embodiments, the subject is a mammal. For example, mammals contemplated include humans, primates, dogs, cats, sheep, cattle, goats, pigs, horses, chickens, mice, rats, rabbits, guinea pigs, and the like. In some embodiments, the subject is a human. In some embodiments, the subject has a substance dependence on one or more cannabinoids, is suspected to have substance dependence or is at risk of developing substance dependence.

Cannabinoids

In accordance with the invention, an effective amount of a cannabinoid is administered to the subject. Cannabinoid as used herein can comprise a single cannabinoid or a combination of cannabinoids. Cannabinoids are chemical compounds that act directly and indirectly on cannabinoid receptor. The cannabinoid or cannabinoids that can be used in the invention are not necessarily limiting. One skilled in the art will appreciate that the present invention is applicable to the class of pharmaceutically acceptable cannabinoids. For purposes of the present invention, the term "cannabinoid" includes naturally occurring cannabinoids and non-natural derivatives of cannabinoids which can be obtained by derivation of natural cannabinoids. In other words, the cannabinoid used in the compositions and methods of the invention may be natural, semi-synthetic, or synthetic. The cannabinoid may be included in its free form, or in the form of a salt; an acid addition salt of an ester; an amide; an enantiomer; an isomer; a tautomer; a prodrug; a derivative of an active agent of the present invention; different isomeric forms (for example, enantiomers and diastereoisomers), both in pure form and in admixture, including racemic mixtures; enol forms. The term "cannabinoid" is also meant to encompass derivatives that are produced from another compound of similar structure by the replacement of, e.g., substitution of one atom, molecule or group by another such as 11-hydroxy-delta-8-tetrahydrocannabinol and 11-hydroxy-delta-9-tetrahydrocannabinol. An example of a suitable prodrug is THC-hemisuccinate.

The term "cannabinoid" is further meant to encompass natural cannabinoids that have been purified or modified, and synthetically derived cannabinoids, for example, United States Patent Application Publication No. 2005/0266108, hereby incorporated by reference in its entirety, describes a method of purifying cannabinoids obtained from plant material. The term cannabinoid is also meant to include the compounds described in U.S. Pat. No. 6,713,048, which is herein incorporated by reference, including levonantradol, (−)-HU-210, Win 55212-2, Anandamide, Methandamide, CP 55940, O-1057, SR 141716A, etc.

In some embodiments, the cannabinoid is selected from the group consisting of Δ9-tetrahydrocannabinol (THC), Δ8-tetrahydrocannabinol, 11-OH-delta-9-THC, (+)-1,1-dimethylheptyl analog of 7-hydroxy-delta-6-tetrahydrocannabinol, dodeca-2E,4E,8Z,10E/Z-tetraenoic-acid-isobutyl-amides, cannabinol (CBN), tocannabicyclol (CBL), cannabidivarin (CBDV), cannabidiolic acid (CBDA), cannabichromevarin (CBCV), cannabigerovarin (CBGV), cannabidiol (CBD), cannabichromene (CBC), tetrahydrocannabivarin (THCV), cannabigerol (CBG), cannabigerol monomethyl ether (CBGM), 3-(5'-cyano-1',1'-dimethylpentyl)-1-(4-N-morpholinobutyryloxy) Δ8-tetrahydrocannabinol hydrochloride], dexanabinol, nabilone (6aR,10aR)-1-hydroxy-6,6-dimethyl-3-(2-methyloctan-2-yl)-7,8,10,10a-tetrahydro-6aH-benzo[c]chromen-9-one), levonantradol, or N-(2-hydroxyethyl)hexadecanoamide and combinations thereof. In some embodiments, the cannabinoid that is used is isolated and purified from *Cannabis sativa* and comprises a mixture of cannabinoids.

In some embodiments, the cannabinoid comprises dronabinol hemisuccinate ester (THC-HS).

In some embodiments, the cannabinoid comprises or consists essentially of Delta-9-tetrahydrocannabinol, also known as dronabinol. Dronabinol is naturally-occurring and has been extracted from *Cannabis sativa* (marijuana). It has also been produced chemically as described in U.S. Pat. No. 3,668,224. Dronabinol is a light-yellow resinous oil that is sticky at room temperature but it hardens upon refrigeration. It turns to a flowable liquid when heated at higher temperatures. Dronabinol is insoluble in water. It has a pKa of 10.6 and an octanol-water partition coefficient: 6,000:1 at pH 7. Dronabinol is available in natural (extracted from plant) and synthetic forms. On the other hand, synthetic dronabinol may be utilized and may be synthesized using the starting materials Olivetol and p-2,8-menthadien-2-ol (PMD).

The term "dronabinol" is further meant to encompass naturally occurring dronabinol, metabolites, synthetically derived dronabinol, and synthetically modified dronabinol starting with a molecule obtained from a natural source for example, United States Patent Application Publication No. 2005/0171361, hereby incorporated by reference in its entirety, describes a method of extracting delta-9-THC acid from the plant material by chromatography and then synthetically converting it to dronabinol.

In some embodiments, the cannabinoid comprises or consists essentially of nabilone. Nabilone is a synthetic cannabinoid. Nabilone (Cesamet®) is a Food and Drug Administration (FDA) approved synthetic tetrahydrocannabinol (THC) similar to delta-9-tetrahydrocannabinol (49 THC) that is used to treat chemotherapy-induced nausea and vomiting with maximum recommended dosing of 6 mg/day in divided doses (Cesamet Prescribing Information).

Figure 2:
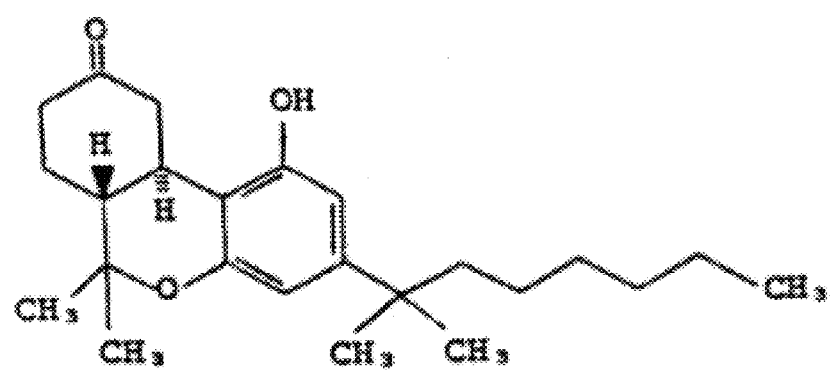
FIG. 2 provides the chemical structure of nabilone ((±)-trans-3-(1,1-dimethylheptyl)6,6a,7,8,10,10a-hexahydro-1-hydroxy-6-6-dimethyl-9H-dibenzo[b,d]pyran-9-one).

Nabilone as a raw material occurs as a white to off-white polymorphic crystalline powder. In aqueous media, the solubility of nabilone is less than 0.5 mg/L, with pH values ranging from 1.2 to 7.0. Chemically, nabilone is similar to the active ingredient found in naturally occurring *Cannabis sativa* L. [Marijuana; delta-9-tetrahydrocannabinol (delta-9-THC)]. Nabilone is (±)-trans-3-(1,1-dimethylheptyl)-6,6a,7,8,10,10a-hexahydro-1-hydroxy-6-6-dimethyl-9H-dibenzo[b,d]pyran-9-one and has the empirical formula $C_{24}H_{36}O_3$. It has a molecular weight of 372.55. The chemical structure is shown in FIG. 2.

In some embodiments, the cannabinoid used is esterified. Esterified forms of THC are described in U.S. Pat. No. 4,933,368 and in U.S. Pat. No. 5,389,375. Other useful polar esters are the hemi-ester of malonic acid and the alaninate ester of alanine. It has been reported, e.g., in U.S. Pat. Nos. 5,508,051 and 5,389,375, that salts of the terminal carboxylic acid group of the ester, for example, the N-methyl glutamine salt as well as the sodium and potassium salts are also useful. The descriptions of U.S. Pat. Nos. 4,933,368; 5,508,037; and 5,389,375, are incorporated herein by reference. These ester compounds are hydrolyzed in the blood stream releasing THC to provide a high degree of bioavailability of THC without regard to patient conditions and anomalies.

Oral THC is subject to the first-pass effect resulting in heavy metabolism with production of high levels of 11-OH-delta-9-THC. It is reported that this 11-hydroxy metabolite is more potent agonist than delta-9-THC.

THC obtained by any means can be esterified by the reaction of THC with an organic acid, an organic acid halide or preferably organic acid anhydride in the presence of 4-amino-substituted pyridine alone or in admixture with an organic amine, or in any other manner known to those skilled in the art. U.S. Pat. No. 6,008,383, hereby incorporated by reference, describes a process for converting dronabinol to a variety of ester analogs, which process is said to be economical and efficient. Therein, dronabinol is esterified by reaction with a carboxylic acid, an acid halide or an acid anhydride in the presence of a 4-aminopyridine either alone or in admixture with an organic amine such as a mono-, di-, or tri-alkyl amine.

Cannabinoid as used herein can comprise a single cannabinoid or a combination of cannabinoids. In some embodiments, CBD is used. In some embodiments, nabilone is used. In some embodiments nabilone and CBD are used in combination.

Gabapentin and Analogs

In some embodiments, the second active agent is gabapentin or an analog thereof and an effective amount of gabapentin or a gabapentin analog is administered to the subject.

As used herein "gabapentin" refers to the chemical compound 1-aminomethyl)-1-cyclohexaneacetic acid. Gabapentin is sold under the trademark NEURONTIN for the treatment of partial seizures in adults with epilepsy. Gabapentin is also indicated for management of postherpetic neuralgia in adults It is useful in therapy of certain cerebral disorders such as certain forms of epilepsy, faintness attacks, hypokinesia and cranial traumas.

Gabapentin is an alkylated analog of gamma butyric acid (GAB A) and is approved by the FDA for the management of epileptic seizures and neuropathic pain (Neurontin Prescribing Information).

U.S. Pat. Nos. 4,024,175 and 4,087,544 describe the compound and some of its uses. They also disclose an acid salt, i.e. gabapentin hydrochloride hydrate in a ratio of 4:4:1 and a sodium salt of gabapentin hydrate in a ratio of 2:1. These patents are hereby incorporated by reference. Since becoming a generic drug in 2004, gabapentin has been marketed under other brand names. Gabapentin is commonly packaged in an oral pill or an oral liquid solution.

Gabapentin was initially synthesized to mimic the chemical structure of the neurotransmitter gamma-aminobutyric acid (GABA), and it in fact has a similar chemical structure to GABA. However, gabapentin has not been shown to bind to GABA receptors at concentrations at or below 1 millimolar. Gabapentin modulates the action of glutamate decarboxylase (GAD) and branched chain aminotransferase (BCAT), two enzymes involved in GABA biosynthesis, which may have an effect on GABA biosynthesis and/or GABA concentration.

Pregabalin is a long-acting form of gabapentin with the formula (S)-3-(aminomethyl)-5-methyl-hexanoic acid and CAS Registry Number: 148553-50-8, CI 1008. The compounds are described in U.S. Pat. Nos. 5,608,090 and 5,599,973, the disclosures of which are incorporated herein by reference to show additional forms of gabapentin usable in this invention.

The second active agent can be in free form, or in the form of a salt; an acid addition salt of an ester; an amide; an enantiomer; an isomer; a tautomer; a prodrug; different isomeric forms (for example, enantiomers and diastereoisomers), both in pure form and in admixture, including racemic mixtures. The structure of gabapentin is shown in FIG. 1.

The term "analog" is used herein to refer to a molecule that structurally and/or functionally resembles a reference molecule (e.g., gabapentin) but which has been modified in a targeted and controlled manner, by replacing a specific substituent of the reference molecule with an alternate substituent. A "gabapentin analog" as used in this disclosure refers to a compound sharing a core structure with gabapentin and that can compete with gabapentin for binding to an anti-gabapentin binding partner, such as an anti-gabapentin antibody.

Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry. Certain gabapentin analogs are described in U.S. Pat. No. 4,024,175, which is incorporated herein by reference in its entirety.

In some embodiments, the gabapentin analog is selected from the group consisting of pregabalin, 3-methyl gabapentin, [(1R,5R,6S)-6-(Aminomethyl)bicyclo[−3.2.0]hept-6-yl] acetic acid, 3-(1-Aminomethyl-cyclohexylmethyl)-4H-[1,2,4]-oxadiazol-5-one, C-[1-(1H-Tetrazol-5-ylmethyl)-cycloheptyl]-methylamine, (3S,4S)-(1-Aminomethyl-3,4-dimethyl-cyclopentyl)-acetic acid, (1α,3α,5α)(3-aminomethyl-bicyclo[3.2.0]hept-3-yl)-acetic acid, (3S,5R)-3-Aminomethyl-5-methyl-octanoic acid, (3S,5R)-3-amino-5-methyl-heptanoic acid, (3S,5R)-3-amino-5-methyl-nonanoic acid and (3S,5R)-3-Amino-5-methyl-octanoic acid, (1-aminomethyl-3-methylcyclohexyl)acetic acid, (1-aminomethyl-3-methylcyclopentyl)acetic acid, (S)-3-(aminomethyl)-5-methylhexanoic acid, 3-aminomethyl-5-methyl-hexanoic acid, and (1-aminomethyl-3,4-dimethylcyclopentyl)acetic acid. In some embodiments, the second active agent may be a compound that binds with high affinity to the alpha-2-delta (α2δ) subunit of voltage-activated calcium channels.

Treatment Regimens

The treatment regimen of administering an effective amount of the cannabinoid and an effective amount of the second active agent is not necessarily limiting.

The effective amount of the cannabinoid can be administered in one or more compositions and the effective amount of the second active agent can also be administered in one or more compositions. The cannabinoid and second active agent can also be formulated together in a single composition or dosage form.

The route of administration of the cannabinoid and second active agent can be the same or different. In some embodiments, the cannabinoid or second active agent can be administered via multiple routes.

In some embodiments, the cannabinoid is administered orally, intranasally, intrapulmonarily, intravenously, topically, subcutaneously, intradermally, and/or intramuscularly.

In some embodiments, the second active agent is administered orally, intranasally, intrapulmonarily, intravenously, topically, subcutaneously, intradermally, and/or intramuscularly.

In some embodiments, the cannabinoid and second active agent can be administered together in the same composition or in separate compositions. In some embodiments, the cannabinoid and second active agent are administered in separate compositions.

The formulations for administration are not limiting and can include, e.g., immediate release, extended release, controlled release, and burst release formulations. In some embodiments, the amount of gabapentin administered to the subjects can be determined according to the subject's body weight. For example, in some embodiments, the dosage can be between about 0.1 and 500 mg/kg body weight of the subject to be treated. In some embodiments, the effective dosage is between about 0.5-250, 1-100 or 5-40 mg/kg body weight. In some embodiments, the effective amount of second active agent is in the range of about 50 mg to about 10,000 mg per day. For example, some methods entail administration to a subject in need of treatment with a second active agent in a dosage of about 100 mg, 200 mg, 250 mg, 300 mg, 500 mg, 600 mg, 750 mg, 900 mg, 1000 mg, 1200 mg, 1250 mg, 1500 mg, 1750 mg, 2000 mg, 2500 mg, 3000 mg, or 5000 mg per day. In some embodiments, subjects are administered with a dosage of between about 900 mg to about 1800 mg per day. In some embodiments, subjects are administered with a daily dosage of about 1200 to about 1800 mg gabapentin or gabapentin analog. In some embodiments, the gabapentin or gabapentin analog dosage administered is about 1800 mg day.

In some embodiments, subjects can begin the administration of the second active agent with a gradually increasing daily dosage (titrating dose) during a first stage (e.g., at the beginning) of the treatment period. In some embodiments, the first stage of treatment is about 14 days, about 13 days, about 12 days, about 11 days, about 10 days, about 9 days, about 8 days, about 7 days, about 6 days, about 5 days, about 4 days, about 3 days, or about 2 days. In some embodiments, following this first stage, the subject is administered a daily dosage of gabapentin or gabapentin analog that is relatively constant and maintained during a second stage. In some embodiments, the second stage of treatment is about 1 week, about 2 weeks, about 3 weeks, or about 4 weeks or longer. In some embodiments, following the second stage, the subject discontinues the administration of gabapentin or gabapentin analog or is administered a dosage of gabapentin or gabapentin analog that is tapered during a third stage. In some embodiments, the dosage is tapered over a period of 2 days, 3 days, 4 days, 5 days 6 days, 7 days or longer. In some embodiments, following the tapering stage, the gabapentin or gabapentin analog administration is discontinued in the subject. In some embodiments, it is maintained at a lower, maintenance dose following the third stage.

In some embodiments, the effective daily dosing of gabapentin will be initiated at about 200 to 300 to about 900 mg/day (e.g., at night) and may be increased to about 900-1800 mg starting between days 4 and 10. In some embodiments, this dosage will be maintained until 1 week prior to planned discontinuation. In some embodiments, the dosage will then be decreased to 600 mg for 1 week. In some embodiments, the dose pack may be utilized for 30 days, 60 or 90 days based on the subject's response to treatment.

The dosage of the cannabinoid administered is not necessarily limiting. In some embodiments, the dosage will be calculated to be approximately half the dose of the subjects' current cannabinoid (e.g., THC) use.

In some embodiments, the cannabinoid is administered at a daily dose of from about 0.1 mg to about 100 milligrams (mg), from about 0.5 mg to about 75 mg, from about 0.5 mg to about 50 mg, from about 0.5 mg to about 30 mg, from about 0.5 mg to about 15 mg, from about 0.5 mg to about 10 mg, from about 0.5 mg to about 10 mg, from about 0.5 mg to about 5 mg, or about 0.1 mg., 0.5 mg, 1 mg, 2 mg, 3 mg, 4 mg, 5 mg, 6 mg, 8 mg, 10 mg, 12 mg, 14 mg, 16 mg, 18 mg, 20 mg, 25 mg, 30 mg, 40 mg, 50 mg, 60 mg, 80 mg or more per daily dose.

In some embodiments, the subject is administered a dosage of the cannabinoid that is tapered over a period of time until the cannabinoid is no longer administered. In some embodiments, the dosage is tapered over a period of approximately 10-90 days. In some embodiments, the dosage is tapered over a period of 20-90 days. In some embodiments, the dosage is tapered over a period of 30-90 days until the cannabinoid is discontinued. In some embodiments, the dosage is tapered over a period of 30-60 days. For example, in some embodiments, the subject is administered a first dose of cannabinoid for a period of about 1-25 days. Following the first dosing period, in some embodiments, the subject is administered a second dose of cannabinoid that ranges from about 25%-80% of the first dose for a period of about 1-25 days. Following the second dosing period, in some embodiments, the subject is administered a third dose of cannabinoid that ranges from about 25%-80% of the second dose for a period of about 1-25 days. Following the third dosing period, in some embodiments, the subject is administered a fourth dose of cannabinoid that ranges from about 25%-80% of the third dose for a period of about 1-25 days.

For example, in some embodiments, the subject is administered a first dose of cannabinoid for a period of about 1-7 days. In some embodiments, this first dose will be equivalent to approximately 75% of the patient's usual self-dosing of *cannabis*. Following the first dosing period, in some embodiments, the subject is administered a second dose of cannabinoid that ranges from about 25%-80% of the first dose for a period of about 1-14 days. Following the second dosing period, in some embodiments, the subject is administered a third dose of cannabinoid that ranges from about 25%-80% of the second dose for a period of about 1-25 days. Following the third dosing period, in some embodiments, the subject is administered a fourth dose of cannabinoid that ranges from about 25%-80% of the third dose for a period of about 1-25 days.

In some embodiments, the subject to be treated in accordance with the methods has ceased or substantially reduced the unwanted cannabinoid/*cannabis* use for at least about 1-5 days, e.g., at least 1 day, at least 2 days, at least 3 days, at least 4 days or at least 5 days prior to the start of the discloses methods. In some embodiments, the subject has ceased or substantially reduced the unwanted cannabinoid/ *cannabis* use for a period that is at least 7 days, 8 days, 9 days 10 days, 11 days, 12 days, 13 days or 14 days or longer. In some embodiments, assessment of severity of substance dependence of a subject can be performed at the beginning of the treatment period and also monitored along the process. This can be accomplished with methods or measures well known in the art. For example, subjects with *cannabis* dependence can be screened according to the respective criteria set forth in DSM-IV or DSM-IV-TR or DSM-V. The criteria set forth in DSM can be employed to identify subjects with *cannabis* dependence and severity of symptoms associated with acute or protracted *cannabis* withdrawal. Other methods that may be used to examine *cannabis* dependence include the Fagerstrom test for nicotine dependence (FIND) (Heatherton et al., *Br. J. Addict.* 86:1119-27, 1991). FIND is a 6-item rating scale of nicotine dependence and can be employed to assess *cannabis* dependence in subjects. Illicit drug use index (IDUI) (Clayton and Voss, DHHS Pub. No. (ADM) 81-1167, 1981; and NIDA Res Monogr. 39:1-187, 1981) allows assessment of the frequency and duration of illicit drug use.

Symptoms of *cannabis* withdrawal can also be monitored during treatment. For example, when the dose of cannabinoid, e.g., nabilone, and second active agent (e.g., gabapentin) is adjusted during the treatment, the symptoms of withdrawal can be monitored to ensure that the adjusted dosages maintain therapeutic effectiveness to treat the withdrawal symptoms. Symptoms of *cannabis* withdrawal can be quantified using various questionnaires and scales as described herein, including the *Cannabis* Withdrawal Scale (CWS), Withdrawal Bothersomeness Scale (WBS), 11-item *Cannabis* Withdrawal Questionnaire (CWQ), Sleep questionnaire, Patient Global Impression of Severity scale (PGI-S), and Clinician global impression scale (CGI). See FIGS. 21-26. See also Allsop et al., *PLOS one* 7(9):e44864 (2012); Allsop et al., *Drug and Alcohol Dependence* 119:123-129 (2011); Gorelick et al., *Drug Alcohol Depend* 123(1-3):141-147 (2012). Symptoms of *cannabis* withdrawal can also be assayed by reference to cortisol levels, heart rate, and weight loss, for example.

One skilled in the art can also readily determine an appropriate dosage regimen for administering the cannabinoid and second active agent or composition of the invention to a given subject. For example, the compound(s) or composition(s) can be administered 1-4 times daily to a subject for about four to about sixteen weeks. In some dosage regimens, the compound(s) or composition(s) are administered orally. Where a dosage regimen comprises multiple administrations, it is understood that the effective amount of the compound(s) or composition(s) administered to the subject can comprise the total amount of the compound(s) or composition(s) administered over the entire dosage regimen. The exact amount will depend on the purpose of the treatment, the subject to be treated, and will be ascertainable by a person skilled in the art using known methods and techniques for determining effective doses.

Methods and compositions of the invention provide for effective treatment and mitigation of *cannabis* withdrawal syndrome utilizing a combination of a cannabinoid, preferably nabilone, and a second active agent, preferably gabapentin. In a particularly preferred embodiment, about 6 mg nabilone and 300-600 mg gabapentin are administered on a daily basis for at least 3 days, providing rapid and effective treatment of *cannabis* withdrawal symptoms such as craving. Surprisingly, although nabilone and gabapentin have relatively short half-lives and are commonly administered twice or thrice daily, combination therapy of the invention may be preferably administered once daily. Also surprisingly, it is shown herein that the combination can mitigate the symptoms of *cannabis* withdrawal in as little as four hours following administration of the first dose. See, e.g., FIGS. 10-14.

In another aspect of the invention, structured dosing regimes are provided under which subjects are administered declining doses of a cannabinoid, preferably nabilone, and a second active agent, preferably gabapentin, is adjusted as needed (e.g., initially upward and then declining doses) over an about 1.5 to 8 week period to provide both effective treatment and limited exposure to high levels of both active drugs.

In one aspect of the invention, significant improvement in withdrawal symptoms is seen within about 24, 22, 20, 18, 16, 15, 14, 13, 12, 11, 10, 9, 8, 7, 6, 5, or 4 hours or less. Preferably, improvement is seen about 4-12 hours following dosing.

In some embodiments, the dose of nabilone is tapered down 1, 2, 3, 4, 5, 6, 7, 8, or 9 or more times in a treatment. In some embodiments, the dose of gabapentin can be adjusted 1, 2, 3, 4, 5, 6, 7, 8 or 9 or more times in a treatment. In some embodiments of a treatment regimen, the dose of gabapentin is first increased one or more times, followed by administering gabapentin within a certain range for a period of time, followed by a tapering down of the gabapentin dose, until it is either discontinued or maintained at a specified dose. In some embodiments, the dose of gabapentin is adjusted downward 1, 2, 3, 4, or 5 times during the tapering. In some embodiments, daily doses of the invention can be illustrated in the following titration schedules:

|      | Titration Schedule 1 | | Titration Schedule 2 | |
| --- | --- | --- | --- | --- |
| Dose | Nabilone (mg) | Gabapentin (mg) | Nabilone (mg) | Gabapentin (mg) |
| 1 | 5-7 | 50-700 | 3-5 | 50-700 |
| 2 | 4-6 | 300-1000 | 2.5-4 | 300-1000 |
| 3 | 3-5 | 300-1200 | 2-3 | 300-1200 |
| 4 | 2-4 | 300-1200 | 1.5-2 | 300-1200 |
| 5 | 1-3 | 300-1200 | 1-1.5 | 300-1200 |
| 6 | 0.5-2 | 300-1200 | 0.5-1 | 300-1200 |
| 7 | 0.25-1 | 300-1000 | 0.25-0.5 | 300-1000 |
| 8 | 0.0-0.50 | 300-1000 | 0.0-0.25 | 0-1000 |

Preferably, gabapentin daily dosing is limited to about 900 to 1000 mg or less. Daily dose combinations can be administered at separate times or preferably at the same time. Doses of the invention can be administered for 1, 2, 3, 4, 5, 6, 7 days or more before moving to the next daily dose. In one aspect of the invention, daily doses are administered for at least 3 or 4 days. It is understood that examples of dosing regimes herein utilizing 3 or 4 day durations for each dosing step may be adjusted to have step durations from 1 to 7 or more days. In a preferred embodiment, daily doses are provided for alternating 3 and 4 day periods. The preferred time for dosing is in the evening. For example, a first daily dose can be maintained for 3 days followed by a second (different) daily dose for 4 days, followed by a third (different) daily dose provided for 3 days, etc. Alternating 3 and 4 day periods facilitates presentation of full week dosing on a fixed medium such as a card or blister pack.

In some embodiments, daily doses of the invention can be illustrated in the following titration schedules:

|      | Titration Schedule 3 | | Titration Schedule 4 | |
| --- | --- | --- | --- | --- |
| Days | Nabilone (mg) | Gabapentin (mg) | Nabilone (mg) | Gabapentin (mg) |
| 1-3 | 6 | 50-1000 | 6 | 300-600 |
| 4-7 | 5 | 300-1000 | 5 | 500-700 |
| 8-10 | 4 | 600-1000 | 4 | 600-900 |
| 11-14 | 3 | 600-1000 | 3 | 600-900 |
| 15-17 | 2 | 600-1200 | 2 | 600-900 |
| 18-21 | 1 | 600-1200 | 1 | 600-1000 |
| 22-24 | 0.5 | 600-1200 | 0.5 | 600-900 |
| 25-28 | 0.25 | 600-1200 | 0.25 | 600-900 |
| 29-31 | 0 | 200-1000 | 0 | 600-900 |
| 32-38 | 0 | 200-900 | 0 | 200-900 |
| 39-41 | 0 | 200-400 | 0 | 200-300 |

|      | Titration Schedule 5 | | Titration Schedule 6 | |
| --- | --- | --- | --- | --- |
| Days | Nabilone (mg) | Gabapentin (mg) | Nabilone (mg) | Gabapentin (mg) |
| 1-3 | 3 | 50-1000 | 3 | 300-600 |
| 4-7 | 2.5 | 300-1000 | 2.5 | 500-700 |
| 8-10 | 2 | 600-1000 | 2 | 600-900 |

-continued

| | Titration Schedule 5 | | Titration Schedule 6 | |
| --- | --- | --- | --- | --- |
| Days | Nabilone (mg) | Gabapentin (mg) | Nabilone (mg) | Gabapentin (mg) |
| 11-14 | 1.5 | 600-1000 | 1.5 | 600-900 |
| 15-17 | 1 | 600-1200 | 1 | 600-900 |
| 18-21 | 0.5 | 600-1200 | 0.5 | 600-1000 |
| 22-24 | 0.25 | 600-1200 | 0.25 | 600-900 |
| 25-28 | 0.25 | 600-1200 | 0.25 | 600-900 |
| 29-31 | 0 | 200-1000 | 0 | 600-900 |

Methods of the invention include dosage regimes and schedules as set forth above, in the Examples and in FIGS. 19 and 20. In one embodiment of the invention, nabilone is administered in a first daily dose of about 6 mg for at least 3 days followed sequentially by daily doses of about 5 mg nabilone, about 4 mg nabilone, about 3 mg nabilone, about 2 mg nabilone, about 1 mg nabilone, about 0.5 mg nabilone and about 0.25 mg nabilone, each for at least 3 days and each in combination with a therapeutically effective amount of gabapentin. Alternatively, nabilone is administered in a first daily dose of about 3 mg for at least 3 days followed sequentially by daily doses of about 2.5 mg nabilone, about 2 mg nabilone, about 1.5 mg nabilone, about 1 mg nabilone, about 0.5 mg nabilone and about 0.25 mg nabilone, each for at least 3 days and each in combination with a therapeutically effective amount of gabapentin. Generally, the initial dose of gabapentin will be about 300-600 mg daily, increasing to preferably at least about 900 to 1000 mg and up to about 1200 mg daily during treatment and then declining to less than 300 mg gabapentin. Treatment may, optionally, include a period of low gabapentin treatment following the cessation of nabilone administration. Alternatively, dosing regimes of the invention, including those set forth in FIGS. 19 and 20 and Example 2, may omit the gabapentin only portion of the treatment. Alternatively, gabapentin may be omitted entirely from any of the dosing regimes described herein or limited to about 300 to about 600 or about 900 mg daily. In a preferred embodiment, treatment ends with administration of 0.25 mg nabilone in combination with about 200-700, about preferably 200-300 mg gabapentin and is completed within 2 to 6 weeks. In another embodiment of the invention, the final nabilone-gabapentin combination dose, including in all of the dosing schedules disclose herein, may be revised to be about 0.25 mg nabilone in combination about 100-200 mg gabapentin. For all of the dosing regimes of the invention, Patients may optionally be administered 300 mg gabapentin on the day preceding combination nabilone/gabapentin therapy.

In another aspect of the invention, if the subject begins to present increasing withdrawal symptoms as cannabinoid dosing (preferably nabilone dosing) is reduced, dosing may revert to a prior or earlier cannabinoid dose until withdrawal symptoms are again controlled before returning to declining titration of cannabinoid dosing. For example, if bothersome withdrawal symptoms emerge at a daily nabilone dose of 2 mg, dosing can be reverted to 3 mg nabilone/daily before attempting further downward titration. In the foregoing, gabapentin can also be adjusted if needed, e.g., as set forth above, in FIGS. 19 and 20, Example 2, or as therapeutically warranted.

In another aspect of the invention, treatment may be terminated after fewer than all of the dosing steps have been completed. For example, some embodiments of the invention include dosing regimes where only the first 2, 3, 4, 5, 6, or 7 of the dosage steps have been administered. In one aspect of the invention, long term therapy may be administered to a subject to address lingering withdrawal symptoms. In some embodiments, long term doses of the invention may comprise 0.25 mg to 1 mg nabilone, preferably 0.25 to 0.5 mg nabilone, in combination with 100-700 mg gabapentin, preferably about 100-300 mg gabapentin. In some embodiments, long term doses may be administered daily, every other day, or as the need arises.

In some embodiments, the incidence of *cannabis* withdrawal symptoms can be assessed using one or more questionnaire-based scales, including the *Cannabis* Withdrawal Scale (CWS), the *Cannabis* Withdrawal Questionnaire (CWQ), the Sleep Questionnaire, the Patient Global Impression of Severity (PGI-S), and the Clinician Global Impression (CGI) as illustrated in FIGS. 21 and 23-26. Notably, in one aspect of the invention, withdrawal is assessed in a manner that measures the actual importance or bothersomeness of a symptom to the patient, such as by utilizing the Withdrawal Bothersomeness Scale (WBS) as illustrated in FIG. 22. Subscales or individual metrics from any the foregoing may also be utilized to assess withdrawal, including the subscales described Example 1. For example, Question 1 from the CWS or WBS scales can be utilized to assess craving severity or bothersomeness. Alternatively, the CWS 6 question and/or Craving subscales, as described in Example 1 may be used. The CWS 6 question subscale includes: 1) The only thing I could think about was smoking *cannabis;* 2) I had no appetite; 3) I had been imagining being stoned; 4) I felt restless; 5) I woke up early; and 6) I had trouble getting to sleep at night. In an alternative embodiment, a 5 question CWS subscale may be used that includes: 1) The only thing I could think about was smoking *cannabis;* 2) I had been imagining being stoned; 3) I felt restless; 4) I woke up early; and 5) I had trouble getting to sleep at night. The Craving subscale includes: 1) The only thing I could think about was smoking *cannabis*; and 2) I had been imagining being stoned.

In one embodiment of the invention, a patient is administered about 3 mg or about 6 mg of nabilone in combination with about 300-600 mg of gabapentin for at least 3 days thereby reducing or preventing *cannabis* withdrawal symptoms as measured by one or more of the assessment tools, including subscales or individual metrics, described herein. In some embodiments, nabilone can then be down titrated and gabapentin increased and then down titrated at rates that maintain significant reduction in or prevention of *cannabis* withdrawal symptoms. In one embodiment, dosing is adjusted in a manner that limits any increase in withdrawal symptoms to no more than about 150%, 140%, 130%, 120%, 115%, 110%, 105% or less of the withdrawal symptom level(s) that is achieved about 12, 18 or 24 hrs after the first dose of nabilone and gabapentin is administered as measured by one or more of the assessment tools, including subscales or individual metrics, described herein.

In a preferred embodiment of the invention, initial treatment significantly reduces *cannabis* craving levels and craving levels during the titration process are controlled, rising to no more than 110% or 105% of the initial level of craving reduction that is achieved about 12, 18 or 24 hrs after the first dose of nabilone and gabapentin is administered. Most preferably, titration is achieved with none to minimal increase in withdrawal symptoms.

Initial levels of withdrawal symptoms can be measured over the duration of initial treatment or at set time points (e.g., at the 12 hr, 18 hr or 24 hr post dosing time points) during the initial treatment and averaged to determine the reduction level.

In another aspect of the invention, treatment reduces withdrawal symptoms to a score of 40, 39, 38, 37, 36, 35, 34, 33, 32, 31 or preferably 30 or less as measured by the CWS, or to a score of 25, 24, 23, 22, 21, 20, 15 or preferably 10 or less on the CWS 6 question subscale described herein, or 21, 20, 19, 18, 15, 10 or preferably 9 or less on the CWS 5 question subscale described herein. In another embodiment, treatment reduces withdrawal symptoms to a score of 20, 19, 18, 17, 16, or preferably 15, or most preferably 10, or less as measured by the WBS or to a score of 4 or less on the WBS 6 question subscale. In another embodiment, treatment reduces withdrawal symptoms to a score of 18, 15, 10 or preferably 9 or less on the five question WBS scale derived by omitting "I had no appetite" from the WBS 6 question scale.

In another embodiment, treatment reduces withdrawal symptoms to a score of 1.5, preferably 1.25 or less on the PGI severity scale; or 1.2, or preferably 1.0, or less on the PGI bothersome scale (as exemplified in Example 1. In another embodiment, treatment reduces withdrawal symptoms to a score of 1.25 or preferably 1.0 or less on the CGI scale.

In another aspect of the invention, nabilone and gabapentin can be administered, and then nabilone can then be down titrated and gabapentin increased and then down titrated at levels and rates that maintain withdrawal symptoms to within 150%, 140%, 130%, 120%, 115%, 110%, 105% or less of the withdrawal symptom level(s), as measured by any of the assessment tools discussed above, associated with ongoing *cannabis* use prior to attempts to cease or limit *cannabis* use (i.e., using the non-withdrawing state as a baseline). Preferably, the non-withdrawing state is measures within about 7 days and preferably 1-3 days of treatment.

In another aspect of the invention, withdrawal symptoms are monitored and assessed using biometric means including evening cortisol levels, heart rate and weight loss. In one aspect of the invention, it has been discovered that subjects experiencing *cannabis* withdrawal also have increased evening cortisol levels, indicating significant stress. In some embodiments, subjects taking placebo therapy experience 36-60% increased evening cortisol from baseline, an increase of at least 20% more than subjects taking combination nabilone plus gabapentin therapy. In one embodiment, dosing is adjusted at a rate that limits any increase in evening cortisol corresponding to withdrawal symptoms to no more than 120%, 115%, 110%, preferably 105% or less of the evening cortisol levels associated with the initial combination therapy, e.g., that which is achieved about 24 hrs after the first dose of nabilone and gabapentin is administered. Cortisol levels may be measured by serum as conducted herein or by salivary methods known in the art. Inder et al., *Clin. Endocrinol.*, 77:645-51 (2012); Restituto et al., *Clin. Biochem.*, 41(9):688-692 (2008).

In some embodiments, the evening cortisol levels in the patient are determined at a time point from about 5 pm to about midnight, about 6 pm to about midnight, about 7 pm to about midnight, about 8 pm to about midnight, or about 9 pm to about midnight.

In another aspect of the invention, it has been discovered that subjects experiencing *cannabis* withdrawal also have increased standing heart rate, indicating physiologic changes associated with withdrawal. Subjects taking placebo therapy experience a significantly higher mean heart rate compared to subjects taking combination nabilone plus gabapentin therapy. In one embodiment, dosing is adjusted at a rate that limits any increase in standing heart rate to an increase of no more than 5% or less of the standing heart rate associated with the initial combination therapy, e.g., that which is achieved about 12 to 24 hrs after the first dose of nabilone and gabapentin is administered or within about 7 days, preferably 1 to 3 days, before the beginning of treatment.

In another aspect of the invention, it has been discovered that subjects experiencing *cannabis* withdrawal also experience loss of appetite and weight loss. In one embodiment, dosing is adjusted at a rate that limits any weight loss to no more than 1 kg (2.2 lbs) or less of the subject's weight during initial combination therapy, e.g., that is achieved about 12 to 24 hrs after the first dose of nabilone and gabapentin is administered or within about 7 days, preferably 1 to 3 days, before the beginning of treatment.

In another aspect of the invention, subjects receiving combination therapy experience improved sleep quality compared to subjects experiencing *cannabis* withdrawal. In one embodiment of the invention, dosing is adjusted at a rate that maintains improvement in sleep quality. Preferably, the treated subjects experience about 0.5, 0.75, 1.0, 1.25 or most preferably, about 1.5 hrs or more of additional sleep.

In another aspect of the invention, subjects receiving the combination therapy may experience reduction, mitigation or elimination of other symptoms associated with *cannabis* withdrawal and/or *cannabis* use disorder. Such symptoms may include hyperemesis and/or presyncope.

In particular, in a preferred embodiment of the invention, nabilone and gabapentin are administered in amounts sufficient so as to achieve an initial mean $AUC_{0-24}$ levels of about 33,000-35000 pg-hr/mL and 25,000-72,500 pg-hr/mL respectively for initial daily dosing. In some embodiments, daily dosing continues for at least 3 days. Following the initial dosing period, nabilone and gabapentin may be titrated utilizing the assessment and biometric tools discussed herein. Alternatively, nabilone and gabapentin may be titrated according to the following table and gabapentin adjusted accordingly:

| Dose | Nabilone mean $AUC_{0-24}$ Range (pg-hr/mL) | | Gabapentin mean $AUC_{0-24}$ Range (pg-hr/mL) | |
|---|---|---|---|---|
| 1 | 33000 | 35000 | 25000 | 72500 |
| 2 | 27500 | 29167 | 50000 | 72500 |
| 3 | 22000 | 23333 | 75000 | 110000 |
| 4 | 16500 | 17500 | 75000 | 110000 |
| 5 | 11000 | 11667 | 75000 | 110000 |
| 6 | 5500 | 5833 | 75000 | 150000 |
| 7 | 2750 | 2917 | 75000 | 150000 |
| 8 | 1375 | 1458 | 75000 | 110000 |
| 9 | 0 | 0 | 50000 | 110000 |
| 10 | 0 | 0 | 25000 | 110000 |
| 11 | 0 | 0 | 25000 | 110000 |
| 12 | 0 | 0 | 10000 | 35000 |

In some embodiments, subjects are administered a cannabinoid, preferably nabilone, and a second active agent, preferably gabapentin at dose levels to achieve specified pharmacokinetic (PK) levels. In some embodiments, the invention provides a method of treating *cannabis* withdrawal syndrome comprising administering a first dose on a daily basis to a patient in need thereof nabilone in an amount sufficient to achieve a mean $AUC_{0-24}$ range of 23100-47250 pg-hr/mL and gabapentin in an amount sufficient to achieve a mean $AUC_{0-24}$ range of 17500-97875 pg-hr/mL. In some embodiments, the nabilone and gabapentin may be titrated according to the following table and gabapentin adjusted accordingly:

| Dose | Nabilone mean $AUC_{0-24}$ Range (pg-hr/mL) | | Gabapentin mean $AUC_{0-24}$ Range (pg-hr/mL) | |
|---|---|---|---|---|
| 1 | 23100 | 47250 | 17500 | 97875 |
| 2 | 19250 | 37917 | 35000 | 97875 |
| 3 | 15400 | 30333 | 75000 | 143000 |
| 4 | 11500 | 22750 | 52500 | 143000 |
| 5 | 7700 | 15167 | 52500 | 143000 |
| 6 | 3850 | 7582 | 52500 | 195000 |
| 7 | 1925 | 3792 | 52500 | 195000 |
| 8 | 962.5 | 1895 | 52500 | 143000 |
| 9 | 0 | 0 | 35000 | 143000 |
| 10 | 0 | 0 | 17500 | 143000 |
| 11 | 0 | 0 | 17500 | 143000 |
| 12 | 0 | 0 | 10000 | 35000 |

In some embodiments, a first dose of nabilone is administered in an amount sufficient on a daily basis to achieve a mean $AUC_{0-24}$ range of 26400-43750 pg-hr/mL and gabapentin is administered in an amount sufficient on a daily basis to achieve a mean $AUC_{0-24}$ range of 20000-90625 pg-hr/mL. In some embodiments, the nabilone and gabapentin may be titrated according to the following table and gabapentin adjusted accordingly:

| Dose | Nabilone mean $AUC_{0-24}$ Range (pg-hr/mL) | | Gabapentin mean $AUC_{0-24}$ Range (pg-hr/mL) | |
|---|---|---|---|---|
| 1 | 26400 | 43750 | 20000 | 90625 |
| 2 | 22000 | 36459 | 40000 | 90625 |
| 3 | 17600 | 29166 | 60000 | 137500 |
| 4 | 13200 | 21875 | 60000 | 137500 |
| 5 | 8800 | 14584 | 60000 | 137500 |
| 6 | 4400 | 7291 | 60000 | 187500 |
| 7 | 2200 | 3646 | 60000 | 187500 |
| 8 | 100 | 1822 | 60000 | 137500 |
| 9 | 0 | 0 | 40000 | 137500 |
| 10 | 0 | 0 | 20000 | 137500 |
| 11 | 0 | 0 | 20000 | 137500 |
| 12 | 0 | 0 | 8000 | 43750 |

PK-based dosing regimes of the invention include those set forth above and those that extend the ranges above by up to 10, 15, 20% or 25% in both directions. Daily dosing may be administered for 1, 2, 3, 4, 5, 6, 7 days or more before moving to the next daily dose in the schedule. In one aspect of the invention, daily doses are administered for at least 3 or 4 days. In a preferred embodiment, daily doses are provided for alternating 3 and 4 day periods. Fewer than all of the dosing steps may be utilized, such that treatment is terminated after treatment with daily Dose 4, 5, 6, 7, or 8 is completed. In one embodiment of the invention, Dose 6, 7 or 8 may be extended to provide long term therapy. In some embodiments, one or more of the doses can be eliminated or omitted. For example, in some embodiments, any one or a combination of Dose 2, 3, 4, 5, 6, 7, 8, 9 10, 11 or 12 is omitted. For example, in some embodiments, Dose 4 is eliminated, and the patient can proceed from Dose 3 directly to Dose 5. $AUC_{0-infinity}$ may be used by increasing the above ranges by about 8-10%.

Compositions

The cannabinoid and second active agent of the present invention can be administered alone or in combination with one or more active pharmaceutical agents.

Solid dosage forms for oral administration may include capsules, tablets, pills, powders, gel caps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

In some embodiments, the second active agent and/or the cannabinoid is administered by an intravaginal ring. In some embodiments, the intravaginal ring is formulated for extended release or immediate release. In some embodiments, therapeutic levels of the second active agent and/or the cannabinoid are released over a period of days by a single ring, e.g., 5 days, 6 days, 7 days, 10 days, 2 weeks, or longer. In some embodiments, the treatment regimen incorporates a series of rings wherein a first ring is administered that supplies a first dose of second active agent and/or cannabinoid followed by the administration of one or more additional intravaginal rings in sequence that provide, e.g., a second dose, third dose, etc. of the second active agent and/or cannabinoid.

Dosage forms for topical or transdermal administration of a compound can further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

In one embodiment, the second active agent and/or cannabinoid is delivered transdermally. The term "transdermal delivery" as used herein means administration of the pharmaceutical composition topically to the skin wherein the active ingredient or its pharmaceutically acceptable salts, will be percutaneously delivered in a therapeutically effective amount.

In some embodiments, the composition to be applied transdermally further comprises an absorption enhancer. The term "absorption enhancer" as used herein means a compound which enhance the percutaneous absorption of drugs. These substances are sometimes also referred to as skin-penetration enhancers, accelerants, adjuvants and sorption promoters. Various absorption enhancers are known to be useful in transdermal drug delivery. U.S. Pat. Nos. 5,230,897, 4,863,970, 4,722,941, and 4,931,283 disclose some representative absorption enhancers used in transdermal compositions and for topical administration. In some embodiments, the absorption enhancer is N-lauroyl sarcosine, sodium octyl sulfate, methyl laurate, isopropyl myristate, oleic acid, glyceryl oleate or sodium lauryl sulfoacetate, or a combination thereof. In some embodiments, the composition contains on a weight/volume (w/v) basis the absorption enhancer in an amount of about 1-20%, 1-15%, 1-10% or 1-5%. In some embodiments, to enhance further the ability of the therapeutic agent(s) to penetrate the skin or mucosa, the composition can also contain a surfactant, an azone-like compound, an alcohol, a fatty acid or ester, or an aliphatic thiol.

In some embodiments, the transdermal composition can further comprise one or more additional excipients. Suitable excipients include without limitation solubilizers (e.g., C2-C8 alcohols), moisturizers or humectants (e.g., glycerol [glycerin], propylene glycol, amino acids and derivatives thereof, polyamino acids and derivatives thereof, and pyrrolidone carboxylic acids and salts and derivatives thereof), surfactants (e.g., sodium laureth sulfate and sorbitan monolaurate), emulsifiers (e.g., cetyl alcohol and stearyl alcohol), thickeners (e.g., methyl cellulose, ethyl cellulose, hydroxymethyl cellulose, hydroxypropyl cellulose, polyvinylpyrrolidone, polyvinyl alcohol and acrylic polymers), and formulation bases or carriers (e.g., polyethylene glycol as an ointment base). As a non-limiting example, the base or carrier of the composition can contain ethanol, propylene glycol and polyethylene glycol (e.g., PEG 300), and optionally an aqueous liquid (e.g., isotonic phosphate-buffered saline).

Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition calculated to produce the desired responses in association with its administration, e.g., the appropriate route and treatment regimen. Also of importance is the subject to be treated, in particular, the state of the subject and the protection desired.

In some embodiments, pharmaceutical compositions of the present invention comprise an effective amount of a second active agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one cannabinoid and/or second active agent will be known to those of skill in the art in light of the present disclosure, as exemplified by *Remington's Pharmaceutical Sciences*, 18th Ed. Mack Printing Company, 1990, incorporated herein by reference. Moreover, for animal (e.g., human) administration, it will be understood that preparations should meet sterility, pyrogenicity, general safety and purity standards as required by the FDA.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences,* 18th Ed. Mack Printing Company, 1990, pp. 1289-1329, incorporated herein by reference). Except insofar as any conventional carrier is incompatible with the active ingredient, its use in the pharmaceutical compositions is contemplated.

The cannabinoid and/or second active agent may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, *Remington's Pharmaceutical Sciences,* 18th Ed. Mack Printing Company, 1990, incorporated herein by reference).

The cannabinoid and/or second active agent may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include cannabinoid and/or second active agent one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the cannabinoid and/or second active agent may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments of the present invention, the cannabinoid and/or second active agent, are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier or they may be enclosed in hard- or soft-shell gelatin capsule, or they may be compressed into tablets, or they may be incorporated directly with the food of the diet.

In some embodiments, the second active agent and/or cannabinoid are formulated to be contained in a food product, and the drugs are delivered by consuming the food product. In some embodiments, the food product comprises gummy candy products. In some embodiments, the food products are cookies. The food product that can be used is not limiting.

In certain embodiments, the active compounds may be incorporated with excipients and used in the form of ingestible tablets, buccal tables, troches, capsules, elixirs, suspensions, syrups, wafers, and the like U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001, which is incorporated herein by reference in its entirety. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the cannabinoid and/or second active agent may be administered via a parenteral route. As used herein, the term "parenteral" includes routes that bypass the alimentary tract. Specifically, the pharmaceutical compositions disclosed herein may be administered for example, but not limited to intravenously, intradermally, transdermally, intramuscularly, intraarterially, intraventricularly, intrathecally, subcutaneous, or intraperitoneally U.S. Pat. Nos. 6,7537,514; 6,613,308; 5,466,468; 5,543,158; 5,641,515; and 5,399,363 (each specifically incorporated herein by reference in its entirety).

Kits

The invention also provides kits comprising the cannabinoid and second active agent. In some embodiments, the kit comprises a plurality of daily doses of nabilone; a plurality of daily doses of gabapentin; and optionally a dosing schedule for administering the nabilone and gabapentin to a patient. In some embodiments, the kit can also comprise one or more questionnaires or scales for the patient or health care provider to assess withdrawal symptoms, for example, as described herein. One or more reagents for detection of cortisol in serum or saliva can also be provided.

In some embodiments, kits present dosing for 1 week, 2 weeks, 3 weeks, 4 weeks, 1 month or the complete dosing schedule or regimen on a physical substrate such as a card or blister pack.

In some embodiments, the kit comprises daily doses of nabilone. In some embodiments, the daily dose of nabilone is about 6 mg. In some embodiments, the plurality of daily doses of nabilone comprise doses selected from 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg and combinations thereof. In some embodiments, the unit dose of nabilone ranges from about 0.25 to about 6 mg. In some embodiments, the unit dose of nabilone is selected from 0.25 mg, 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg and combinations thereof.

In some embodiments, the kit comprises daily doses of gabapentin. In some embodiments, the daily doses of gabapentin comprise 300-600 mg. In some embodiments, the plurality of daily doses of gabapentin comprise doses selected from 200 mg, 300 mg, 400 mg, 500 mg, 600 mg, 700 mg, 800 mg, 900 mg 1000 mg, 1100 mg, 1200 mg, 1300 mg, 1400 mg, 1500 mg and combinations thereof. In some embodiments, the unit dose of gabapentin ranges from about 100 to about 500 mg. In some embodiments, the unit dose of gabapentin is selected from 100 mg, 150 mg, 200 mg, 250 mg, 300 mg, 350 mg, 400 mg, 450 mg, 500 mg and combinations thereof.

In some embodiments, the daily doses of gabapentin and nabilone are formulated as separate dosage forms. In some embodiments, the daily doses of gabapentin and nabilone are formulated into a single dosage form. In some embodiments, the daily doses for one week are presented on a solid substrate. In some embodiments, the solid substrate is a blister pack.

In some embodiments, the cannabinoid (e.g., nabilone) and/or second active agent (e.g., gabapentin) can be provided in a one a day dispensing unit such as a blister pack or dial pack type dispenser, preferably with days of the week or day of the month (e.g., 1, 2, 3, 4, etc.) printed on the dispenser. If the cannabinoid and/or second active agent are to be administered every day or twice (or more) a day, the dispensing unit can be modified accordingly.

In addition to the above embodiments, behavioral modification and interaction with patients may also occur with internet and Apps to assist in titrating and tapering of dosing.

Sample Embodiments

This section describes exemplary compositions and methods of the invention, presented without limitation, as a series of paragraphs, some or all of which may be alphanumerically designated for clarity and efficiency. Each of these paragraphs can be combined with one or more other paragraphs, and/or with disclosure from elsewhere in this application, including the materials incorporated by reference, in any suitable manner. Some of the paragraphs below expressly refer to and further limit other paragraphs, providing without limitation examples of some of the suitable combinations.

1. A method of treating *cannabis* use disorder or *cannabis* withdrawal syndrome in a subject, comprising administering to the subject in need thereof:
   i) an effective amount of a cannabinoid; and
   ii) an effective amount of a second active agent.
2. A method of mitigating one or more symptoms of cannabinoid withdrawal in a subject, comprising administering to the subject in need thereof:
   i) an effective amount of a cannabinoid; and
   ii) an effective amount of a second active agent.
3. The method of any of paragraphs 1 or 2, wherein the cannabinoid comprises cannabidiol, nabilone, or a combination of cannabidiol and nabilone.
4. The method of any of paragraphs 1-3, wherein the second active agent comprises pregabalin, gabapentin or a combination thereof.
5. The method of any of paragraphs 1-4, wherein the cannabinoid and/or second active agent is administered in the form of a pharmaceutically acceptable salt.
6. The method of any of paragraphs 1-5, wherein the subject is administered a composition comprising the cannabinoid and second active agent.
7. The method of any of paragraphs 1-6, wherein the composition is administered orally, intranasally, intrapulmonarily, intravenously, topically, subcutaneously, intradermally, or intramuscularly.
8. The method of any of paragraphs 1-5, wherein the cannabinoid and second active agent are administered in separate compositions.
9. The method of paragraph 8, wherein the composition comprising second active agent is administered orally, intranasally, intrapulmonarily, intravenously, topically, subcutaneously, intradermally, or intramuscularly.
10. The method of paragraph 8, wherein the composition comprising the cannabinoid is administered orally, intranasally, intrapulmonarily, intravenously, topically, subcutaneously, intradermally, or intramuscularly.
11. The method of any of paragraphs 1-10, wherein the cannabinoid comprises a member selected from the group consisting of Δ9-tetrahydrocannabinol (THC), Δ8-tetrahydrocannabinol, 11-OH-delta-9-THC, (+)-1,1-dimethylheptyl analog of 7-hydroxy-delta-6-tetrahydrocannabinol, dodeca-2E,4E,8Z,10E/Z-tetraenoic-acid-isobutylamides, cannabinol (CBN), tocannabicyclol (CBL), cannabidivarin (CBDV), cannabidiolic acid (CBDA), cannabichromevarin (CBCV), cannabigerovarin (CBGV), cannabidiol (CBD), cannabichromene (CBC), tetrahydrocannabivarin (THCV), cannabigerol (CBG), cannabigerol monomethyl ether (CBGM), 3-(5'-cyano-1',1'-dimethylpentyl)-1-(4-N-morpholinobutyryloxy) Δ8-tetrahydrocannabinol hydrochloride], dexanabinol, nabilone (6aR, 10aR)-1-hydroxy-6,6-dimethyl-3-(2-methyloctan-2-yl)-7,8,10,10a-tetrahydro-6aH-benzo[c]chromen-9-one), levonantradol, or N-(2-hydroxyethyl) hexadecanoamide, and salts thereof, and combinations thereof.

12. The method of any of paragraphs 1-11, wherein the second active agent is selected from the group consisting of gabapentin, pregabalin, 3-methyl gabapentin, [(1R,5R,6S)-6-(Aminomethyl)bicyclo[−3.2.0]hept-6-yl]acetic acid, 3-(1-Aminomethyl-cyclohexylmethyl)-4H-[1,2,4]-oxadiazol-5-one, C-[1-(1H-Tetrazol-5-ylmethyl)-cycloheptyl]-methylamine, (3S,4S)-(1-Aminomethyl-3,4-dimethyl-cyclopentyl)-acetic acid, (1α,3α,5α)(3-amino-methyl-bicyclo[3.2.0]hept-3-yl)-acetic acid, (3S,5R)-3-Aminomethyl-5-methyl-octanoic acid, (3S,5R)-3-amino-5-methyl-heptanoic acid, (3S,5R)-3-amino-5-methyl-nonanoic acid and (3S,5R)-3-Amino-5-methyl-octanoic acid, (1-aminomethyl-3-methylcyclohexyl)acetic acid, (1-aminomethyl-3-methylcyclopentyl)acetic acid, (S)-3-(aminomethyl)-5-methylhexanoic acid, 3-aminomethyl-5-methyl-hexanoic acid, and (1-aminomethyl-3,4-dimethylcyclopentyl)acetic acid.
13. The method of any of paragraphs 1-12, wherein the subject is administered a dosage of the cannabinoid that is tapered over a period of time.
14. The method of any of paragraphs 1-13, wherein the subject is administered a dosage of the second active agent that is titrated with an increasing dose for a period of time.
15. The method of paragraph 14, wherein the subject is administered a dosage of the second active agent that is maintained for a period of time following the titration.
16. The method of paragraph 15, wherein the subject is administered a dosage of the second active agent that is tapered for a period of time following the administration of the dosage that is maintained for a period of time.
17. The method of any of paragraphs 1-16, wherein the administration of cannabinoid is discontinued after a period of time.
18. The method of any of paragraphs 1-17, wherein the administration of second active agent is discontinued after a period of time.
19. The method of any of paragraphs 1-18, wherein the cannabinoid is nabilone.
20. The method of paragraph 19, wherein nabilone is administered at a daily dose of about 6 mg.
21. The method of any of paragraphs 1-20, wherein the cannabinoid is administered for at least three days.
22. The method of any of paragraphs 1-21, wherein the second active agent is gabapentin.
23. The method of paragraph 22, wherein the gabapentin is administered at a daily dose of at least about 300 mg.
24. The method of paragraph 22, wherein gabapentin is administered at a daily dose of at least about 600 mg.
25. The method of any of paragraphs 1-21, wherein gabapentin is administered at a daily dose of between about 300 mg to about 600 mg.

26. The method of any of paragraphs 1-25, wherein the dose of cannabinoid is tapered over time.
27. The method of any of paragraphs 1-26, further comprising monitoring efficacy of treatment by conducting one or more assessments.
28. The method of paragraph 27, wherein the assessment is selected from the group consisting of assaying cortisol levels, assessing sleep, assessing weight loss, assessing heart rate, assessing withdrawal symptoms by administering one or more questionnaires to the subject, assessing withdrawal symptoms based on observations of a health care provider, and combinations thereof.
29. The method of any of paragraphs 27 or 28, wherein the one or more assessments is performed before and/or after the cannabinoid dose is reduced (tapered) to monitor efficacy.
30. The method of paragraph 29, wherein the one or more assessments is performed after the dose of cannabinoid is tapered.
31. The method of any of paragraphs 27-30, wherein the one or more assessments establish efficacy of treatment.
32. The method of any of paragraphs 28-31, wherein the cortisol levels are assayed by measuring serum and/or salivary levels.
33. The method of paragraph 32, wherein evening cortisol levels are not elevated beyond a specified value relative to baseline cortisol levels in the subject.
34. The method of paragraph 32, wherein evening cortisol levels are not elevated more than 50% relative to the subject's evening baseline cortisol values.
35. The method of paragraph 32, wherein the cortisol levels are not elevated more than 40% relative to the subject's baseline evening cortisol values.
36. The method of paragraph 30, wherein the evening cortisol levels are not elevated more than 35% relative to the subject's baseline evening cortisol values.
37. The method of any of paragraphs 28-36, wherein sleep is assessed by administering a questionnaire to the subject that assesses quality and/or quantity of the subject's sleep.
38. The method of any of paragraphs 28-37, wherein the one or more questionnaires is selected from the CWS (19 items, based on an 11-point severity scale), WBS (19 items, based on a 5-point bothersomeness scale), CWS (six item subscale), CWS (two item cravings subscale), and PGI-S scale.
39. The method of paragraph 38, wherein results of the one or more questionnaires yield a score establishing efficacy of the treatment.
40. The method of any of paragraph 28-39, wherein the assessment of withdrawal symptoms based on observations of a health care provider comprises a CGI assessment.
41. The method of paragraph 40, wherein the CGI assessment provides a score that establishes efficacy of the treatment.
42. The method of any of paragraphs 28-41, wherein the subject's weight does not decrease by more than about 1% that establishes efficacy of the treatment.
43. The method of any of paragraphs 28-42, wherein the subject's standing heart rate did not increase more than about 5% that establishes efficacy of the treatment.
44. The method of any of paragraphs 1-43, wherein the cannabinoid is nabilone, wherein nabilone is administered to the subject and is tapered over a period of time.
45. The method of any of paragraphs 1-44, wherein nabilone is administered to the subject and is tapered over a period of about 21-42 days until it is discontinued.
46. The method of any of paragraphs 44-45, wherein nabilone is administered at an initial daily dose of from about 3 mg to about 6 mg.
47. The method of paragraph 46, wherein the initial daily dose of nabilone is about 6 mg.
48. The method of any of paragraphs 44-47, wherein the subject is initially administered a daily dose of nabilone of from about 3-6 mg for a first period of time, followed by a sequential tapering daily dose of nabilone that reduces the dose of nabilone, wherein the tapered doses of nabilone are administered for sequential periods of time.
49. The method of paragraph 48, wherein the first period of time is at least three days.
50. The method of paragraph 48, wherein the first period of time is three or four days, wherein the sequential periods of time alternate in three and four day intervals,
whereby if the first period of time is three days, the first sequential period of time is four days, the second sequential period of time is three days, and the third sequential period of time is four days,
whereby if the first period of time is four days, the first sequential period of time is three days, the second sequential period of time is four days, and the third sequential period of time is three days.
51. The method of paragraph 48, wherein nabilone is initially administered at a daily dose of about 3 mg for a first period of time; followed by a daily dose of about 2 mg for a second period of time; followed by a daily dose of about 1 mg for a third period of time; followed by a daily dose of about 0.5 mg for a fourth period of time; and followed by a daily dose of about 0.25 mg for a fifth period of time.
52. The method of paragraph 48, wherein nabilone is initially administered at a daily dose of about 4 mg for a first period of time; followed by a daily dose of about 3 mg for a second period of time; followed by a daily dose of about 2 mg for a third period of time; followed by a daily dose of about 1 mg for a fourth period of time; followed by a daily dose of about 0.5 mg for a fifth period of time; and followed by a daily dose of about 0.25 mg for a sixth period of time.
53. The method of paragraph 48, wherein nabilone is initially administered at a daily dose of about 5 mg for a first period of time; followed by a daily dose of about 4 mg for a second period of time; followed by a daily dose of about 3 mg for a third period of time; followed by a daily dose of about 2 mg for a fourth period of time; followed by a daily dose of about 1 mg for a fifth period of time; followed by a daily dose of about 0.5 mg for a sixth period of time; and followed by a daily dose of about 0.25 mg for a seventh period of time.
54. The method of paragraph 48, wherein nabilone is initially administered at a daily dose of about 6 mg for a first period of time; followed by a daily dose of about 5 mg for a second period of time; followed by a daily dose of about 4 mg for a third period of time; followed by a daily dose of about 3 mg for a fourth period of time; followed by a daily dose of about 2 mg for a fifth period of time; followed by a daily dose of about 1 mg for a sixth period of time; followed by a daily dose of about 0.5 mg for a seventh period of time; and followed by a daily dose of about 0.25 mg for an eighth period of time.
55. The method of any of paragraphs 1-54, wherein the second active agent is administered to the subject and is titrated and tapered over time.
56. The method of any of paragraphs 1-55, wherein the second active agent is gabapentin.
57. The method of any of paragraphs 1-56, wherein the second active agent is titrated and tapered over a period of about 21-90 days until it is discontinued.
58. The method of any of paragraphs 1-57, wherein gabapentin is administered at an initial daily dose of from about 100 mg to about 800 mg.
59. The method of paragraph 58, wherein the initial daily dose of gabapentin is between about 300 to about 600 mg.
60. The method of any of paragraphs 1-59, wherein the subject is initially administered a daily dose of gabapentin of from about 300 to about 600 mg for a first period of time, followed by a sequential titrating daily dose of gabapentin that increases the dose of gabapentin, wherein the titrating daily doses of gabapentin are administered for sequential periods of time, followed by a sequential tapering of the daily dose of gabapentin that reduces the dose of gabapentin over time, wherein the tapered doses of gabapentin are administered for sequential periods of time.
61. The method of any of paragraphs 1-60, wherein gabapentin is initially administered at a daily dose of about 300 mg for a first period of time; followed by a daily dose of about 600 mg for a second period of time; followed by a daily dose of about 900 mg for a third period of time; followed by a daily dose of about 1200 mg for a fourth period of time; followed by a daily dose of about 900 mg for a fifth period of time; followed by a daily dose of about 600 mg for a sixth period of time; and followed by a daily dose of about 300 mg for a seventh period of time.
62. The method of any of paragraphs 1-60, wherein gabapentin is initially administered at a daily dose of about 300 mg and nabilone is initially administered at a daily dose of about 6 mg for a first period of time; followed by a daily dose of about 600 mg gabapentin and a daily dose of about 5 mg nabilone for a second period of time; followed by a daily dose of about 900 mg gabapentin and a daily dose of about 4 mg nabilone for a third period of time; followed by a daily dose of about 900 mg gabapentin and a daily dose of about 3 mg nabilone for a fourth period of time; followed by a daily dose of about 900 mg gabapentin and a daily dose of about 2 mg nabilone for a fifth period of time; followed by a daily dose of about 900 mg gabapentin and a daily dose of about 1 mg nabilone for a sixth period of time; followed by a daily dose of about 1200 mg gabapentin and a daily dose of about 0.5 mg nabilone for a seventh period of time; followed by a daily dose of about 1200 mg gabapentin and a daily dose of about 0.25 mg nabilone for an eighth period of time; followed by a daily dose of about 900 mg gabapentin for a ninth period of time; followed by a daily dose of about 600 mg or about 900 mg gabapentin for a tenth period of time; and followed by a daily dose of about 300 mg gabapentin for an eleventh period of time.
63. The method of paragraph 61, wherein the first period of time is about 1-3 days; wherein the second period of time is about 4-7 days; wherein the third period of time is about 8-10 days; wherein the fourth period of time is about 11-14 days; wherein the fifth period of time is about 15-17 days; wherein the sixth period of time is about 18-21 days; wherein the seventh period of time is about 22-24 days; wherein the eighth period of time is about 25-28 days; wherein the ninth period of time is about 29-31 days; wherein the tenth period of time is about 32-35 days; and wherein the eleventh period of time is about 36-38 days.
64. The method of any of paragraphs 1-60, wherein gabapentin is initially administered at a daily dose of about 300 mg and nabilone is initially administered at a daily dose of about 6 mg for a first period of time; followed by a daily dose of about 600 mg gabapentin and a daily dose of about 5 mg nabilone for a second period of time; followed by a daily dose of about 900 mg gabapentin and a daily dose of about 4 mg nabilone for a third period of time; followed by a daily dose of about 900 mg gabapentin and a daily dose of about 3 mg nabilone for a fourth period of time; followed by a daily dose of about 900 mg gabapentin and a daily dose of about 2 mg nabilone for a fifth period of time; followed by a daily dose of about 900 mg gabapentin and a daily dose of about 1 mg nabilone for a sixth period of time; followed by a daily dose of about 1200 mg gabapentin and a daily dose of about 0.5 mg nabilone for a seventh period of time; followed by a daily dose of about 900 mg gabapentin and a daily dose of about 0.25 mg nabilone for an eighth period of time; followed by a daily dose of about 900 mg gabapentin for a ninth period of time; followed by a daily dose of about 600 mg or about 900 mg gabapentin for a tenth period of time; and followed by a daily dose of about 300 mg gabapentin for an eleventh period of time.
65. The method of paragraph 64, wherein the first period of time is about 1-3 days; wherein the second period of time is about 4-7 days; wherein the third period of time is about 8-10 days; wherein the fourth period of time is about 11-14 days; wherein the fifth period of time is about 15-17 days; wherein the sixth period of time is about 18-21 days; wherein the seventh period of time is about 22-24 days; wherein the eighth period of time is about 25-28 days; wherein the ninth period of time is about 29-31 days; wherein the tenth period of time is about 32-38 days; and wherein the eleventh period of time is about 39-41 days.
66. The method of any of paragraphs 1-65, wherein efficacy for treating *cannabis* use disorder is achieved by administering a daily dose of about 6 mg of nabilone within a time period following initial administration selected from about 4 hrs, about 5 hrs, about 10 hrs, about 24 hrs, about 36 hrs, and about 48 hrs.
67. The method of any of paragraphs 1-66, wherein the subject has moderate to severe *cannabis* use disorder.
68. The method of paragraph 67, wherein the subject has moderate to severe *cannabis* use disorder according to Diagnostic and Statistical Manual of Mental Disorders (DSM-5).
69. A pharmaceutical composition comprising an effective amount of a cannabinoid and an effective amount of a second active agent for use in treating *cannabis* use disorder or for mitigating one or more symptoms of cannabinoid withdrawal.
70. The composition of paragraph 69, wherein the cannabinoid is selected from nabilone and the second active agent is selected from gabapentin.

71. The composition of paragraph 70, wherein the amount of nabilone ranges from about 0.25 mg to about 6 mg and the amount of gabapentin ranges from about 300 mg to about 1200 mg.
72. The composition of paragraph 71, wherein the amount of nabilone is about 0.25 to about 6 mg and the amount of gabapentin is about 300 mg.
73. The composition of any of paragraphs 69-72, wherein the composition is in the form of a capsule.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

Examples of the compositions and methods of the invention appear in the following non-limiting Examples.

EXAMPLES

Example 1. Randomized, Placebo-Controlled, Crossover Pharmacokinetic and Pharmacodynamic Study of *Cannabis* Withdrawal Syndrome in Volunteers with *Cannabis* Use Disorder Treated with Nabilone and Gabapentin A combination of nabilone and gabapentin (PP-01) was administered to patients in a controlled clinical study.

Study Overview

The study evaluated the PK of PP-01 (nabilone and gabapentin) in participants with CUD. The study also assessed the safety and tolerability of PP 01 in participants with CUD; and the impact of PP-01 on *cannabis* withdrawal symptoms on these patients. Several assessment tools were utilized to evaluate the impact on withdrawal symptoms, particularly by comparing the treatment period (PP 01) to the placebo period utilizing:

*Cannabis* Withdrawal Scales (CWS (severity) and WBS (bothersomeness))
Patient Global Impression of Severity (PGI-S) of withdrawal symptoms
Clinician's Global Impression (CGI) of treatment
Sleep quantity and quality
Exploratory Objectives
To evaluate safety of PP-01 and its pharmacokinetics.
To evaluate the impact of PP-01 on withdrawal symptoms.
To assess change from within-participant change in serum cortisol levels between PP-01 and placebo.

This was a randomized, placebo-controlled, double-blind, two-period, parallel-group, cross-over Phase 1 study to evaluate the PK, safety, and PD of a fixed dose of PP-01 in a well-controlled, prospective inpatient and outpatient trial in volunteers with moderate to severe CUD. The placebo arm was included to help assess the incidence and severity of withdrawal symptoms in heavy long-term users of *cannabis*. Study procedures were the same for Periods 1 and 2.

A total of 14 eligible healthy volunteers with moderate to severe CUD and no contraindications to nabilone or gabapentin were randomized to receive PP-01 (nabilone and gabapentin; Test) or Placebo, in a 1:1 ratio, from a randomization table at the start of Period 1 (Day −1). If participants received PP-01 in Period 1, they received Placebo in Period 2; similarly, if participants received Placebo in Period 1, they received PP-01 in Period 2. Participants received oral doses of PP-01 or Placebo approximately 2 hours before a standardized meal on the morning on the second day of each inpatient admission (Day 1, Periods 1 and 2) and continued to receive once-daily dosing in the morning for a total of four doses per period.

A brief overview is provided below:

Period 1, Inpatient Visit 2

Inpatient Visit 2 included five overnight stays occurring from Day −1 with discharge from the inpatient unit on Day 5. Study drug dosing occurred on Days 1 to 4.

Participants were discharged from the research unit on Day 5 and returned to the research facility on Day 8 (Visit 3) for one outpatient PK blood draw and evaluation of withdrawal symptoms, and outpatient *cannabis* use utilizing the Log of *Cannabis* Use questionnaire. Participants then entered a 14-day washout period (14-day minimum with a maximum of 28 days). After the washout period, study participants returned to the research facility for Period 2 (Inpatient Visit 4). A schematic diagram of Period 1 of the study is outlined below.

On Day −1, participants arrived and were admitted to the research facility in the morning upon confirmation that study entry criteria were met. Participants were randomized to receive either PP-01 (nabilone and gabapentin; Test) or Placebo. A standardized lunch was served and blood for THC and THC metabolites was drawn and questionnaires (CWS, Sleep, PGI-S, and CGI) were completed, along with other safety assessments. Participants refrained from using any *cannabis*/cannabidiol (CBD) during the treatment periods; all self-*cannabis*/CBD products were prohibited from being brought into the research facility. Blood samples to assess serum cortisol were obtained in the evening.

On Day 1, the 0-hour PK blood draw was obtained within 30 minutes prior to the first dose of study drug which was administered by the Investigator (or a staff member as delegated by the Investigator) at approximately 120 minutes prior to the morning standardized breakfast. Venous blood samples of approximately 10 mL each were obtained at the following times following the Day 1 dose to assess nabilone and gabapentin concentrations: 30 and 60 minutes, and 2, 3, and 4 hours (within ±5 minutes of each time point), and 6, 8, 12, and 24 hours (within ±10 minutes of each time point) after study drug administration. The CWS was completed by participants prior to dosing (Baseline) and at 4- and 10-hours post-dose and the sleep questionnaire was completed in the morning prior to dosing. Blood samples to assess serum cortisol were obtained in the evening. Routine safety assessments were performed as scheduled.

Participants continued once daily dosing at the same time each morning, approximately 120 minutes before breakfast on Days 2 and 3. The PGI-S and CGI questionnaires were completed on Day 2 approximately 4 hours after dosing. On Days 2 and 3, the CWS was completed by participants prior to dosing and at 4- and 10-hours post-dose and the sleep questionnaire was completed in the morning prior to dosing. Routine safety assessments were performed as scheduled.

On Day 4, the 0-hour PK blood draw was obtained within 30 minutes prior to the dosing of study drug, which was administered by the Investigator (or a staff member as delegated by the Investigator) at approximately 120 minutes prior to the morning standardized breakfast. Venous blood samples of approximately 10 mL each were obtained at the following times following the Day 4 dose to assess nabilone and gabapentin concentrations: 30 and 60 minutes, and 2, 3, and 4 hours (within ±5 minutes of each time point), and 6, 8, 12, and 24 hours (within ±10 minutes of each time point) after study drug administration. The CWS was completed by participants prior to dosing and at 4- and 10-hours post-dose and the sleep questionnaire was completed in the morning prior to dosing; the PGI-S and CGI were completed approximately 4 hours after dosing. Blood samples to assess serum cortisol were obtained in the evening. Routine safety assessments were performed as scheduled.

After the last dose on Day 4, study participants entered a washout of PP-01 (nabilone and gabapentin) or Placebo period that lasted for at least 14 days (14-day minimum with a maximum of 28 days).

On Day 5, participants were discharged from the research facility after a brief physical examination (PE), assessment of vital signs, pulse oximetry, routine lab and PK draws, and completion of all questionnaires. Participants were provided with instructions to resume their usual activities and return to the facility on Day 8 as outpatients.

On Day 8, study participants were evaluated at the research facility where evaluation of *cannabis*, illicit drug or alcohol use and vital signs were assessed. Any ongoing adverse events or laboratory abnormalities were followed until resolved or until the participant returned to their clinical baseline.

Period 2, Inpatient Visit 4

On Day −1 (at least 14 days post last dose of PP-01 [nabilone and gabapentin] or Placebo on Day 4 in Period 1), study participants returned for readmission to the inpatient unit. Participants who continued to meet the inclusion and exclusion criteria, started Period 2, Visit 4 in which they were given the dose per the sequence to which the subject was randomized on Day −1, Period 1 (i.e., those participants who received PP-01 [Test] in Period 1 received Placebo in Period 2 and those who received Placebo in Period 1 received PP-01 [Test] in Period 2).

Procedures for Period 2 were the same as Period 1, described above. Study participants were discharged from the inpatient unit on Day 5 and returned to the research facility on Day 8 for a PK blood draw and evaluation. Participants were discharged from the study on Day 8, and any adverse events related to the study were followed until resolution.

Study participants received Placebo if they received PP-01 during Period 1 and those who received Placebo in Period 1 received PP-01, for a total of four doses in Period 2.

TABLE 1

Treatment Sequence

| Sequence | Period 1 | Period 2 |
|---|---|---|
| Sequence A | PP-01 | Placebo |
| Sequence B | Placebo | PP-01 |

Nabilone in this study was manufactured by Valeant Pharmaceuticals (now Bausch Health), gabapentin was manufactured by Pfizer, Inc.

Placebo participants were included to evaluate withdrawal symptoms, THC levels, and to evaluate whether there was a correlation between plasma/urinary levels of *cannabis* and the frequency of withdrawal symptoms in an inpatient setting.

The following PK assessments were assessed in Periods 1 and 2 on Day 1, Day 2 (trough), Day 4, Day 5 (trough), and Day 8 for nabilone and gabapentin. Baseline concentrations were defined as the 0-minute time point (within 30 minutes of dosing) on Day 1 (Periods 1 and 2).

Area under the plasma concentration-time curve from 0 to the last measurable concentration ($AUC_{0-t}$)

Area under the plasma concentration-time curve extrapolated to infinity ($AUC_{0-\infty}$)

Peak (maximum) plasma concentration of the drug ($C_{max}$)

Time to peak (maximum) plasma concentration ($t_{max}$)

Elimination half-life ($t_{1/2}$)

Venous blood samples of 10 ml each were collected with K2EDTA anticoagulant for Baseline levels of Δ-9-THC, 11-OHTHC and THC-COOH on Day −1 (Periods 1 and 2). For Periods 1 and 2, levels of nabilone and gabapentin were assessed following the time points listed in Table 2 following the first and fourth dose. Study participants returned on Day 8 (Periods 1 and 2) to have PK samples drawn to help determine the terminal half-life of nabilone. The Baseline (0-hour) time point was collected within 30 minutes prior to dosing.

Baseline concentrations of Δ-9-THC, 11-OHTHC and THC-COOH were determined using a validated liquid chromatographic-tandem mass spectroscopy (LC-MS/MS) assay with a lower limit of quantification (LLOQ) of 0.200 ng/mL. Nabilone and gabapentin concentrations were determined using a validated liquid chromatographic-tandem mass spectroscopy (LC-MS/MS) assay with a LLOQ of 25.0 pg/mL and 50.0 ng/mL, respectively.

TABLE 2

PK Sample Times

| Day 1 Periods 1 and 2 Time Points (hour:minutes) | Day 4 Periods 1 and 2 Time Points (hour:minutes) | Blood draw window (minutes or hours) |
|---|---|---|
| 00:00 | 00:00 | −30 to 0 minutes |
| 00:30 | 00:30 | ±5 minutes |
| 00:60 | 00:60 | ±5 minutes |
| 2:00 | 2:00 | ±5 minutes |
| 3:00 | 3:00 | ±5 minutes |
| 4:00 | 4:00 | ±5 minutes |
| 6:00 | 6:00 | ±10 minutes |
| 8:00 | 8:00 | ±10 minutes |
| 12:00 | 12:00 | ±10 minutes |
| 24:00 | 24:00 | ±10 minutes |
| — | 96:00 | ±8 hours |

Efficacy Assessments

The CWS and WBS asked about symptoms experienced over the last 24 hours. On Study Days −1 to 5 (Periods 1 and 2) and Study Day 8 (Periods 1 and 2), participants completed the CWS multiple times throughout the day on Days 1 to 4 (pre-dose and 4- and 10-hours post-dose) of Periods 1 and 2, and once on Day −1, 5, and 8; their responses reflected how they felt since the last time the questionnaire was completed. The CWS and WBS were administered by the reviewer.

The WBS, in particular, assessed how bothered participants were by their *cannabis* withdrawal symptoms. For the CWS (Allsop et al., *Drug and Alcohol Dependence* 119(1-2):123-129 (2011)) scale, CWS, the responses to the 19 items were based on an 11-point severity scale, from 0=not at all to 10=extremely, and participant responses reflected how they felt over the last 24 hours. For the, WBS, the responses to the same 19 items were based on a 5-point bothersomeness scale, from 0=not bothered at all to 4=very severely bothered, and participant responses reflected how bothered they felt over the last 24 hours.

Withdrawal symptoms were also assessed using a six question subscale (determined both with the severity and bothersomeness scales) consisting of the following rating questions from the 19-Question *Cannabis* Withdrawal Scale (Q. The only thing I could think about was smoking *cannabis*; Q. I had no appetite; Q. I had been imagining being stoned; Q. I felt restless; Q. I woke up early; and Q. I had trouble getting to sleep at night).

In addition, AUC type of analyses across all time points were performed.

A sleep questionnaire was administered each morning and assessed problems that affected the quality and amount of sleep from the previous night and wakefulness each morning. This questionnaire referred to sleep over the past 24 hours.

Study participants were instructed to describe the severity of their *cannabis* withdrawal symptoms and how bothered they were by their symptoms. The PGI-S was assessed on Days −1 (Baseline) and Days 2 and 4, approximately 4 hours post-dose.

The Principal Investigator assessed whether the participants appeared to be experiencing withdrawal symptoms given their experience of observing withdrawal symptoms (CGI assessment). The CGI was assessed on Days −1 (Baseline) and Days 2 and 4, approximately 4 hours post-dose.

Evening cortisol was assessed to serve as a physiological marker of stress associated with withdrawal. Serum cortisol was drawn in the evening at the time of the last PK sample on designated days.

Food intake was assessed using log participant consumption percentage (100%, 75%, 50%, 25%, 0%) on site meal logs. Additionally, the start and end time of meals was collected.

Body weight, in kilograms, was to be obtained daily with participants' shoes off, and jacket or coat removed.

PK Analysis of Nabilone and Gabapentin

The analysis was based on a mixed models repeated measurements (MMRM) analysis of variance where treatment arm is fixed using only data from active treatment and not placebo, participant (subject) is a random effect, intercept is considered random and the variance-covariance matrix is unstructured, Sequence Group AB vs BA (ARMCD) and DAY (Day 1 vs Day 4) are fixed effects, and ARMCD*DAY is the one possible interaction term. Age and Baseline concentrations may again be considered covariates.

Efficacy analyses were performed on the ITT and Efficacy Populations. The analysis of each of the efficacy parameters shall be based on a MMRM analysis of variance where participant is a random effect, intercept is considered random and the variance-covariance matrix is unstructured, treatment arm (PP-01 vs placebo), Sequence Group AB vs BA (ARMCD) and TIMEPT (multiple fixed time points are designated for each efficacy endpoint and may be different for different endpoints) are fixed effects, and possible interaction terms. Age and Baseline values were evaluated as covariates. The efficacy parameter (ADEFFPAR) was evaluated by change from Baseline. The efficacy parameter is the observed value at each time point and not the change from Baseline.

Descriptive analyses were performed on the administered questionnaires (CWS and WBS, PGI-S, CGI, and Sleep) and weight, food intake, and serum cortisol to summarize efficacy results by treatment status (i.e., under PP-01 treatment vs Placebo treatment). Analysis of variance tests of hypothesis were performed to compare efficacy results under PP-01 treatment vs Placebo treatment in this crossover design. In addition, efficacy result differences between Period 1 and Period 2 sequence groups were evaluated and summarized. In addition, AUC type of analyses across all time points were performed.

Evening serum cortisol levels and changes from Baseline in cortisol levels are summarized by day of withdrawal and by treatment status (i.e., under PP-01 treatment vs Placebo treatment).

Food intake was assessed using a food intake log of participant consumption percentage (100%, 75%, 50%, 25%, 0%) of on-site meal logs. Additionally, the start and end time of meals were collected.

Food intake was summarized by day of withdrawal and by treatment status (i.e., under PP-01 treatment vs Placebo treatment).

Body weight was obtained daily with participants' shoes off, and jacket or coat removed. Body weight and change in body weight from period Baseline was examined.

Study Patients

A total of 43 participants were screened for the study; 29 were screen failures and 14 were randomized at a single site (AltaSciences Kansas). Fourteen participants were enrolled and randomized to the sequence of PP-01 or Placebo with seven participants in each group. The first participant screened was on 4 Sep. 2020 and the last participant was enrolled on 1 Oct. 2020. Arm AB received active treatment (PP-01) in Period 1 and Arm BA received active treatment (PP-01) in Period 2. All participants completed Period 1. Two participants did not complete Period 2; one participant (01-020) in the active treatment arm did not return for Period 2 (placebo) and was lost to follow-up and one participant (01-029) in the placebo arm was discontinued by the Sponsor due to a positive urine drug screen (benzodiazepines) on Day −1, Period 2.

As required for study entry, all participants had ongoing CUD. Participants in this study had to be near daily users of *cannabis* with a report of 6 days per week on average of *cannabis* use for at least 6 months and using 1.0 gram or equivalent or greater per day by self-report. The mean age of first use of *cannabis* use was 14 years (range 6 to 22 years) and mean duration of use was 17 years (range 4 to 31 years).

Figure 3:
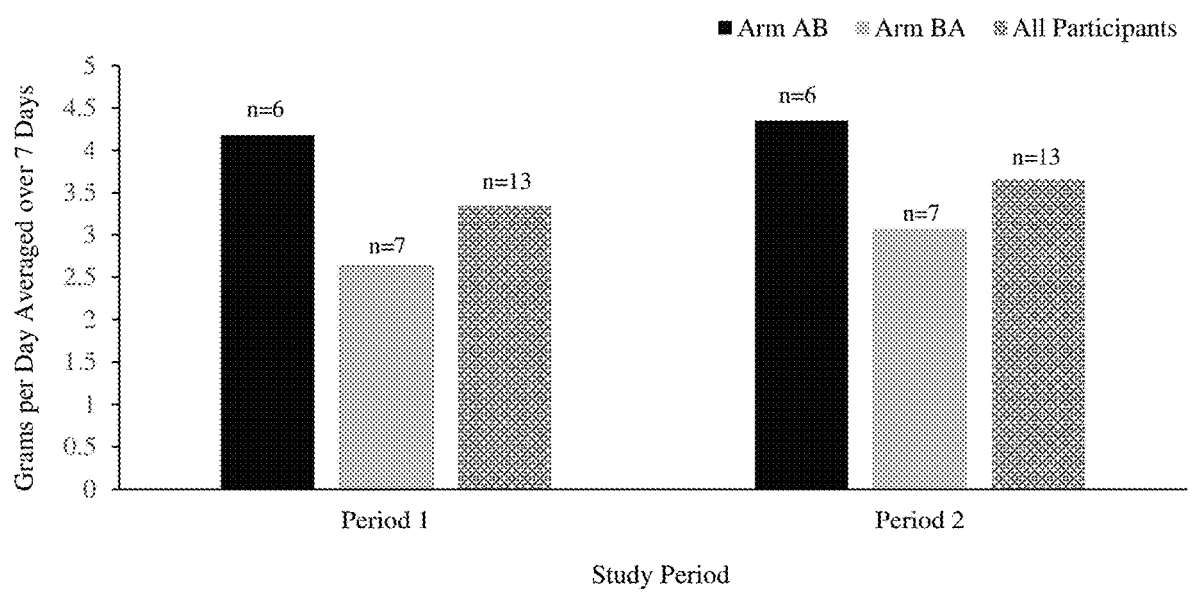
FIG. 3. Clinical Study—Subject *Cannabis* use for seven days prior to first dose in each period (safety population).

The amount of *cannabis* used seven days prior to first dose of study drug for Periods 1 and 2 was captured by daily diary. The averaged use of *cannabis* over the 7 days prior to dosing in Periods 1 and 2 was similar for Arms AB and BA (FIG. 3). Arm AB on average used more *cannabis* than BA but each arm was consistent in their use between periods. The mean daily *cannabis* use for all participants was 3.35 grams prior to Period 1 and 3.66 grams prior to Period 2. Six participants did not use *cannabis* on Day −1, Period 1 and two did not use on Day −1 and Day −2, Period 1, although this did not impact the study's findings or conclusions. Following instructions from site personnel all participants in Period 2 used *cannabis* on Day −1.

All participants enrolled in the study met the criteria for moderate or severe CUD per the DSM-5 (Table 3) and reported having withdrawal symptoms when previously trying to discontinue *cannabis*. A summary of results for DSM-5 criteria for determination of severity is provided in Table 4.

TABLE 3

DSM-5 CUD Severity

| Severity | Arm AB (N = 7) | Arm BA (N = 7) | All Participants (N = 14) |
| --- | --- | --- | --- |
| Moderate (presence of 4-5 criteria) | 4 (57.1) | 1 (14.3) | 5 (35.7) |
| Severe (presence of 6 or more criteria) | 3 (42.9) | 6 (85.7) | 9 (64.3) |

Abbreviations:
CUD = cannabis use disorder

TABLE 4

DSM-5 Criteria for Severity Assessment

| Criteria, n (%) | Arm AB (N = 7) | Arm BA (N = 7) | All Participants (N = 14) |
| --- | --- | --- | --- |
| Characteristic withdrawal syndrome for the substance; or the substance is taken to relieve or avoid withdrawal symptoms | | | |
| Yes | 7 (100) | 7 (100) | 14 (100) |
| Craving, or a strong desire or urge to use cannabis | | | |
| Yes | 7 (100) | 7 (100) | 14 (100) |
| Need for markedly increased amounts of the substance to achieve intoxication or desired effect; or diminished effect with continued use of the same amount | | | |
| Yes | 7 (100) | 6 (85.7) | 13 (92.9) |
| No | 0 (0) | 1 (14.3) | 1 (7.1) |
| Great deal of time spent obtaining, using, or recovering from the effects of cannabis | | | |
| Yes | 5 (71.4) | 6 (85.7) | 11 (78.6) |
| No | 2 (28.6) | 1 (14.3) | 3 (21.4) |
| Persistent desire or unsuccessful effort to cut down or control use | | | |
| Yes | 3 (42.9) | 6 (85.7) | 9 (64.3) |
| No | 4 (57.1) | 1 (14.3) | 5 (35.7) |
| The substance is taken in larger amounts or over a longer period than was intended | | | |
| Yes | 4 (57.1) | 4 (57.1) | 8 (57.1) |
| No | 3 (42.9) | 3 (42.9) | 6 (42.9) |
| Continued use despite having persistent or recurrent social or interpersonal problems caused by or exacerbated by the effects of use | | | |
| Yes | 2 (28.6) | 3 (42.9) | 5 (35.7) |
| No | 5 (71.4) | 4 (57.1) | 9 (64.3) |
| Giving up or reducing important social, occupational, or recreational activities because of use | | | |
| Yes | 1 (14.3) | 3 (42.9) | 4 (28.6) |
| No | 6 (85.7) | 4 (57.1) | 10 (71.4) |
| Recurrent use in situations that could be physically hazardous | | | |
| Yes | 1 (14.3) | 3 (42.9) | 4 (28.6) |
| No | 6 (85.7) | 4 (57.1) | 10 (71.4) |
| Recurrent use resulting in failure to fulfill major obligations at work, school, or home | | | |
| Yes | 2 (28.6) | 1 (14.3) | 3 (21.4) |
| No | 5 (71.4) | 6 (85.7) | 11 (78.6) |
| Continued use despite knowledge of having a persistent or recurrent physical or psychological problem caused by or exacerbated by use | | | |
| Yes | 2 (28.6) | 1 (14.3) | 3 (21.4) |
| No | 5 (71.4) | 6 (85.7) | 11 (78.6) |

Pharmacokinetics Results

Figure 4:
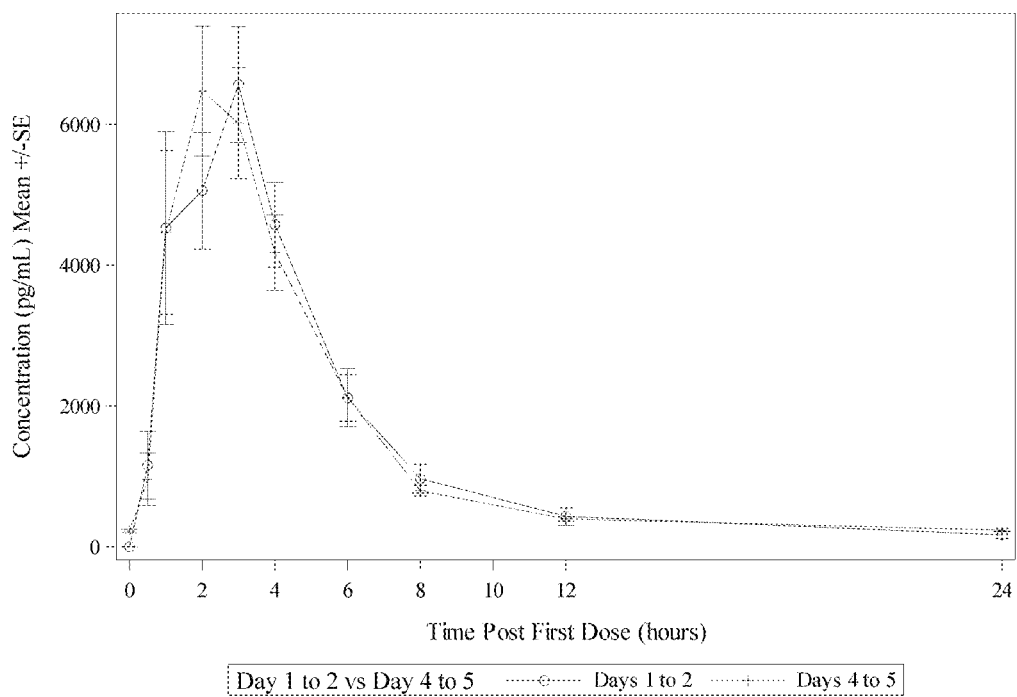
FIG. 4. Clinical Study—Mean nabilone concentrations vs time (PK population).
Figure 5:
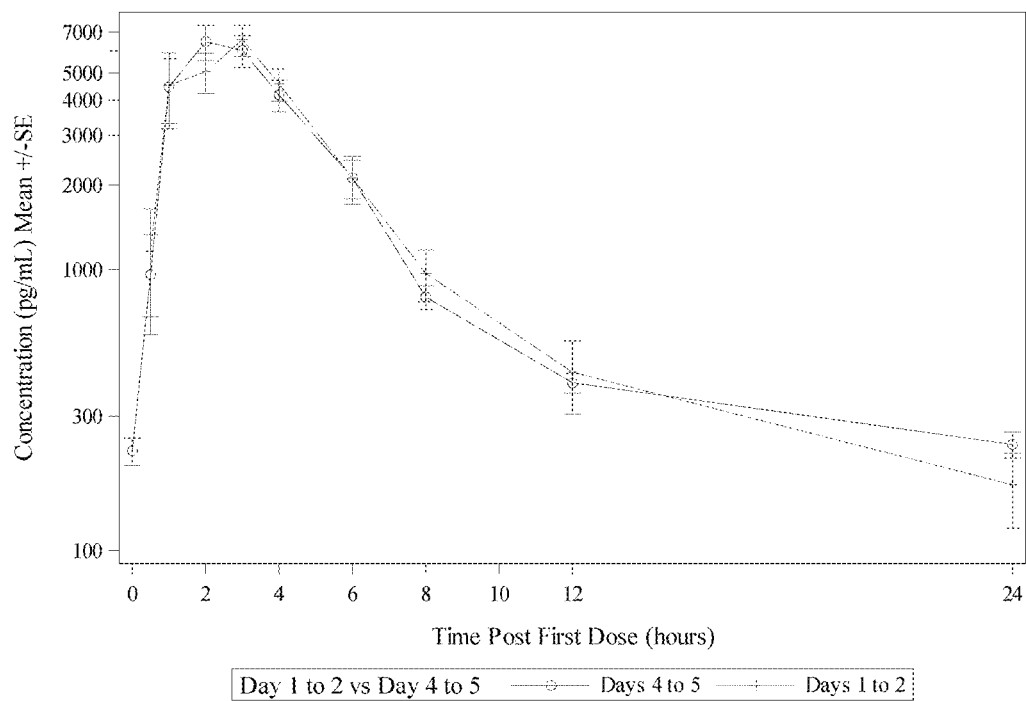
FIG. 5. Clinical Study—Log-transformed mean nabilone concentrations vs time (PK population).

The LLOQ of the LC-MS/MS assay for nabilone is 25.0 pg/mL. Calculations were based on periods of active treatment and do not include Placebo treatment. Concentration-time profiles of nabilone by day for all sequences combined is shown on a linear-linear scale in FIG. 4 and a log-linear scale in FIG. 5.

As shown in the figures, data for Days 1 to 2 and Days 4 to 5 were not different, and no accumulation occurred. The mean time to maximal concentration ($T_{max}$) was reached by approximately 2.5 hours.

Figure 6:
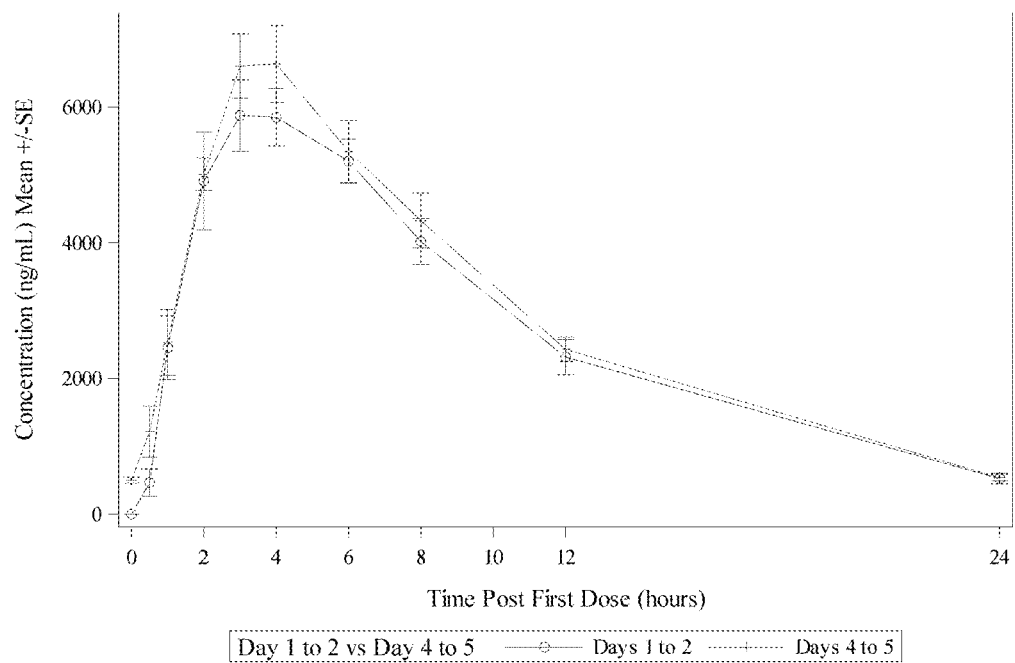
FIG. 6. Clinical Study—Mean gabapentin concentrations vs time for arm AB (PK population).
Figure 7:
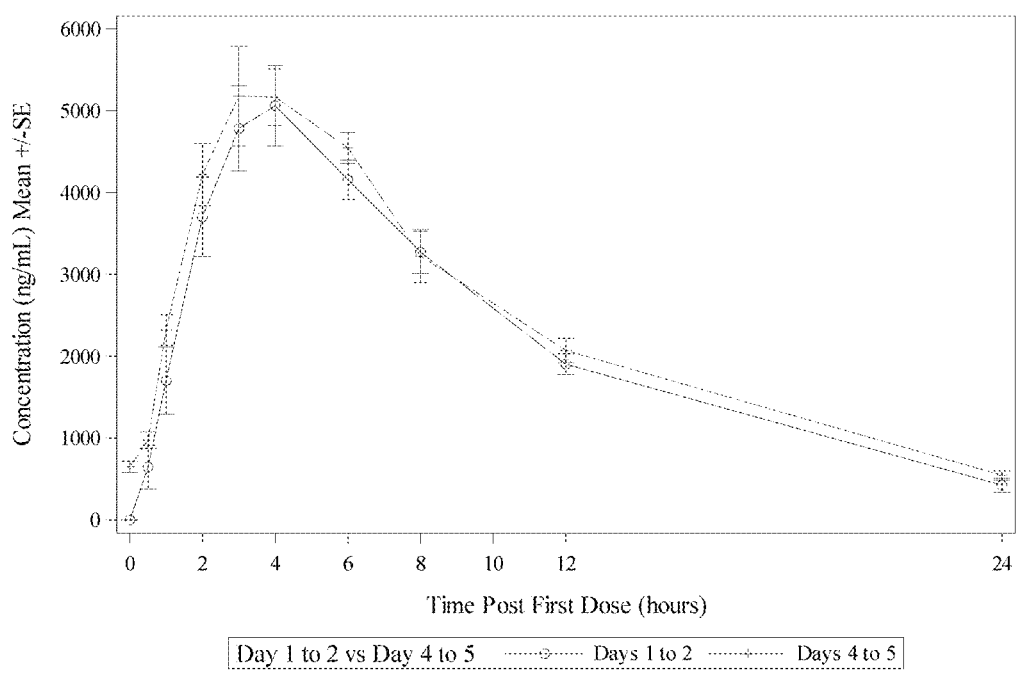
FIG. 7. Clinical Study—Mean gabapentin concentrations vs time for arm BA (PK population).
Figure 8:
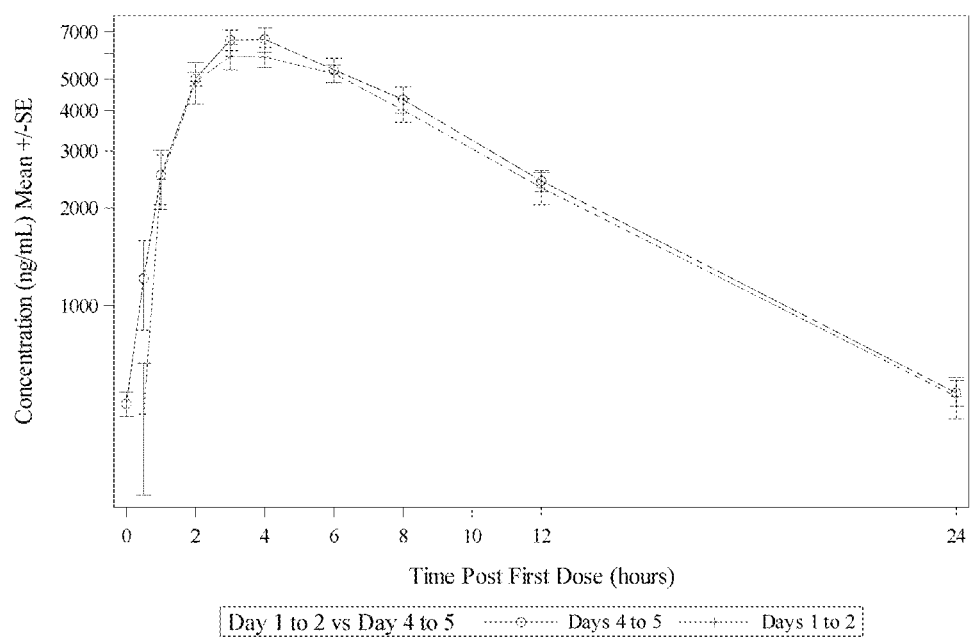
FIG. 8. Clinical Study—Log-transformed mean gabapentin concentrations vs time for arm AB (PK population).
Figure 9:
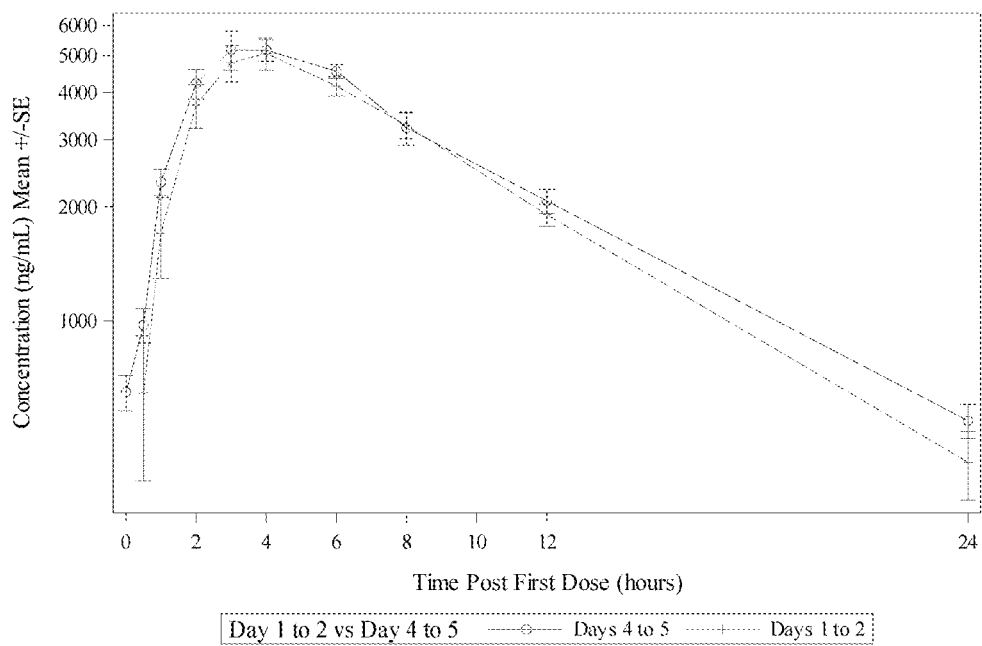
FIG. 9. Clinical Study—Log-transformed mean gabapentin concentrations vs time for arm BA (PK population).

The LLOQ of the LC-MS/MS assay for gabapentin is 50.0 ng/mL. Calculations were based on periods of active treatment and do not include Placebo treatment. Concentration-time profiles on a linear-linear scale for gabapentin by days are shown for Sequence Arm AB in FIG. 6 and for Sequence Arm BA in FIG. 7. The mean $T_{max}$ is reached between 3.3 to 4.0 hours across days and sequences.

The PK parameters for plasma nabilone by day for all sequences combined are summarized below in Table 5. Mean exposure metrics, $C_{max}$, $AUC_{0-24}$, and $AUC_{0-\infty}$, are consistent across treatment days indicating that there is minimal accumulation over the period studied. Moderate between subject variability was observed across parameters.

The mean PK parameters for plasma gabapentin by sequence and by days are summarized below in Table 6. There was an apparent impact of sequence, as well as time, on exposure metrics, $C_{max}$, $AUC_{0-24}$, and $AUC_{0-\infty}$, with exposure slightly increased at Days 4 to 5 compared to Days 1 to 2, and a general increase in exposure for Sequence AB in comparison to Sequence BA. These differences were minimal and were within the variance of each measure. The mean $t_{1/2}$ ranged across treatment from 5.3 to 6.3 hours with no differences seen across days or sequence. Low to moderate between subject variability was observed across parameters.

TABLE 5

Nabilone PK Parameter Summary Statistics by Days for Both Sequences (PK Population)

| | | | PK Parameters Arithmetic Mean ± SD (% CV) | | | | |
|---|---|---|---|---|---|---|---|
| Days (all sequences) | N | Dose (mg) | $T_{max}$ (hr) | $C_{max}$ (pg/mL) | $AUC_{0-24}$ (pg · hr/mL) | $AUC_{0-\infty}$ (pg · hr/mL) | $t_{1/2}$ (hr) |
| 1-2 | 13 | 6 | 2.5 ± 1.5 (57.1) | 8505.8 ± 3576.2 (42.0) | 34095.9 ± 11672.9 (34.2) | 35835.4 ± 11947.8 (33.3) | 6.4 ± 1.7 (27.2) |
| 4-5 | 13 | 6 | 2.3 ± 0.9 (41.1) | 8588.2 ± 2981.7 (34.7) | 33870.5 ± 11169.9 (33.0) | 37414.6 ± 12712.1 (34.0) | 9.9 ± 2.5 (25.8) |

Abbreviations: PK = pharmacokinetic; SD = standard deviation; $AUC_{0-24\,hr}$ = area under the concentration-time curve from zero to 24 hours; $AUC_{0-\infty}$ = area under the concentration-time curve from zero to infinity; $C_{max}$ = maximum concentration; $t_{1/2}$ = terminal elimination half-life; $T_{max}$ = time to maximum concentration
Note:
data were rounded using five significant figures, when possible.

TABLE 6

Gabapentin PK Parameter Summary Statistics by Sequence and by Days (PK Population)

| | | | | PK Parameters Arithmetic Mean ± SD (% CV) | | | | |
|---|---|---|---|---|---|---|---|---|
| Sequence | Days (all sequences) | N | Dose (mg) | $T_{max}$ (hr) | $C_{max}$ (pg/mL) | $AUC_{0-24}$ (pg · hr/mL) | $AUC_{0-\infty}$ (pg · hr/mL) | $t_{1/2}$ (hr) |
| AB | 1-2 | 7 | 600 | 3.7 ± 1.1 (30.0) | 6075.5 ± 1276.9 (21.0) | 65725.1 ± 14424.7 (21.9) | 69986.1 ± 15651.6 (22.4) | 5.4 ± 0.7 (13.6) |
| | 4-5 | 7 | 600 | 3.3 ± 0.8 (23.0) | 7008.7 ± 1201.9 (17.1) | 70518.8 ± 11686.8 (16.6) | 74930.6 ± 11242.5 (15.0) | 5.5 ± 1.1 (19.4) |
| BA | 1-2 | 6 | 600 | 3.7 ± 0.5 (14.1) | 5173.7 ± 1247.5 (24.1) | 53579.7 ± 9273.4 (17.3) | 57198.0 ± 10279.2 (18.0) | 5.3 ± 1.5 (28.2) |
| | 4-5 | 6 | 600 | 1.0 ± 1.1 2.0 (27.4) | 5509.5 ± 1253.2 (22.7) | 58145.6 ± 6215.3 (10.7) | 63133.4 ± 7105.2 (11.3) | 6.3 ± 0.6 (9.8) |

Abbreviations: PK = pharmacokinetic; SD = standard deviation; $AUC_{0-24\,hr}$ = area under the concentration-time curve from zero to 24 hours; $AUC_{0-\infty}$ = area under the concentration-time curve from zero to infinity; $C_{max}$ = maximum concentration; $t_{1/2}$ = terminal elimination half-life; $T_{max}$ = time to maximum concentration
Note:
data were rounded using five significant figures, when possible.

Baseline measurement of THC and THC metabolites were generally not different between Periods 1 and 2.

Pharmacokinetics of nabilone revealed the mean $T_{max}$ to be at approximately 2.5 hours with minimal accumulation during the study period, as evidence by consistent mean exposure metrics across treatment days. There was no apparent impact of sequence on PK parameters and data were combined for each sequence and presented by day. Moderate between subject variability was observed across parameters.

The mean $T_{max}$ for gabapentin was reached between 3.3 and 4.0 hours across all days and both sequences. There was an apparent impact of sequence, as well as time, on exposure metrics, with exposure slightly increased at Days 4 to 5 compared to Days 1 to 2, and a general increase in exposure for Sequence AB in comparison to Sequence BA. These differences were minimal and were within the variance of each measure. Mean $t_{1/2}$ ranged from 5.3 to 6.3 hours with no difference since across days or sequence. The $AUC_{0-24}$ ranged from 53580 to 70519. The between subject variability was low to moderate. Of interest is the pharmacodynamic effect that was sustained over the 24-hour period between dosing consistent with the AUC being similar to the reported extended-release gabapentin.

Pharmacokinetics of nabilone and gabapentin were consistent with historical controls and each agent did not appear to have an impact on the PK of the other. The pharmacodynamic effect was observed despite the relatively short half-lives of each compound which should permit.

Efficacy Results

CWS

The Total CWS Score equals the numerical sum total of all 19 questions, with a maximum score of 190 (most impacted by withdrawal symptoms). As shown in Table 7, there were no statistically significant differences between the PP-01 and Placebo groups prior to dosing.

Eight participants did not use *cannabis* on Day −1, Period 1 and two did not use on Day −2, Period 1. For Period 2, all participants used *cannabis* on Day −1.

One participant (01-029) had Period 2, Day −1 CWS data before being discontinued for a positive urine drug screen for benzodiazepines and is included in the analyses. CWS data are only missing for one participant (01-020), who did not return for Period 2 and was lost to follow-up.

TABLE 7

CWS Total Score for Day −1 and Day 1 (Pre-Dose) (ITT Population)

| Study Day/Parameter | PP-01 (N = 14) | Placebo (N = 14) | P-value (Paired t-test) |
|---|---|---|---|
| Day −1 (n) | 14 | 13 | 13 |
| Mean (SD) | 21.9 (25.57) | 29.4 (31.10) | 0.3439 |
| Median | 19.0 | 18.0 | — |
| Min, Max | 0.0, 69.0 | 0.0, 112.0 | — |
| Baseline, Day 1, 0 hour (n) | 13 | 13 | 12 |
| Mean (SD) | 47.6 (32.94) | 50.9 (20.52) | 0.8911 |
| Median | 48.0 | 51.0 | — |
| Min, Max | 0.0, 119.0 | 21.0, 96.0 | — |

Figure 10:
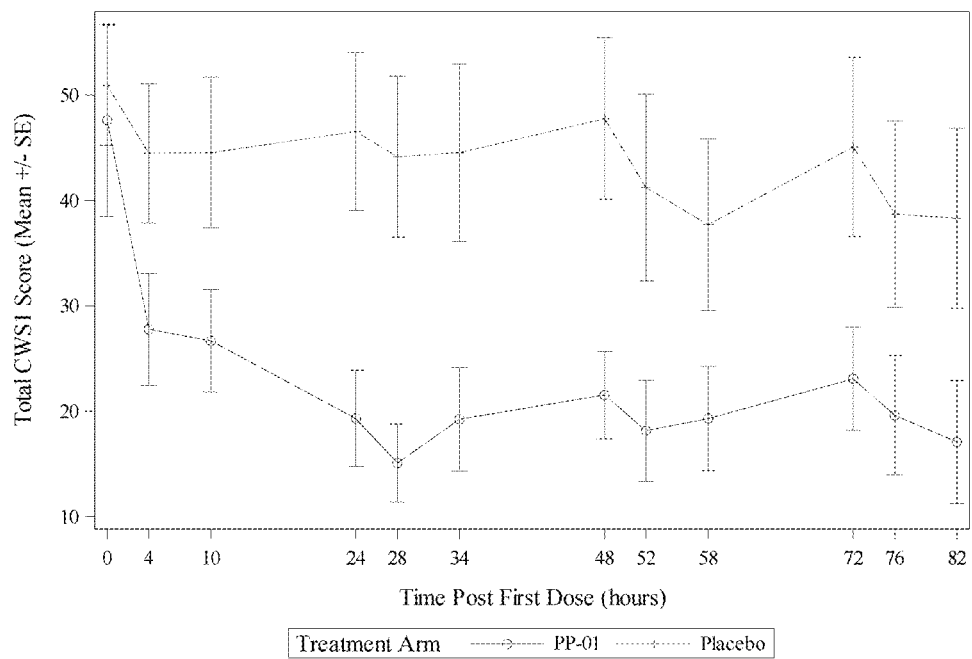
FIG. 10. Clinical Study—Mean total CWS score by time point: PP-01 vs placebo (ITT population).

Abbreviations:
ITT = intent to treat;
SD = standard deviation;
Min = minimum;
Max = maximum As shown in FIG. 10, all post-dose differences for Days 1 to 4 between PP-01 and Placebo were statistically significantly different; as noted above, there were no statistically significant differences prior to the first dose.

At Day 5, mean Total CWS Scores continued to be statistically significantly higher in the Placebo group as compared to the PP-01 group (46.4 vs 21.5, respectively, P=0.0207). Statistical significance was observed from the first measured timepoint at 4 hours on Day 1 and was sustained throughout the 5 inpatient days. By Day 8, when the participants were outpatients and were to be using *cannabis*, there were no longer statistically significant mean differences between the groups (18.0 vs 14.5, respectively, P=0.3764).

Figure 11:
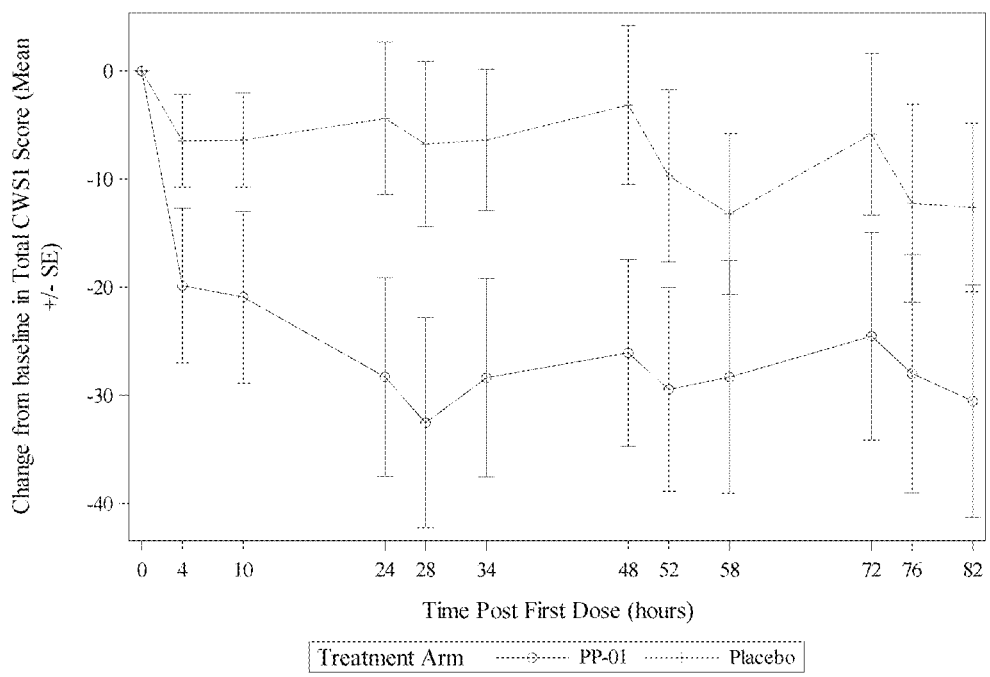
FIG. 11. Clinical Study—LS mean change from baseline in mean total CWS score by time point—PP-01 vs placebo (ITT population).
Figure 12:
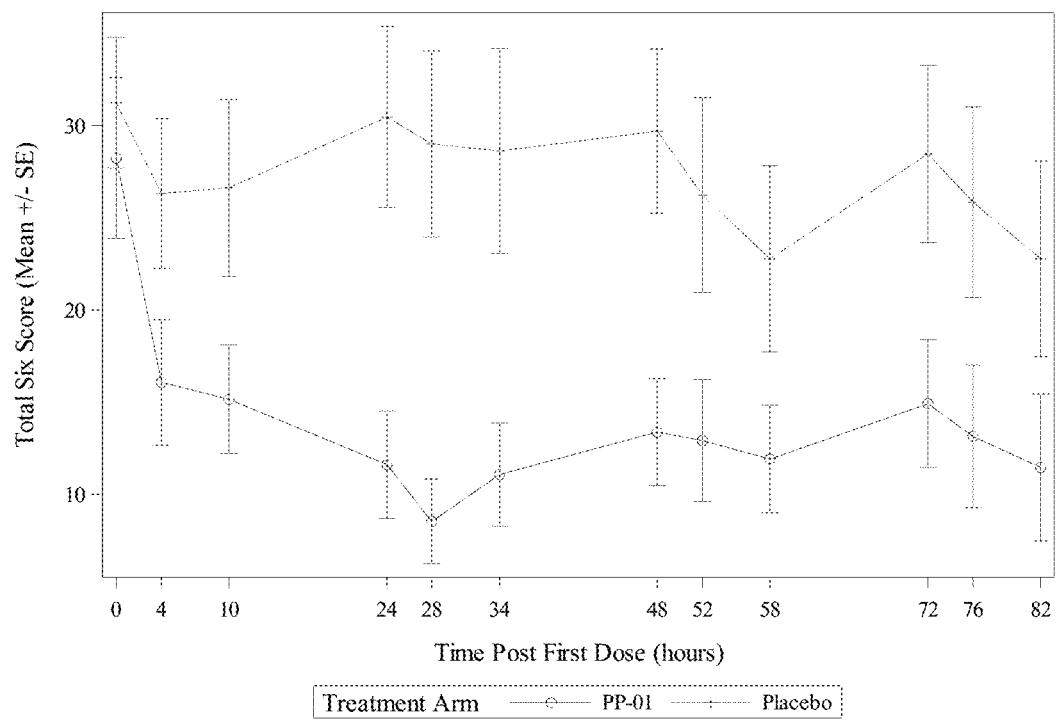
FIG. 12. Clinical Study—Mean total CWS six item subscale score by time point: PP-01 vs placebo (ITT population).
Figure 13:
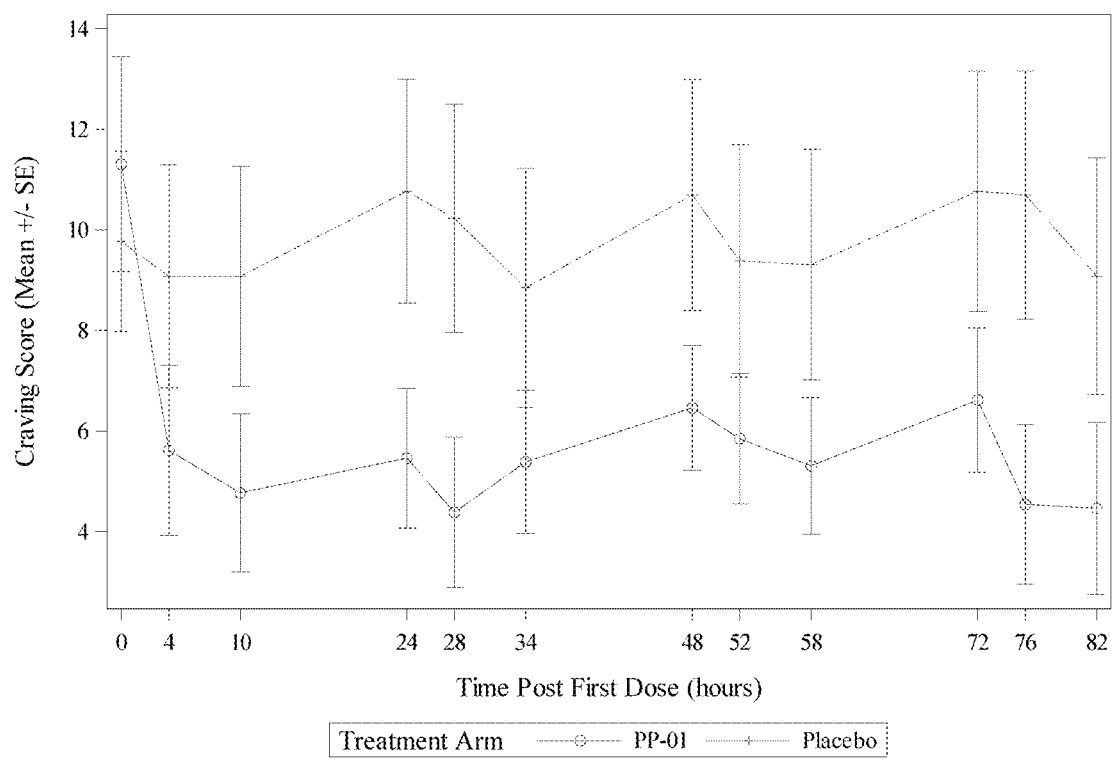
FIG. 13. Clinical Study—Mean total CWS cravings subscale score by Time point: PP-01 vs placebo (ITT population).
Figure 14:
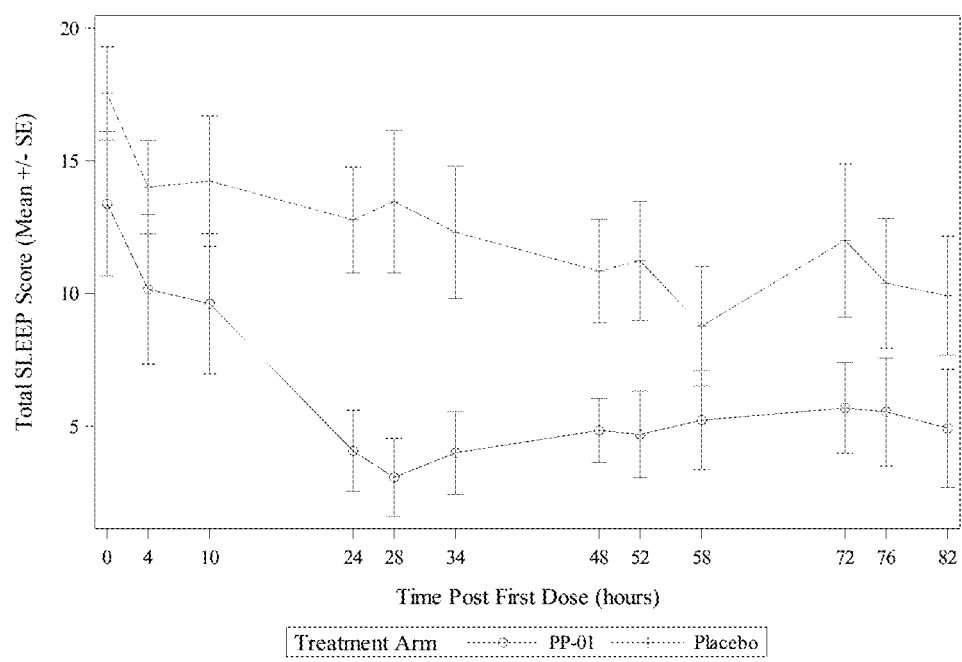
FIG. 14. Clinical Study—Mean total sleep score by time point: PP-01 vs placebo (ITT population).

The Least Square (LS) Mean Difference and standard error (SE) of PP-01 minus Placebo Change from Baseline at different time points is shown in FIG. 11 and is summarized in Table 8, along with MMRM P-values.

TABLE 8

LS Mean Difference Between PP-01 and Placebo in CWS Total Score for Periods 1 and 2 (ITT Population)

| | LS Mean Difference (SE) PP-01 Minus Placebo | MMRM P-value |
|---|---|---|
| Day 1, 4 hours post-dose | −12.79 (6.840) | 0.0642 |
| Day 1, 10 hours post-dose | −15.87 (6.840) | 0.0222 |
| Day 2, Pre-dose | −25.95 (6.840) | 0.0002 |
| Day 2, 4 hours post-dose | −28.95 (6.840) | 0.0000 |
| Day 2, 10 hours post-dose | −23.45 (6.840) | 0.0009 |
| Day 3, Pre-dose | −24.79 (6.840) | 0.0004 |
| Day 3, 4 hours post-dose | −22.87 (6.840) | 0.0011 |
| Day 3, 10 hours post-dose | −19.29 (6.840) | 0.0057 |
| Day 4, Pre-dose | −21.70 (6.840) | 0.0020 |
| Day 4, 4 hours post-dose | −21.12 (6.840) | 0.0026 |
| Day 4, 10 hours post-dose | −22.04 (6.840) | 0.0017 |

Abbreviations: ITT = intent to treat;
LS = least square;
SE = standard error;
MMRM = mixed models repeated measurements

TABLE 9

LS Mean Change from Baseline and Placebo in CWS Total Score for Periods 1 and 2 (ITT Population)

| | LS Mean Difference (SE) PP-01 Minus Placebo Change from Baseline | MMRM P-value |
|---|---|---|
| Day 1, 4 hours post-dose | −11.78 (8.710) | 0.1789 |
| Day 1, 10 hours post-dose | −14.87 (8.710) | 0.0907 |
| Day 2, Pre-dose | −24.95 (8.710) | 0.0050 |
| Day 2, 4 hours post-dose | −27.95 (8.710) | 0.0017 |
| Day 2, 10 hours post-dose | −22.45 (8.710) | 0.0113 |
| Day 3, Pre-dose | −23.78 (8.710) | 0.0074 |
| Day 3, 4 hours post-dose | −21.87 (8.710) | 0.0135 |
| Day 3, 10 hours post-dose | −18.28 (8.710) | 0.0381 |
| Day 4, Pre-dose | −20.70 (8.710) | 0.0192 |
| Day 4, 4 hours post-dose | −20.12 (8.710) | 0.0228 |
| Day 4, 10 hours post-dose | −21.03 (8.710) | 0.0174 |

Abbreviations: ITT = intent to treat;
LS = least square;
SE = standard error;
MMRM = mixed models repeated measurements The results above include Periods 1 and 2. Analyses were also conducted on CWS for Period 1 that included only seven participants in each arm. As shown below in Table 10, all post-dose differences were statistically significantly different with as few as seven participants per arm.

TABLE 10

LS Mean Change from Baseline and Placebo in
CWS Total Score for Period 1 (ITT Population)

| | LS Mean Difference (SE) PP-01 Minus Placebo Change from Baseline | MMRM P-value |
|---|---|---|
| Day 1, 4 hours post-dose | −22.50 (10.286) | 0.0307 |
| Day 1, 10 hours post-dose | −26.50 (10.286) | 0.0112 |
| Day 2, Pre-dose | −30.07 (10.286) | 0.0041 |
| Day 2, 4 hours post-dose | −35.64 (10.286) | 0.0007 |
| Day 2, 10 hours post-dose | −31.64 (10.286) | 0.0026 |
| Day 3, Pre-dose | −22.79 (10.286) | 0.0286 |
| Day 3, 4 hours post-dose | −26.21 (10.286) | 0.0121 |
| Day 3, 10 hours post-dose | −24.93 (10.286) | 0.0169 |
| Day 4, Pre-dose | −22.21 (10.286) | 0.0328 |
| Day 4, 4 hours post-dose | −23.07 (10.286) | 0.0267 |
| Day 4, 10 hours post-dose | −24.50 (10.286) | 0.0188 |

Abbreviations: ITT = intent to treat;
LS = least square;
SE = standard error;
MMRM = mixed models repeated measurements CWS—Six Item Subscale Score Prior to unblinding and based upon most commonly cited CWS symptoms, six items from the 19-item CWS were combined to form a subscale. The Total CWS Six Item Subscale Score equals the numerical sum of six questions from the CWS questionnaire, for a maximum total of 60. The six questions included: 1) The only thing I could think about was smoking *cannabis;* 2) I had no appetite; 3) I had been imagining being stoned; 4) I felt restless; 5) I woke up early; and 6) I had trouble getting to sleep at night. Total CWS Six Item Subscale Scores and the differences between PP-01 and Placebo are shown below in FIG. 12 and summarized in Table 11. As shown below, statistically significant differences between PP-01 and Placebo were observed at all time points.

TABLE 11

LS Mean Difference Between PP-01 and Placebo in Total
CWS Six Item Subscale Score (ITT Population)

| | LS Mean Difference (SE) PP-01 Minus Placebo | MMRM P-value |
|---|---|---|
| Day 1, 4 hours post-dose | −9.77 (2.852) | 0.0009 |
| Day 1, 10 hours post-dose | −12.02 (2.852) | 0.0001 |
| Day 2, Pre-dose | −18.02 (2.852) | 0.0000 |
| Day 2, 4 hours post-dose | −20.93 (2.852) | 0.0000 |
| Day 2, 10 hours post-dose | −16.93 (2.852) | 0.0000 |
| Day 3, Pre-dose | −15.77 (2.852) | 0.0000 |
| Day 3, 4 hours post-dose | −13.93 (2.852) | 0.0000 |
| Day 3, 10 hours post-dose | −12.10 (2.852) | 0.0000 |
| Day 4, Pre-dose | −13.85 (2.852) | 0.0000 |
| Day 4, 4 hours post-dose | −14.85 (2.852) | 0.0000 |
| Day 4, 10 hours post-dose | −13.10 (2.852) | 0.0000 |

Abbreviations: ITT = intent to treat;
LS = least square;
SE = standard error;
MMRM = mixed models repeated measurements CWS—Cravings Subscale Score The Total CWS1 Cravings Subscale Score equals the numerical sum of two questions from the CWS questionnaire, for a maximum total of 20. The two questions included: 1) The only thing I could think about was smoking *cannabis*; and 2) I had been imagining being stoned. Total CWS Cravings Subscale Scores are summarized below in Table 13. As shown below, statistically significant differences between PP-01 and Placebo were observed at all time points.

TABLE 12

LS Mean Difference Between PP-01 and Placebo in Total
CWS Cravings Subscale Score (ITT Population)

| | LS Mean Difference (SE) PP-01 Minus Placebo | MMRM P-value |
|---|---|---|
| Day 1, 4 hours post-dose | −3.04 (1.703) | 0.0766 |
| Day 1, 10 hours post-dose | −4.63 (1.703) | 0.0076 |
| Day 2, Pre-dose | −4.79 (1.703) | 0.0058 |
| Day 2, 4 hours post-dose | −5.96 (1.703) | 0.0007 |
| Day 2, 10 hours post-dose | −3.13 (1.703) | 0.0689 |
| Day 3, Pre-dose | −4.21 (1.703) | 0.0149 |
| Day 3, 4 hours post-dose | −3.88 (1.703) | 0.0247 |
| Day 3, 10 hours post-dose | −4.29 (1.703) | 0.0131 |
| Day 4, Pre-dose | −3.88 (1.703) | 0.0247 |
| Day 4, 4 hours post-dose | −6.96 (1.703) | 0.0001 |
| Day 4, 10 hours post-dose | −5.54 (1.703) | 0.0015 |

Abbreviations: ITT = intent to treat;
LS = least square;
SE = standard error;
MMRM = mixed models repeated measurements

TABLE 13

Change from Baseline and Placebo in Total CWS
Cravings Subscale Score (ITT Population)

| | LS Mean Difference (SE) PP-01 Minus Placebo Change from Baseline | MMRM P-value |
|---|---|---|
| Day 1, 4 hours post-dose | −5.38 (2.275) | 0.0198 |
| Day 1, 10 hours post-dose | −6.97 (2.275) | 0.0028 |
| Day 2, Pre-dose | −7.13 (2.275) | 0.0022 |
| Day 2, 4 hours post-dose | −8.30 (2.275) | 0.0004 |
| Day 2, 10 hours post-dose | −5.47 (2.275) | 0.0180 |
| Day 3, Pre-dose | −6.55 (2.275) | 0.0048 |
| Day 3, 4 hours post-dose | −6.22 (2.275) | 0.0073 |
| Day 3, 10 hours post-dose | −6.63 (2.275) | 0.0043 |
| Day 4, Pre-dose | −6.22 (2.275) | 0.0073 |
| Day 4, 4 hours post-dose | −9.30 (2.275) | 0.0001 |
| Day 4, 10 hours post-dose | −7.88 (2.275) | 0.0008 |

Abbreviations: ITT = intent to treat;
LS = least square;
SE = standard error;
MMRM = mixed models repeated measurements WBS Total Score—Bothersomeness of Symptoms The Total WBS Score equals the numerical sum total of all 19 questions, with a maximum score of 76 (most bothered by withdrawal symptoms).

As shown in Table 14, statistically significant differences were observed at all time points when participants were taking PP-01 as compared with when they were taking Placebo. Participants were less bothered by withdrawal symptoms when taking PP-01 than Placebo.

TABLE 14

LS Mean Difference Between PP-01 and Placebo
in Total WBS Score (ITT Population)

| | LS Mean Difference (SE) PP-01 Minus Placebo | MMRM P-value |
|---|---|---|
| Day 1, 4 hours post-dose | −7.78 (2.793) | 0.0063 |
| Day 1, 10 hours post-dose | −9.11 (2.793) | 0.0015 |
| Day 2, Pre-dose | −10.53 (2.793) | 0.0003 |
| Day 2, 4 hours post-dose | −11.03 (2.793) | 0.0001 |
| Day 2, 10 hours post-dose | −11.20 (2.793) | 0.0001 |
| Day 3, Pre-dose | −8.03 (2.793) | 0.0049 |
| Day 3, 4 hours post-dose | −8.70 (2.837) | 0.0027 |
| Day 3, 10 hours post-dose | −8.28 (2.793) | 0.0037 |
| Day 4, Pre-dose | −10.36 (2.793) | 0.0003 |

TABLE 14-continued

LS Mean Difference Between PP-01 and Placebo
in Total WBS Score (ITT Population)

| | LS Mean Difference (SE) PP-01 Minus Placebo | MMRM P-value |
|---|---|---|
| Day 4, 4 hours post-dose | −8.86 (2.793) | 0.0020 |
| Day 4, 10 hours post-dose | −7.70 (2.793) | 0.0069 |

Abbreviations: ITT = intent to treat;
LS = least square;
SE = standard error;
MMRM = mixed models repeated measurements

PGI-S

The PGI-S was completed by the study participants at Baseline (Day −1), Day 2, and Day 4 (approximately 4 hours post-dose on Days 2 and 4). Study participants were asked to best describe the severity of their *cannabis* withdrawal symptoms, on a 5-point scale with 0=none and 5=very severe, and if the participant checked mild, moderate, severe, or very severe, they were to check how bothered they were by their symptoms (not at all, somewhat bothered, moderately bothered, or very much bothered).

The mean and median PGI-S Score and degree of bothersomeness for each time point by treatment arm is summarized in Table 15. Participants taking PP-01 described the severity and bothersomeness of their withdrawal symptoms as being less severe and less bothersome on Days 2 and 4 with statistical significance observed on Day 2.

TABLE 15

PGI-S Score for Baseline, Day 2, and Day 4 (ITT Population)

| | PP-01 (N = 14) | Placebo (N = 14) | Difference from Placebo P-value (paired t-test) | Difference from Placebo Change from Baseline P-value (paired t-test) |
|---|---|---|---|---|
| Severity | | | | |
| Baseline, Day −1 (n) | 14 | 13 | 13 | 13 |
| Mean (SD) | 0.5 (0.85) | 0.5 (0.88) | 0.8193 | — |
| Median | 0.0 | 0.0 | — | — |
| Min, Max | 0, 3 | 0, 3 | — | — |
| Day 2 (n) | 13 | 13 | 12 | 12 |
| Mean (SD) | 1.2 (0.69) | 2.4 (1.04) | 0.0063 | 0.0246 |
| Median | 1.0 | 2.0 | — | — |
| Min, Max | 0, 2 | 1, 4 | — | — |
| Day 4 (n) | 13 | 13 | 12 | 12 |
| Mean (SD) | 1.1 (0.86) | 2.0 (1.35) | 0.1455 | 0.2410 |
| Median | 1.0 | 2.0 | — | — |
| Min, Max | 0, 3 | 0, 4 | — | — |
| Bothersomeness | | | | |
| Baseline, Day −1 (n) | 14 | 13 | 13 | 13 |
| Mean (SD) | 0.4 (0.85) | 0.4 (0.87) | 0.8193 | — |
| Median | 0.0 | 0.0 | — | — |
| Min, Max | 0, 3 | 0, 3 | — | — |
| Day 2 (n) | 13 | 13 | 12 | 12 |
| Mean (SD) | 1.0 (0.91) | 1.9 (0.86) | 0.0172 | 0.0848 |
| Median | 1.0 | 2.0 | — | — |
| Min, Max | 0, 3 | 1, 3 | — | — |
| Day 4 (n) | 13 | 13 | 12 | 12 |
| Mean (SD) | 0.8 (0.93) | 1.5 (1.13) | 0.1106 | 0.1941 |
| Median | 1.0 | 2.0 | — | — |
| Min, Max | 0, 3 | 0, 3 | — | — |

Abbreviations: ITT = intent to treat;
SD = standard deviation;
Min = minimum;
Max = maximum

CGI

The Principal Investigator, based on their experience of observing withdrawal symptoms, assessed whether study participants exhibited withdrawal symptoms on 4-point scale (0=not at all and 3=severely symptomatic). The CGI was administered at Baseline (Day −1) and on Days 2 and 4 (4 hours post-dose).

The mean and median CGI Score for each time point by treatment arm is summarized in Table 16 and details of the severity of withdrawal as assessed by the clinician are summarized in Table 17. On Days 2 and 4, symptom severity was statistically significantly lower for PP-01 as compared to Placebo.

TABLE 16

CGI Score for Baseline, Day 2, and Day 4 (ITT Population)

| | PP-01 (N = 14) | Placebo (N = 14) | Difference from Placebo P-value (paired t-test) | Difference from Placebo Change from Baseline P-value (paired t-test) |
|---|---|---|---|---|
| Severity | | | | |
| Baseline, Day −1 (n) | 14 | 13 | 13 | 13 |
| Mean (SD) | 0.5 (0.85) | 0.5 (0.88) | 0.8193 | — |
| Median | 0.0 | 0.0 | — | — |
| Min, Max | 0, 3 | 0, 3 | — | — |
| Day 2 (n) | 13 | 13 | 12 | 12 |
| Mean (SD) | 0.8 (0.44) | 2.1 (0.64) | 0.0001 | 0.0128 |
| Median | 1.0 | 2.0 | — | — |
| Min, Max | 0, 1 | 1, 3 | — | — |
| Day 4 (n) | 13 | 13 | 12 | 12 |
| Mean (SD) | 0.8 (0.73) | 1.8 (1.01) | 0.0197 | 0.0671 |
| Median | 1.0 | 2.0 | — | — |
| Min, Max | 0, 2 | 0, 3 | — | — |

Abbreviations: ITT = intent to treat;
SD = standard deviation;
Min = minimum;
Max = maximum

TABLE 17

CGI Severity Scores by Visit for Periods 1 and 2 Combined (ITT Population)

| Study Day | Severity | PP-01 | Placebo |
|---|---|---|---|
| −1 | n | 14 | 13 |
| | Not at all | 9 (64.3) | 9 (69.2) |
| | Mildly symptomatic | 4 (28.6) | 3 (23.1) |
| | Moderately symptomatic | 0 (0.0) | 0 (0.0) |
| | Severely symptomatic | 1 (7.1) | 1 (7.7) |
| 2 | n | 13 | 13 |
| | Not at all | 3 (23.1) | 0 (0.0) |
| | Mildly symptomatic | 10 (76.9) | 2 (15.4) |
| | Moderately symptomatic | 0 (0.0) | 8 (61.5) |
| | Severely symptomatic | 0 (0.0) | 3 (23.1) |
| 4 | n | 13 | 13 |
| | Not at all | 5 (38.5) | 2 (15.4) |
| | Mildly symptomatic | 6 (46.1) | 2 (15.4) |
| | Moderately symptomatic | 2 (15.4) | 6 (46.1) |
| | Severely symptomatic | 0 (0.0) | 3 (23.1) |

Abbreviations: ITT = intent to treat

Sleep

Sleep was measured by a separate sleep questionnaire that assessed both the quantity and quality of sleep, as well as by the 19-item CWS. Although PP-01 is intended to be given in the evening to provide a sleep benefit, in this study it was dosed in the morning due to operational considerations for PK collections.

Sleep Questionnaire

A sleep questionnaire was administered each morning and assessed problems that affected the quality and amount of sleep from the previous night and wakefulness each morning over past 24 hours. Participants treated with PP-01 on average had 30 minutes to 1.5 hours greater amount of sleep than Placebo, although statistical significance was reached only on Day 2. There was more time spent napping in the PP-01 treated participants.

Sleep quality was assessed by questions 9.1 to 9.6 where PP-01 was observed to provide statistically significant improvement in sleep quality.

TABLE 18

Sleep Quality Assessed by Questions 9.1 to 9.6 by Day (ITT Population)

| | PP-01 (N = 14) | Placebo (N = 14) | Difference from Placebo P-value (paired t-test) |
|---|---|---|---|
| Day −1 (n) | 14 | 13 | 13 |
| Mean (SD) | 22.8 (5.42) | 24.1 (5.22) | 0.4890 |
| Median | 24.0 | 25.0 | — |
| Min, Max | 12, 29 | 15, 30 | — |
| Day 1 (n) | 14 | 13 | 13 |
| Mean (SD) | 15.5 (6.36) | 13.6 (6.37) | 0.3221 |
| Median | 14.5 | 14.0 | — |
| Min, Max | 6, 26 | 6, 27 | — |
| Day 2 (n) | 13 | 13 | 12 |
| Mean (SD) | 22.5 (5.75) | 14.9 (5.54) | 0.0023 |
| Median | 24.0 | 15.0 | — |
| Min, Max | 6, 28 | 6, 26 | — |
| Day 3 (n) | 13 | 13 | 12 |
| Mean (SD) | 20.5 (6.08) | 16.0 (7.30) | 0.0344 |
| Median | 22.0 | 16.0 | — |

TABLE 18-continued

Sleep Quality Assessed by Questions
9.1 to 9.6 by Day (ITT Population)

|  | PP-01 (N = 14) | Placebo (N = 14) | Difference from Placebo P-value (paired t-test) |
|---|---|---|---|
| Min, Max | 6, 28 | 6, 30 | — |
| Day 4 (n) | 13 | 13 | 12 |
| Mean (SD) | 20.0 (6.62) | 16.6 (7.51) | 0.0135 |
| Median | 22.0 | 15.0 | — |
| Min, Max | 6, 30 | 6, 30 | — |
| Day 5 (n) | 13 | 13 | 12 |
| Mean (SD) | 20.5 (6.08) | 16.2 (7.51) | 0.0207 |
| Median | 20.0 | 17.0 | — |
| Min, Max | 6, 30 | 6, 30 | — |
| Day 8 (n) | 13 | 13 | 12 |
| Mean (SD) | 21.2 (7.75) | 25.3 (4.52) | 0.0531 |
| Median | 23.0 | 27.0 | — |
| Min, Max | 6, 30 | 14, 30 | — |

Figure 15:
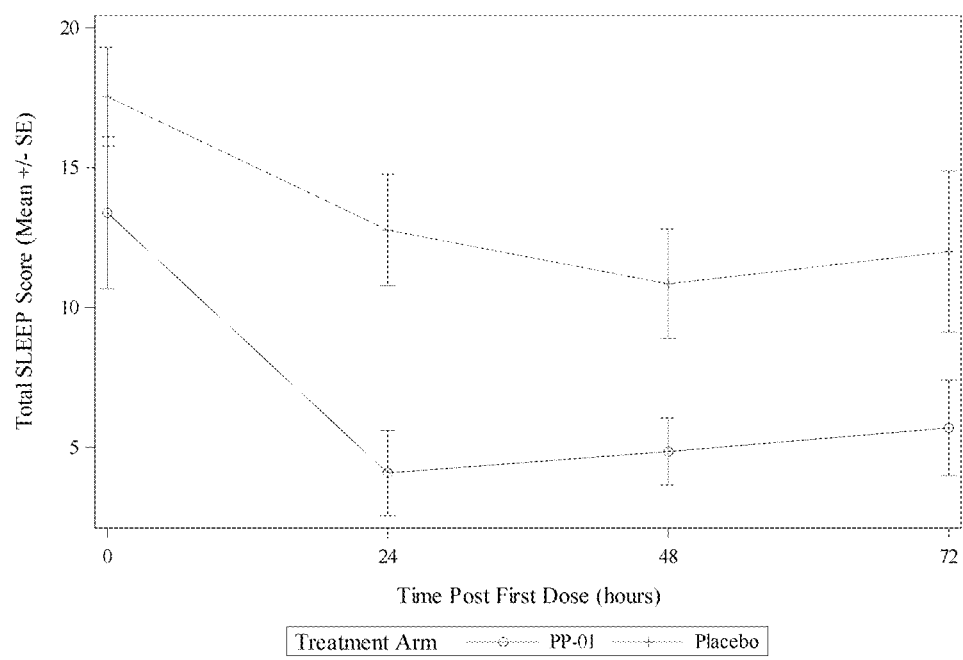
FIG. 15. Clinical Study—Mean total sleep score upon awakening: PP-01 vs placebo (ITT population).

Abbreviations: ITT = intent to treat;
SD = standard deviation;
Min = minimum;
Max = maximum CWS—Sleep Subscale The CWS has four questions related to sleep. The four questions included: 1) I woke up early; 2) I had nightmares and/or strange dreams; 3) I woke up sweating at night; and 4) I had trouble getting to sleep at night. The Total CWS Sleep Subscale Score equals the numerical sum of the four questions from the CWS questionnaire, for a maximum total of 40. As shown below in FIG. 14, sleep was improved for participants taking PP-01 with statistically significant changes at some time points on Days 2 and 4. The CWS was administered three times a day and therefore sleep questions were also asked three times daily. When participants were asked about their sleep upon wakening, statistically significant reductions in sleep issues were observed, as shown in FIG. 15.

WBS Sleep Subscale Score

The Total WBS Sleep Subscale Score equals the numerical sum of four questions from the WBS questionnaire, for a maximum total of 16. The four questions included: 1) I woke up early; 2) I had nightmares and/or strange dreams; 3) I woke up sweating at night; and 4) I had trouble getting to sleep at night.

Figure 16:
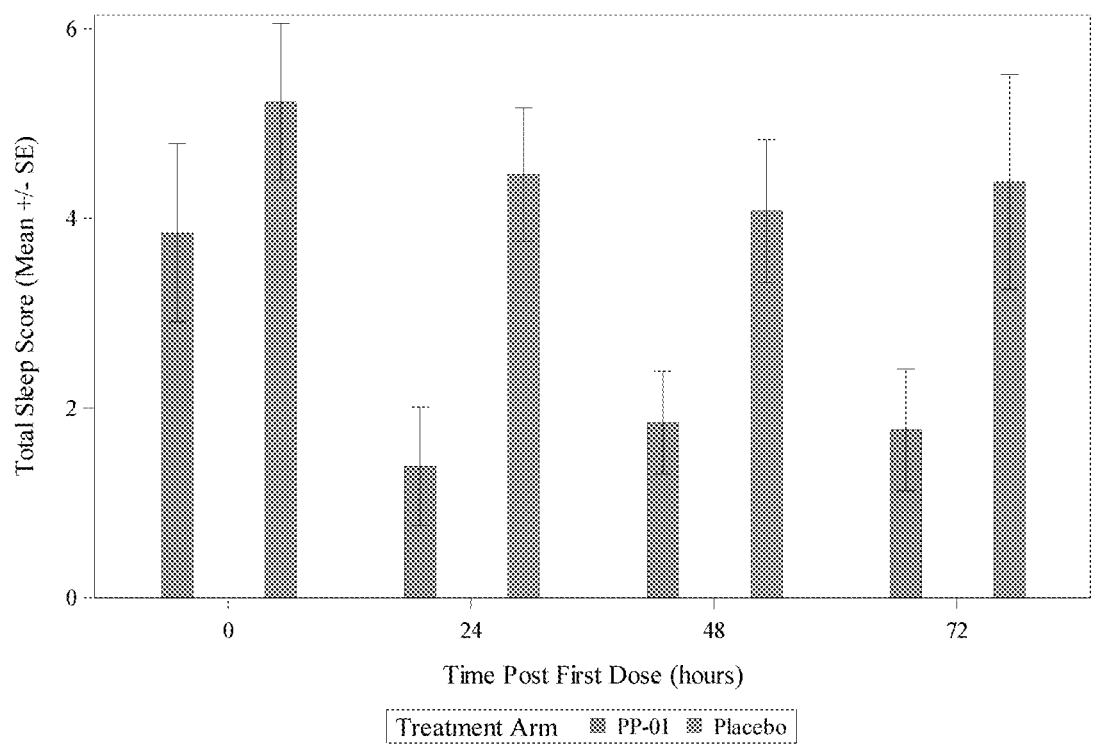
FIG. 16. Clinical Study—Mean total WBS sleep score by time point: PP-01 vs placebo (ITT population).

As shown in FIG. 16, overall, participants were less bothered by sleep difficulties when treated with PP-01 than Placebo.

Food Intake

Food intake was assessed by using the participant consumption percentage (100%, 75%, 50%, 25%, or 0%) of each meal and were recorded on site meal longs. The start and end time of each meal was also collected. For the three main meals (breakfast, lunch, and dinner), the percentage consumption per day was added together and divided by 100; the maximum value equaled 3.0. For the three snacks, any percentage consumption above zero was counted as one and added together; the maximum value equaled 3.0. Food and snack consumption were higher when participants received PP-01 than when receiving Placebo.

TABLE 19

Meal and Snack Consumption (ITT Population)

|  | BLD PP-01 (N = 14) | BLD Placebo (N = 14) | BLD Difference from Placebo P-value (paired t-test) | Snack PP-01 (N = 14) | Snack Placebo (N = 14) | Snack Difference from Placebo P-value (paired t-test) |
|---|---|---|---|---|---|---|
|  | 13 | 13 | 12 | 13 | 13 | 12 |
| Day 1 (n) | | | | | | |
| Mean (SD) | 2.4 (0.45) | 1.9 (0.63) | 0.0127 | 1.9 (1.26) | 0.9 (1.19) | 0.0197 |
| Median | 2.5 | 1.8 | — | 2.0 | 0.0 | — |
| Min, Max | 1.8, 3.0 | 0.8, 3.0 | — | 0.0, 3.0 | 0.0, 3.0 | — |
| Day 2 (n) | | | | | | |
| Mean (SD) | 2.4 (0.43) | 2.3 (0.67) | 0.4664 | 2.5 (0.66) | 1.4 (0.96) | 0.0006 |
| Median | 2.5 | 2.5 | — | 3.0 | 1.0 | — |
| Min, Max | 1.8, 3.0 | 0.8, 3.0 | — | 1.0, 3.0 | 0.0, 3.0 | — |
| Day 3 (n) | | | | | | |
| Mean (SD) | 2.2 (0.49) | 1.8 (0.60) | 0.0074 | 2.5 (0.66) | 1.8 (0.99) | 0.0388 |
| Median | 2.3 | 1.8 | — | 3.0 | 2.0 | — |
| Min, Max | 1.5, 3.0 | 0.8, 3.0 | — | 1.0, 3.0 | 0.0, 3.0 | — |
| Day 4 (n) | | | | | | |
| Mean (SD) | 2.3 (0.65) | 1.8 (0.66) | 0.0074 | 1.8 (0.99) | 1.1 (1.04) | 0.0055 |
| Median | 2.5 | 1.8 | — | 2.0 | 1.0 | — |
| Min, Max | 0.8, 3.0 | 1.0, 3.0 | — | 0.0, 3.0 | 0.0, 3.0 | — |

Abbreviations:
ITT = intent to treat;
BLD = breakfast, lunch, and dinner;
SD = standard deviation;
Min = minimum;
Max = maximum Weight Body weight was to be obtained daily with participants' shoes off and jacket or coat removed. Participants with both Period 1 and Period 2 Baseline values (Day −1) and visits are included; there were 13 participants with both a Period 1 and 2 Baseline assessment (Day −1) and 12 participants with both Period 1 and 2, Baseline (Day −1) and Day 5 assessments.

Figure 17:
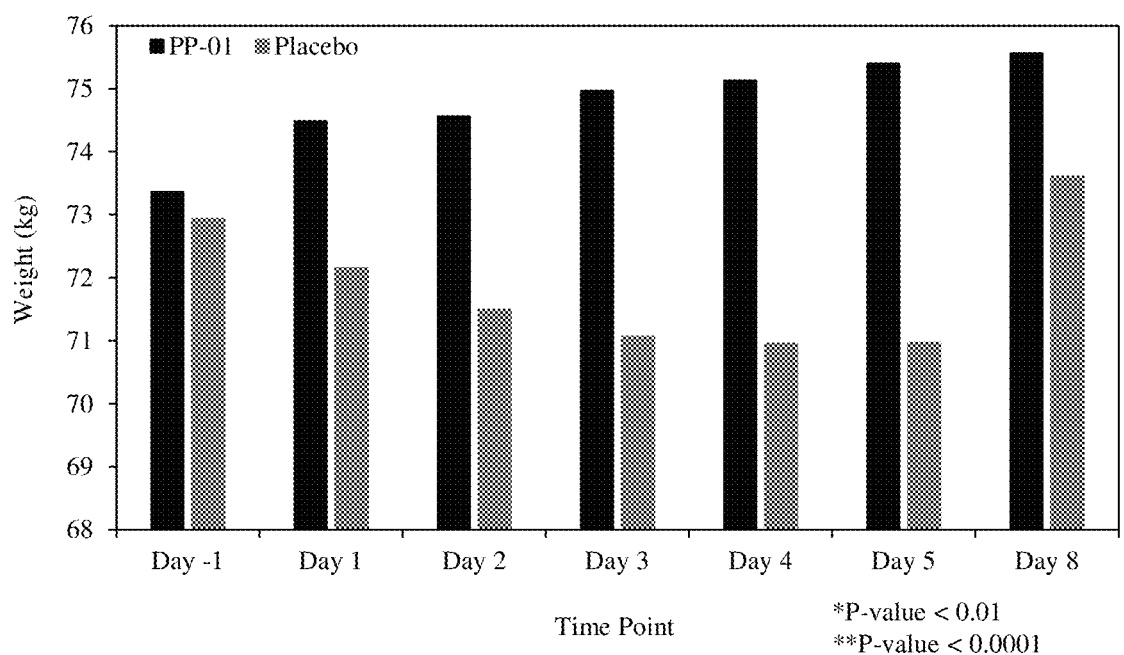
FIG. 17. Clinical Study—Body weight (ITT population) results.

As shown in FIG. 17, mean weights for those randomized to PP-01 or Placebo at Baseline (Day −1) were not different. Starting at Day 2 and continuing through Day 5 (note that the last day of study drug administration was Day 4), statistically significant differences were observed between PP-01 and Placebo. While taking Placebo, participants lost approximately 2 kg between Baseline and Day 5 consistent with their decreased appetite and food intake. Weight was maintained when taking PP-01. At Day 8, the differences were no longer statistically significant.

Cortisol

Figure 18:
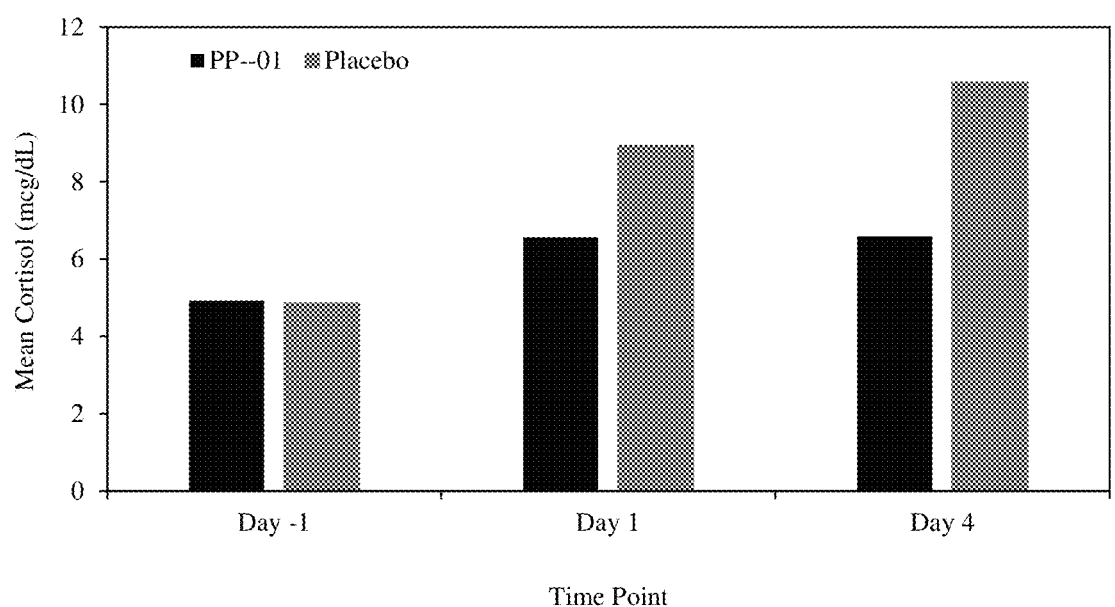
FIG. 18. Clinical Study—Evening serum cortisol levels results.

Evening cortisol was assessed as marker of stress. Serum cortisol was drawn in the evening at the time of the last PK sample on Day −1, Day 1, and Day 4. The change from Baseline (Day −1) for PP-01 and Placebo and differences from placebo are summarized below in Table 20. At Baseline (Day −1), evening cortisol levels were not different between the PP-01 and Placebo groups. At Day 1, the mean cortisol level in the Placebo group was numerically higher than in the PP-01 group (8.931 vs 6.562 µg/dL, respectively), and at Day 4, the difference was statistically significantly different (10.569 vs 6.585 µg/dL, respectively, P-value=0.0013). The difference between PP-01 and Placebo change from Baseline was also statistically significant (P-value=0.0039). The serum cortisol levels for PP-01 and Placebo at each time point is shown graphically in FIG. 18.

As cortisol is a marker of stress, these data indicate that participants in the Placebo group were experiencing a higher level of stress during *cannabis* withdrawal than participants who received PP-01 over the four-day treatment period.

TABLE 20

Evening Serum Cortisol Levels (Safety Population)

| Day | Parameter | PP-01 (N = 14) | Placebo (N = 14) | Difference PP-01 Minus Placebo | Difference PP-01 Minus Placebo Change from Baseline |
|---|---|---|---|---|---|
| −1 | N | 14 | 13 | 13 | 13 |
|  | Mean (SD), µg/dL | 4.921 (1.6614) | 4.854 (2.4979) | 0.123 (2.3449) | 0.000 (0.0000) |
|  | Median, µg/dL | 4.200 | 4.400 | −0.100 | 0.000 |
|  | Min, Max, µg/dL | 2.50, 8.60 | 1.60, 4.40 | −2.70, 5.20 | 0.00, 0.00 |
|  | P-value (paired t-test) | — | — | 0.8531 | — |
| 1 | n | 13 | 13 | 12 | 12 |
|  | Mean (SD), µg/dL | 6.562 (3.9371) | 8.931 (4.5906) | −2.092 (4.4580) | −2.450 (5.4080) |
|  | Median, µg/dL | 6.200 | 8.100 | −2.150 | −3.350 |
|  | Min, Max, µg/dL | 1.50, 16.50 | 2.50, 17.80 | −9.30, 4.10 | −10.50, 6.00 |
|  | P-value (paired t-test) | — | — | 0.1324 | 0.1449 |
| 4 | n | 13 | 13 | 12 | 12 |
|  | Mean (SD), µg/dL | 6.585 (2.7817) | 10.569 (4.6761) | −4.208 (3.3918) | −4.567 (4.3410) |
|  | Median, µg/dL | 5.800 | 8.600 | −3.600 | −4.850 |
|  | Min, Max, µg/dL | 2.00, 11.70 | 3.90, 19.30 | −9.80, 1.00 | −11.00, 1.90 |
|  | P-value (paired t-test) | — | — | 0.0013 | 0.0039 |

Abbreviations: SD = standard deviation;
Min = minimum;
Max = maximum

Heart Rate

The standing HR when participants were receiving Placebo was statistically significantly higher than when treated with PP-01 as shown below in Table 21.

TABLE 21

Standing Heart Rate (Safety Population)

| Day | Parameter | PP-01 (N = 14) | Placebo (N = 14) | Difference PP-01 Minus Placebo | Difference PP-01 Minus Placebo Change from Baseline |
|---|---|---|---|---|---|
| 1 | n | 13 | 13 | 12 | — |
| Pre-dose | Mean (SD) | 85.4 (12.55) | 81.5 (11.00) | 3.8 (18.36) | — |
|  | Median | 86.0 | 80.0 | 6.5 | — |
|  | Min, Max | 62, 108 | 65, 108 | −37, 28 | — |
|  | P-value (paired t-test) | — | — | 0.4939 | — |
| 2 | n | 13 | 13 | 12 | 12 |
| Pre-dose | Mean (SD) | 83.5 (10.35) | 83.7 (12.53) | −1.5 (12.49) | −5.3 (21.35) |
|  | Median | 84.0 | 84.0 | 1.5 | −5.5 |
|  | Min, Max | 56, 98 | 64, 108 | −28, 18 | −56, 28 |
|  | P-value (paired t-test) | — | — | 0.6853 | 0.4125 |

TABLE 21-continued

Standing Heart Rate (Safety Population)

| Day | Parameter | PP-01 (N = 14) | Placebo (N = 14) | Difference PP-01 Minus Placebo | Difference PP-01 Minus Placebo Change from Baseline |
|---|---|---|---|---|---|
| 3 Pre-dose | n | 13 | 13 | 12 | 12 |
| | Mean (SD) | 82.5 (10.17) | 95.5 (17.88) | −12.9 (15.80) | −16.7 (26.73) |
| | Median | 81.0 | 93.0 | −9.5 | −14.5 |
| | Min, Max | 73, 114 | 68, 128 | −42, 6 | −62, 32 |
| | P-value (paired t-test) | — | — | 0.0163 | 0.0537 |
| 4 Pre-dose | n | 13 | 13 | 12 | 12 |
| | Mean (SD) | 83.2 (10.06) | 96.0 (15.04) | −14.3 (10.38) | −18.0 (17.56) |
| | Median | 83.0 | 98.0 | −17.0 | −16.5 |
| | Min, Max | 62, 99 | 67, 118 | −24, 12 | −43, 17 |
| | P-value (paired t-test) | — | — | 0.0006 | 0.0045 |

Abbreviations: SD = standard deviation;
Min = minimum;
Max = maximum

There was a statistically significant correlation with the CWS Total Score and the evening cortisol level at the Day 4 10-hour time point for Periods 1 and 2 (P value=0.0455 and 0.0272, respectively).

Discussion of Efficacy Results

Mitigation of withdrawal symptoms was observed when participants were treated with PP-01 compared with Placebo. The primary outcome measure was the 19-Item CWS questionnaire which showed statistically significant and clinically meaningful differences where participants were observed to be less bothered by CWS symptoms (CWS 2) when participants received PP-01 rather than Placebo. Mean differences between PP-01 and Placebo were statistically significant with less CWS with PP-01. Importantly, and surprisingly, this benefit was observed at nearly every timepoint, as early as 4 hours post dose and was sustained through Day 5. Reduction in CWS with PP-01 was observed regardless of age and treatment period. Additional analyses showed that 6-Items on the 19-Item scale were more significant for a majority of participants experiencing withdrawal and again these items were significantly reduced when participants were treated with PP-01 than with Placebo. These findings were robust as evidenced by the consistency of effect. Additionally, in a single period analysis with just seven participants per group statistical significance was observed with a reduction in CWS when participants were treated with PP-01 compared with Placebo. Cravings were also significantly reduced in participants treated with PP-01. Despite being dosed in the morning, sleep measures revealed improved quality of sleep with statistically significant differences favoring PP-01. The amount of time slept at night was greater by 30 minutes to 1.7 hour when subjects were treated with PP-01, statistical significance was achieved on Day −2. More time was spent napping in those treated with PP-01.

Both participants' self-assessed and clinician assessment of CWS were significantly reduced with PP-01 compared with Placebo.

Parameters assessing the physiological consequences of withdrawal were measured and included weight, evening serum cortisol and vital signs. Weight loss was statistically different when participants received placebo, which was consistent with a decrease in their appetite and food intake, whereas weight was maintained with PP-01 treatment. Evening serum cortisol was significantly higher on Day 4 with Placebo compared with PP-01 indicating prolonged stress with withdrawal. Standing heart rate also elevated with statistically significant elevations observed when participants received Placebo compared with the PP-01.

Efficacy Conclusions

PP-01 strongly and rapidly mitigated CWS in this Phase 1 study of 14 participants with moderate to severe CUD who reported using various amounts (greater than at least 1 gram) and types of cannabis. There was a robust and consistent effect of PP-01. When measured by various outcomes including questionnaires, patient self-assessment, clinician assessments and physiologic parameters, PP-01 was observed to reduce withdrawal symptoms typically observed with cannabis withdrawal. Sleep difficulties and cravings, two common and troublesome symptoms associated with cannabis withdrawal, were both were mitigated by PP-01. Overall, PP-01 decreased bothersome withdrawal symptoms.

Example 2. Randomized, Double-Blind, Placebo-Controlled Clinical Trial of Titrating Doses of Nabilone with or without Gabapentin for the Mitigation of Cannabis Withdrawal Symptoms in Patients with Moderate to Severe Cannabis Use Disorder Seeking to Discontinue Cannabis Study Overview Randomized, double blind studies of nabilone/gabapentin combination therapy are conducted. The target population for the treatment includes participants who desire to or must decrease cannabis use but have previously been unsuccessful due to symptoms of cannabis withdrawal.

Nabilone and gabapentin are provided to patients according to the dosing regime set forth below, or alternatively, the dosage regimes set forth in FIGS. 19 and 20. Withdrawal, PK, PD, safety, tolerability and biometric assessments are made as set forth in Example 1.

The PP-01 maximum dose of 6.0 mg (Arm 1) or 3.0 mg of nabilone (Arm 2) with gabapentin 300 mg is to start on the first day of cannabis discontinuation and is to be titrated down to 0.0 mg. During the study, tapering/titration of PP-01, and nabilone and gabapentin alone, will occur over 42 days following the schedule below (Table 22). Patients will take 7 capsules each day of active and or matching placebo.

TABLE 22

Tapering/Titration Dosing Schedule

| Days | Nabilone/Gabapentin (PP-01) (mg) | | Matching Placebo (P) | Nabilone (mg) | Gabapentin (mg) |
|---|---|---|---|---|---|
| | Arm 1 N = 85 | Arm 2 N = 85 | Arm 3 N = 85 | Arm 4 N = 42 | Arm 5 N = 42 |
| 1-3 | 6.0/300 | 3.0/300 | P | 6.0 | 300 |
| 4-7 | 5.0/600 | 2.5/600 | P | 5.0 | 600 |
| 8-10 | 4.0/900 | 2.0/900 | P | 4.0 | 900 |
| 11-14 | 3.0/1200 | 1.5/1200 | P | 3.0 | 1200 |
| 15-17 | 2.0/1200 | 1.0/1200 | P | 2.0 | 1200 |
| 18-21 | 1.0/1200 | 0.5/1200 | P | 1.0 | 1200 |
| 22-24 | 0.5/1200 | 0.25/1200 | P | 0.5 | 1200 |
| 25-28 | 0.25/600 | 0.0/600 | P | 0.25 | 600 |
| 29-31 | 0.0/600 | 0.0/300 | P | 0.0 | 300 |
| 32-35 | 0.0/300 | 0.0/0.0 | P | 0.0 | 0.0 |

Alternative dosing schedules for the 6 mg nabilone plus gabapentin arm (Arm 1) are show in FIGS. 19 and 20. Additionally, the dosing schedules be adjusted to increase the starting gabapentin dose to 600 mg per day. Patients may optionally be administered 300 mg gabapentin on the day preceding combination nabilone/gabapentin therapy.

Subjects will be instructed to refrain from all *cannabis* and CBD containing products. If they cannot refrain, they are to record what and how much they have used. Baseline levels of THC and THC metabolites, nabilone, nabilone metabolite, and gabapentin will be drawn in all participants. The CWS, and sleep questionnaires are to be filled out daily. Questionnaires assessing the participants' PGA, the clinicians' CGA, and sleep quality will be completed at each study visit.

Subjects who meet eligibility criteria will be randomized into active or placebo arms. A total of approximately 340 patients (85 per arm for PP-01 and placebo and 42 per arm of nabilone and gabapentin alone) will be enrolled with the expectation that 30% (at least 25 patients per PP-01 and placebo arms) will complete Day 40.

Study participants will be assigned to one of five treatment arms as follows:
1. PP-01—starting dose of 6.0 mg nabilone and 300 mg of gabapentin
2. PP-01—starting dose of 3.0 mg nabilone and 300 mg of gabapentin
3. Matching Placebo
4. Nabilone only—starting dose of 6.0 mg
5. Gabapentin only—starting dose of 300 mg Assessment of Efficacy Site personnel will review and explain how to complete the questionnaires and the important of accurate responses.

CWS

The CWS asks about symptoms experienced over the last 24 hours. Study participants will be asked to complete the CWS at Baseline and then each evening of every day throughout the study; their responses should reflect how they have felt since the last time the questionnaire was completed.

The CWS will also assess how bothered subjects are by their *cannabis* withdrawal symptoms.

Sleep

This questionnaire is to be completed each morning and assesses problems that affected the quality and amount of sleep from the previous night and wakefulness each morning. This questionnaire refers to sleep over the past 24 hours.

PGI-S

At each clinic visit, participants will be instructed to describe the severity of their *cannabis* withdrawal symptoms and how bothered they were by their symptoms.

CGI

At each clinic visit, the Principal Investigator will assess whether the subjects appear to be experiencing withdrawal symptoms given their experience of observing withdrawal symptoms.

Weight

Body weight will be obtained daily with the participants' shoes off, and jacket or coat removed.

The results of this study demonstrate strong and rapid reduction in *cannabis* withdrawal symptoms, including reductions in cravings, irritability, and sleep disturbances in treated patients compared to placebo controls. Cortisol levels are maintained at comfortable levels and treated patients demonstrate non-elevated heart rates and maintenance of normal body weight in contrast to placebo patients. Importantly, the study provides, for the first time, an effective and limited duration treatment regime for *cannabis* withdrawal.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A method of treating *cannabis* withdrawal syndrome, comprising administering to a patient in need thereof about 6 mg of nabilone and a therapeutically effective amount of gabapentin on a daily basis, wherein the amount of gabapentin administered is about 100-800 mg per day.

2. The method of claim 1, wherein the amount of gabapentin administered is about 300-600 mg per day.

3. The method of claim 1, wherein the treatment results in a reduction in *cannabis* withdrawal syndrome symptoms as measured by evening cortisol levels, sleep, weight loss, standing heart rate, craving or withdrawal scoring based on the results of one or more questionnaires administered to the subject, withdrawal symptoms based on observations of a health care provider, and combinations thereof.

4. The method of claim 1, wherein the reduction in symptoms occurs within a time frame following administration of nabilone and gabapentin selected from the group consisting of about 36 hours, about 24 hours, about 18 hours, about 12 hours, about 10 hours, about 8 hours, about 6 hours, and about 4 hours or less.

5. The method of claim 1, wherein the daily dose is administered for at least 3 days.

6. The method of claim 1, wherein the daily dose of nabilone and gabapentin is administered twice daily.

7. The method of claim 1, wherein the daily dose of nabilone and gabapentin is administered once daily.

8. The method of claim 1, wherein the daily dose of nabilone is reduced by at least 15% every 3 or 4 days.

9. The method of claim 1, wherein the daily doses of nabilone and gabapentin are adjusted according to the following schedule:

| Dose | Nabilone (mg) | Gabapentin (mg) |
|---|---|---|
| 1 | 6 | 300 |
| 2 | 5 | 600 |
| 3 | 4 | 900 |
| 4 | 3 | 900 |
| 5 | 2 | 900 |
| 6 | 1 | 900 |
| 7 | 0.5 | 1200 |
| 8 | 0.25 | 900 |
| 9 | 0 | 900 |
| 10 | 0 | 900 or 600 |
| 11 | 0 | 300 | wherein each dose is administered for one or more days.

10. The method of claim 1, wherein the treatment results in a reduction in *cannabis* withdrawal syndrome symptoms as measured by a CWS score, wherein the daily dose of nabilone and/or gabapentin is adjusted in a manner that maintains a CWS score to within about 150% of a CWS score that is achieved about 24 hrs after the first dose of nabilone and gabapentin is administered.

11. The method of claim 1, wherein the treatment results in a reduction in *cannabis* withdrawal syndrome symptoms as measured by evening cortisol levels, wherein the daily dose of nabilone and/or gabapentin is adjusted in a manner that limits any increase in evening cortisol levels to no more than 120% of cortisol levels that are achieved at or within about 24 hrs after the first dose of nabilone and gabapentin is administered.

12. The method of claim 1, wherein the treatment results in a reduction in *cannabis* withdrawal syndrome symptoms as measured by standing heart rate, wherein the daily dose of nabilone and/or gabapentin is adjusted in a manner that limits any increase in standing heart rate to no more than 5% of the standing heart rate measured about 24 hrs after the first dose of nabilone and gabapentin is administered.

13. The method of claim 1, wherein the treatment results in a reduction in *cannabis* withdrawal syndrome symptoms as measured by appetite and body weight, wherein the daily dose of nabilone and/or gabapentin is adjusted in a manner that limits any weight loss to no more than 1 kg (2.2 lbs) or less of the subject's weight measured about 24 hrs after the first dose of nabilone and gabapentin is administered.

14. The method of claim 1, wherein the reduction in *cannabis* withdrawal syndrome symptoms comprises a reduction in craving sensations.

15. The method of claim 1, wherein the reduction in *cannabis* withdrawal syndrome symptoms comprises a reduction in sleep disturbance and/or an improvement in sleep quality.

16. The method of claim 1, wherein the treatment results in a reduction in *cannabis* withdrawal syndrome symptoms as measured by one or more assessment tool selected from the group consisting of WBS score, WBS 6 question subscale score, CWS 6 question subscale score, the Craving subscale, PGI-S, PGI bothersomeness or CGI, wherein the daily dose of nabilone and gabapentin is adjusted in a manner that maintains a withdrawal score on the selected assessment tool to within 150% of the score that is achieved about 24 hours after the first dose of nabilone and gabapentin is administered.

17. The method of claim 1, wherein the treatment results in a reduction in *cannabis* withdrawal syndrome symptoms as measured by one or more assessment tool selected from the group consisting of WBS score, WBS 6 question subscale score, CWS 6 question subscale score, the Craving subscale, PGI-S scale, PGI bothersomeness scale or CGI scale, wherein the daily dose of nabilone and gabapentin is adjusted in a manner that maintains a withdrawal score on the selected assessment tool as selective from the group consisting of, a score of 40 or less on the CWS, a score of 25 or less on the CWS 6 question subscale, a score of 20 or less on the WBS, a score of 4 or less on WBS 6 question subscale, a score of 2 or less on the Craving subscale, a score of 1.5 or less on the PGI-S scale, a score of 1.0 or less on the PGI bothersomeness scale or a score of 1.5 or less on the CGI.

18. A method of treating *cannabis* withdrawal syndrome, comprising administering on a daily basis to a patient in need thereof nabilone in an amount sufficient to achieve a mean $AUC_{0-24}$ range of 23100-47250 pg-hr/mL and gabapentin in an amount sufficient to achieve a mean $AUC_{0-24}$ range of 17500-97875 pg-hr/mL.

19. The method of claim 18, wherein nabilone is administered in an amount sufficient on a daily basis to achieve a mean $AUC_{0-24}$ range of 26400-43750 pg-hr/mL and gabapentin is administered in an amount sufficient on a daily basis to achieve a mean $AUC_{0-24}$ range of 20000-90625 pg-hr/mL.

20. The method of claim 18, wherein the amount of gabapentin administered is about 200-750 mg per day.

21. The method of claim 18, wherein the amount of nabilone administered is 3-7 mg per day.

22. A kit comprising:
a. a plurality of daily doses of nabilone;
b. a plurality of daily doses of gabapentin; and
c. optionally a dosing schedule for administering the nabilone and gabapentin,
wherein the kit contains daily doses of nabilone and gabapentin sufficient to provide daily doses for a period of time selected from the group consisting of 30 to 60 days, 21 to 42 days, and about 4 weeks or 1 month.

23. The kit of claim 22, comprising initial daily doses of nabilone of 6 mg.

24. The kit of claim 22, comprising initial daily doses of gabapentin of 300-600 mg.

25. The kit of claim 22, wherein the plurality of daily doses of nabilone comprises daily doses of nabilone selected from 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg and combinations thereof.

26. The kit of claim 22, wherein the plurality of daily doses of gabapentin comprises daily doses of gabapentin selected from 200 mg, 300 mg, 400 mg, 500 mg, 600 mg, 700 mg, 800 mg, 900 mg 1000 mg, 1100 mg, 1200 mg, 1300 mg, 1400 mg, 1500 mg and combinations thereof.

27. The kit of claim 22, wherein the daily doses for one week are presented on a solid substrate.

28. The kit of claim 27, wherein the solid substrate is a blister pack.

29. The kit of claim 22, further comprising one or more *cannabis* withdrawal syndrome symptom questionnaires.

30. The kit of claim 22, wherein the kit contains daily doses of nabilone and gabapentin sufficient to provide daily doses for 30 to 60 days.

31. The kit of claim 22, wherein the kit contains daily doses of nabilone and gabapentin sufficient to provide daily doses for 21 to 42 days.

32. The kit of claim 22, wherein the kit contains daily doses sufficient to provide daily doses for about 4 weeks or 1 month.

33. The method of claim 1, wherein the amount of gabapentin administered is about 200 to 300 mg per day.

34. A method of treating *cannabis* withdrawal syndrome, comprising administering to a patient in need thereof therapeutically effective daily doses of nabilone and gabapentin, wherein the nabilone daily dose is from 5 to 7 mg per day and the gabapentin daily dose is from 50 to 700 mg per day and wherein the daily doses are administered for a period of time of between two to seven days.

35. The method of claim 34, wherein subsequent daily doses of nabilone and gabapentin are administered for a second period of time, wherein the nabilone daily dose is from 4 to 6 mg per day and the gabapentin daily dose is from 300 to 1000 mg per day and wherein the daily doses are administered for a second period of time of between two to seven days.

36. The method of claim 35, wherein subsequent daily doses of nabilone and gabapentin are administered for a third period of time, wherein the nabilone daily dose is from 3 to 5 mg per day and the gabapentin daily dose is from 300 to 1200 mg per day and wherein the daily doses are administered for a third period of time of between two to seven days.

37. The method of claim 36, wherein subsequent daily doses of nabilone and gabapentin are administered for a fourth period of time, wherein the nabilone daily dose is from 2 to 4 mg per day and the gabapentin daily dose is from 300 to 1200 mg per day and wherein the daily doses are administered for a fourth period of time of between two to seven days.

38. The method of claim 37, wherein subsequent doses of nabilone and gabapentin are administered for a fifth period of time, wherein the nabilone daily dose is from 1 to 3 mg per day and the gabapentin daily dose is from 300 to 1200 mg per day and wherein the daily doses are administered for a fifth period of time of between two to seven days.

39. The method of claim 38, wherein subsequent doses of nabilone and gabapentin are administered for a sixth period of time, wherein the nabilone daily dose is from 0.5 to 2 mg per day and the gabapentin daily dose is from 300 to 1200 mg per day and wherein the daily doses are administered for a sixth period of time of between two to seven days.

40. The method of claim 39, wherein subsequent doses of nabilone and gabapentin are administered for a seventh period of time, wherein the nabilone daily dose is from 0.25 to 1 mg per day and the gabapentin daily dose is from 300 to 1000 mg per day and wherein the daily doses are administered for a seventh period of time of between two to seven days.

41. The method of claim 40, wherein subsequent doses of nabilone and gabapentin are administered for a eighth period of time, wherein the nabilone daily dose is from 0.0 to 0.5 mg per day and the gabapentin daily dose is from 300 to 1000 mg per day and wherein the daily doses are administered for a eighth period of time of between two to seven days.

* * * * *